(12) United States Patent
Qin et al.

(10) Patent No.: US 11,911,435 B2
(45) Date of Patent: *Feb. 27, 2024

(54) STABLE ANTIBODY-DRUG CONJUGATE, PREPARATION METHOD THEREFOR, AND USE THEREOF

(71) Applicant: GENEQUANTUM HEALTHCARE (SUZHOU) CO., LTD., Suzhou (CN)

(72) Inventors: Gang Qin, Jiangsu (CN); Jinduo Yuan, Jiangsu (CN); Lu Jiang, Jiangsu (CN); Chubing Tan, Jiangsu (CN); Lili Shi, Jiangsu (CN); Cao Lv, Jiangsu (CN); Leilei Chen, Jiangsu (CN)

(73) Assignee: GENEQUANTUM HEALTHCARE (SUZHOU) CO., LTD., Jiangsu (CN)

(*) Notice: Subject to any disclaimer, the term of this patent is extended or adjusted under 35 U.S.C. 154(b) by 245 days.

This patent is subject to a terminal disclaimer.

(21) Appl. No.: 17/180,645

(22) Filed: Feb. 19, 2021

(65) Prior Publication Data

US 2021/0177929 A1 Jun. 17, 2021

Related U.S. Application Data

(63) Continuation of application No. 15/307,738, filed as application No. PCT/CN2015/077887 on Apr. 29, 2015, now Pat. No. 11,040,084.

(30) Foreign Application Priority Data

Apr. 29, 2014 (CN) .......................... 201410174890.8

(51) Int. Cl.
  *A61K 38/07* (2006.01)
  *A61K 31/537* (2006.01)
  (Continued)

(52) U.S. Cl.
  CPC ............ *A61K 38/07* (2013.01); *A61K 31/537* (2013.01); *A61K 45/00* (2013.01); *A61K 47/50* (2017.08);
  (Continued)

(58) Field of Classification Search
  None
  See application file for complete search history.

(56) References Cited

U.S. PATENT DOCUMENTS 9,872,923 B2 1/2018 Grawunder et al.
11,040,084 B2 6/2021 Qin et al.
(Continued)

FOREIGN PATENT DOCUMENTS

CN  102973947  3/2007
CN    1938046  3/2013
(Continued)

OTHER PUBLICATIONS

Shen et al. Nature Biotech, 2012, 30, 184-189 (Year: 2012).*
(Continued)

*Primary Examiner* — Karl J Puttlitz
(74) *Attorney, Agent, or Firm* — Hoxie & Associates LLC

(57) ABSTRACT

A conjugate and preparation method therefor, comprising a medication composition comprising the conjugate and a use of the medication composition in preparing medications for the treatment or prevention of diseases.

22 Claims, 30 Drawing Sheets

Specification includes a Sequence Listing.

(51) Int. Cl.
| | | |
|---|---|---|
| *A61K 45/00* | (2006.01) | |
| *A61K 47/68* | (2017.01) | |
| *A61K 47/50* | (2017.01) | |
| *C07K 16/28* | (2006.01) | |
| *C07K 16/32* | (2006.01) | |
| *A61K 39/00* | (2006.01) | |

(52) U.S. Cl.
CPC ...... *A61K 47/6851* (2017.08); *C07K 16/2863* (2013.01); *C07K 16/32* (2013.01); *A61K 2039/505* (2013.01); *C07K 2317/92* (2013.01)

(56) References Cited

U.S. PATENT DOCUMENTS

| | | | |
|---|---|---|---|
| 11,453,870 B2 | 9/2022 | Qin et al. | |
| 11,578,297 B2 | 2/2023 | Qin et al. | |
| 2010/0129314 A1* | 5/2010 | Singh ................ | A61K 47/6889 514/1.1 |
| 2011/0321183 A1 | 12/2011 | Ploegh et al. | |
| 2013/0309256 A1 | 11/2013 | Lyon et al. | |
| 2016/0193355 A1 | 7/2016 | Qin et al. | |
| 2018/9872923 | 1/2018 | Grawunder et al. | |
| 2018/0104349 A9 | 4/2018 | Qin et al. | |
| 2021/0187114 A1 | 6/2021 | Qin et al. | |
| 2021/0221907 A1 | 7/2021 | Hou et al. | |
| 2021/0401924 A1 | 12/2021 | Qin et al. | |
| 2022/0378930 A1 | 12/2022 | Song et al. | |
| 2022/0395581 A1 | 12/2022 | Qin et al. | |
| 2022/0403360 A1 | 12/2022 | Qin et al. | |
| 2023/0097252 A1 | 3/2023 | Qin et al. | |
| 2023/0101266 A1 | 3/2023 | Qin et al. | |

FOREIGN PATENT DOCUMENTS

| | | |
|---|---|---|
| WO | WO 2005/081711 A2 | 9/2005 |
| WO | WO 2005/117986 A2 | 12/2005 |
| WO | 2014055877 * | 4/2014 |
| WO | WO 2014/055877 | 4/2014 |
| WO | WO 2014/177042 A1 | 11/2014 |

OTHER PUBLICATIONS

Lyon et al., Cancer Res (2013) 73 (8_Supplement): 4333, Abstract (Year: 2013).*

Kornberger et al., mAbs, 2014, 6, 354-366 (Year: 2014).*

Bauer, D. et al., "Clickable Tyrosine Binding Bifunctional Linkers for Preparation of DNA-Protein Conjugates," Bioconjugate Chemistry, 2013, 24 (6), 1094-1101.

Tsukiji, S. et al., "Sortase-Mediated Ligation: A Gift from Gram-Positive Bacteria to Protein Engineering," ChemBioChem, 2009, 10, 787-798.

Alley et al., "Contribution of Linker Stability to the Activities of Anticancer Immunoconjugates," Bioconjug Chem., vol. 19, No. 3, pp. 759-765, (2008); DOI: 10.1021/bc7004329; Abstract Only—1 page.

Chudasama et al., "Semi-Mechanistic Population Pharmacokinetic Model of Multivalent Trastuzumab Emtansine in Patients with Metastatic Breast Cancer," Clinical Pharmacology & Therapeutics, vol. 92, No. 4, pp. 520-527, (2012); DOI: 10.1038/clpt.2012.153; Abstract Only—2 pages.

Extended European Search Report, EP 15786402.6 dated Nov. 10, 2017.

International Search Report PCT/CN2015/077887 dated Aug. 28, 2015.

JP 2016-563404 Office Action dated Feb. 5, 2019.

Kornberger et al. ("Kornberger", *mAbs*. 2014, 2, 354-366, published online Dec. 9, 2013). (2013).

Lyon et al., "Self-Hydrolyzing Maleimides Improve the Stability and Pharmacological Properties of Antibody-Drug Conjugates," Nat Biotechnol., vol. 32, No. 10, pp. 1059-1062, (2014); DOI: 10.1038/nbt.2968; Abstract Only—1 page.

Madej et al.. "Engineering of an anti-epidermal growth factor receptor antibody to single chain format and labeling by Sortase A-mediated protein ligation" *Biotechnology and Bioengineering*, vol. 109, No. 6, Jun. 1, 2012, pp. 1461-1470.

Ponte et al., "Understanding How the Stability of the Thiol-Maleimide Linkage Impacts the Pharmacokinetics t>f Lysine-Linked Antibody-Mayansinoin Conjugates", *Bioconjugate Chemistry*, vol. 27, No. 7, Jul. 20, 2016, pp. 1588-1598.

Sauer et al. "Clickable Tyrosine Binding Bifunctional Linkers for Preparation of DNA-Protein Conjugates" *Bioconjugate Chemistry*, vol. 24, No. 6, Jun. q9, 2013, pp. 1094-1101.

Shen et al. "Conjugation site modulates the in vivo stability and therapeutic activity of antibody-drug conjugates" *Nature Biotechnology*, vol. 3, No. 2, Jan. 22, 2012, pp. 184-189.

Swee et al. "Sortase-mediated modification of alpha DEC205 affords optimization of antigen presentation and immunization against a set of viral epitodes", *Proceedings National Academy of Sciences PNAS*, vol. 110, No. 4, Jan. 22, 2013, pp. 1428- 1433.

Tumey et al. "Tumey" *Bioconjugate Chem*, 2014, 25, 1871-1880 (2014).

Tsakiji et al. "Sortase-Mediated Ligation: A Gift from Gram-Positive Bacteria to Protein Engineering" *ChemBioChem—A European Journal of Chemical Biology*, vol. 10, No. 5, Mar. 23, 2009. pp. 787-798.

* cited by examiner

SEQUENCE LISTING

```
<160> NUMBER OF SEQ ID NOS: 23

<210> SEQ ID NO 1
<211> LENGTH: 222
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation         SEQ ID No. 1:
      T-LCCTL-HC: Light chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ala Leu Pro Glu Thr Gly Gly
    210                 215                 220

<210> SEQ ID NO 2
<211> LENGTH: 450
<212> TYPE: PRT
<213> ORGANISM: Artificial
<220> FEATURE:
<223> OTHER INFORMATION: engineered anti-ErbB2/HER2 antibody based on
```

Herceptin/Trastuzumab transformation    SEQ ID No. 1:
T-LCCTL-HC: Heavy chain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 3
<211> LENGTH: 214
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation       SEQ ID No. 2:
      T-LC-HCCT: Light chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 456
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation       SEQ ID No. 2:
      T-LC-HCCT: Heavy chain

<400> SEQUENCE: 4

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
                    420                 425                 430
Glu Ala Leu His Asn His Tyr Thr Gln Lys Ser Leu Ser Leu Ser Pro
            435                 440                 445
Gly Lys Leu Pro Glu Thr Gly Gly
        450                 455
```

<210> SEQ ID NO 5
<211> LENGTH: 214
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation      SEQ ID No. 3:
      T-LC-HCCTL: Light chain

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 6
<211> LENGTH: 458
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation      SEQ ID No. 3:
      T-LC-HCCTL: Heavy chain

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

Gly Lys Gly Ala Leu Pro Glu Thr Gly Gly
    450                 455

<210> SEQ ID NO 7
<211> LENGTH: 220
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation      SEQ ID No. 4:
      T-LCCT-HC: Light chain

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Leu Pro Glu Thr Gly Gly
    210                 215                 220

<210> SEQ ID NO 8
<211> LENGTH: 450
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation      SEQ ID No. 4:
      T-LCCT-HC: Heavy chain

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val

```
                50                  55                  60
Lys Gly Arg Phe Thr Ile Ser Ala Asp Thr Ser Lys Asn Thr Ala Tyr
65                   70                  75                  80

Leu Gln Met Asn Ser Leu Arg Ala Glu Asp Thr Ala Val Tyr Tyr Cys
                    85                  90                  95

Ser Arg Trp Gly Gly Asp Gly Phe Tyr Ala Met Asp Tyr Trp Gly Gln
                100                 105                 110

Gly Thr Leu Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 9
```

```
<211> LENGTH: 220
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation     SEQ ID No. 5:
      T-LCCT-HCCT: Light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Leu Pro Glu Thr Gly Gly
    210                 215                 220

<210> SEQ ID NO 10
<211> LENGTH: 456
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation     SEQ ID No. 5:
      T-LCCT-HCCT: Heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Leu Pro Glu Thr Gly Gly
    450                 455

<210> SEQ ID NO 11
<211> LENGTH: 220
<212> TYPE: PRT
<213> ORGANISM: Artificial
<220> FEATURE:
<223> OTHER INFORMATION: engineered anti-ErbB2/HER2 antibody based on
```

-continued

Herceptin/Trastuzumab transformation  SEQ ID No. 6:
T-LCCT-HCCTL: Light chain

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Leu Pro Glu Thr Gly Gly
    210                 215                 220

<210> SEQ ID NO 12
<211> LENGTH: 458
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation  SEQ ID No. 6:
      T-LCCT-HCCTL: Heavy chain

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Ala Leu Pro Glu Thr Gly Gly
    450                 455

<210> SEQ ID NO 13
<211> LENGTH: 222
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation     SEQ ID No. 7:
      T-LCCTL-HCCT: Light chain

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Ala Leu Pro Glu Thr Gly Gly
            210                 215                 220

<210> SEQ ID NO 14
<211> LENGTH: 456
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation     SEQ ID No. 7:
      T-LCCTL-HCCT: Heavy chain

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
```

```
                130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys Leu Pro Glu Thr Gly Gly
    450                 455

<210> SEQ ID NO 15
<211> LENGTH: 222
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation         SEQ ID No. 8:
      T-LCCTL-HCCTL: Light chain

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30
```

-continued

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Ala Leu Pro Glu Thr Gly Gly
            210                 215                 220

<210> SEQ ID NO 16
<211> LENGTH: 458
<212> TYPE: PRT
<213> ORGANISM: Artificial
<220> FEATURE:
<223> OTHER INFORMATION: engineered anti-ErbB2/HER2 antibody based on
      Herceptin/Trastuzumab transformation        SEQ ID No. 8:
      T-LCCTL-HCCTL: Heavy chain

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
    195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Glu Glu Met Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys Gly Ala Leu Pro Glu Thr Gly Gly
    450                 455

<210> SEQ ID NO 17
<211> LENGTH: 6
<212> TYPE: PRT
<213> ORGANISM: Artificial Sequence
<220> FEATURE:
<223> OTHER INFORMATION: Recognition sequence of ligase
<220> FEATURE:
<221> NAME/KEY: MISC_FEATURE
<222> LOCATION: (3)..(3)
<223> OTHER INFORMATION: X in 3 position: any amino acid that is natural
      or unnatural

<400> SEQUENCE: 17

Leu Pro Xaa Thr Gly Gly
1               5

<210> SEQ ID NO 18
<211> LENGTH: 5
<212> TYPE: PRT
```

```
<213> ORGANISM: Artificial Sequence
<220> FEATURE:
<223> OTHER INFORMATION: Recognition sequence of ligase
<220> FEATURE:
<221> NAME/KEY: MISC_FEATURE
<222> LOCATION: (3)..(3)
<223> OTHER INFORMATION: X in 3 position: any amino acid that is natural
      or unnatural

<400> SEQUENCE: 18

Leu Pro Xaa Thr Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Recognition sequence of ligase

<400> SEQUENCE: 19

Asn Pro Gln Thr Asn
1               5

<210> SEQ ID NO 20
<211> LENGTH: 5
<212> TYPE: PRT
<213> ORGANISM: Artificial Sequence
<220> FEATURE:
<223> OTHER INFORMATION: Recognition sequence of ligase

<400> SEQUENCE: 20

Asn Pro Lys Thr Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Recognition sequence of ligase
<220> FEATURE:
<221> NAME/KEY: MISC_FEATURE
<222> LOCATION: (3)..(3)
<223> OTHER INFORMATION: X in 3 position: any amino acid that is natural
      or unnatural

<400> SEQUENCE: 21

Leu Ala Xaa Thr Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Recognition sequence of ligase

<400> SEQUENCE: 22

Leu Pro Gln Thr Ser Glu Gln
1               5

<210> SEQ ID NO 23
<211> LENGTH: 6
<212> TYPE: PRT
<213> ORGANISM: Artificial Sequence
<220> FEATURE:
<223> OTHER INFORMATION: Recognition sequence of ligase
```

```
<400> SEQUENCE: 23

Leu Pro Glu Thr Gly Gly
1               5
```

STABLE ANTIBODY-DRUG CONJUGATE, PREPARATION METHOD THEREFOR, AND USE THEREOF

CROSS REFERENCE TO RELATED APPLICATIONS

This application is a continuation application of U.S. application Ser. No. 15/307,738, which was filed on Oct. 28, 2016, which is a U.S. National Stage Application under 35 U.S.C. § 371 of International Application No. PCT/CN2015/077887, filed on Apr. 29, 2015, which claims the benefit of Chinese Patent Application No. 201410174890.8, filed on Apr. 29, 2014, the contents of each of which are incorporated herein by reference.

Reference to an Electronic Sequence Listing

The contents of the electronic sequence listing (2023-07-24-GQH-02-USC- SequenceListing ST25.txt; Size: 51,443 bytes; and Date of Creation: Ju. 24, 2023) is herein incorporated by reference in its entirety.

TECHNICAL FIELD

The present invention belongs to the field of bio-pharmaceutical and biotechnological field, particularly relates to a new linker (also called a coupling agent) with a coupling function, a new linker-cytotoxin intermediate with a stable ring-open structure and its preparation method thereof, and its use in the coupling of small molecules, nucleic acids, nucleic acid analogues, tracer molecules etc. to the C-terminus of proteins and peptides in a site-specific manner. The linkers and the coupling methods of the present invention can be used in the preparation of ADCs for tumor targeting therapy, targeted tracer diagnostic reagents and highly efficient delivery reagent for specific cell types. The ADC prepared according to the present invention has a stable ring-open structure, a particular drug loading and reproducible pharmacokinetic data. This provides fundamental solutions to the two major problems of the current ADCs: stability and heterogeneity. In particular, it is related to a new anti-human ErbB2/Her2 antibody-maytansine derivative conjugate, a new anti-human ErbB2/Her2 antibody-Auristatin derivative conjugate, their preparation methods and use in the targeted therapy of ErbB2/Her2-positive tumors.

BACKGROUND OF THE INVENTION

Antibody-drug conjugates (ADCs) are a new generation of potent anti-tumor drugs based on monoclonal antibody, it combines the advantages of antibodies (as a targeting moiety) and traditional cytotoxic drugs (with strong cytotoxicity). In 2011, ADC Adcetris (brentuximab vedotin) was approved by the US FDA for the treatment of Hodgkin's lymphoma; in 2013 Kadcyla (ado-trastuzumab emtansine) was approved for the treatment of advanced metastatic breast cancer. By April 2015, there are approximately 50 ADC candidates in I, II or III stage clinical trials respectively.

The mechanism of ADC is as the follows: an antibody or antibody-based ligand specifically recognizes a particular antigen on the cell surface and binds to it; the complex formed was endocytosized, together with the small molecule drug; the small molecule drug is released into the cell in an appropriate active form after the antibody is hydrolyzed by proteinases or the linker is itself broken, and kills the target cells. The small molecule cytotoxic drugs used in ADC is very potent, usually 10-1000 times more potent than the first line chemotherapy drugs currently used clinically.

ADC consists of three parts: an antibody, a linker and a cytotoxin. Wherein the antibody determines the targeted cell type and site; the cytotoxin can be any compound that can cause cell death, induce cell apoptosis or reduce cell viability; and the linker is a bridge which connects the two together, thus it is the key part of an ADC design, and the key factor to realize targeted drug delivery.

There are two types of linkers employed by ADC: cleavable and non-cleavable. An ideal linker must meet the following requirements: sufficiently stable outside the cells to ensure the small-molecule drug is connected to the ligand; after entering the cell, the cleavable linker will break under appropriate conditions and release the active small molecule drugs; for the non-cleavable linker, the active component is consisting of a small molecule, a linker, and amino acid residues produced by the enzyme hydrolyzation of the ligands.

A linker connects an antibody and small molecule cytotoxins. If the cytotoxins fall-off before reaching the target, it will cause toxicity to normal tissues, and, on the other hand, it will reduce the efficiency of ADC arrived at the target. Thus, in the development of ADCs, the linker design and the related coupling strategies are critical. It not only plays a key role in the stabilization of the ADC, but also directly affects the biological activity, aggregation states, the in vivo bio-availability, distribution and metabolism of the conjugate. Most of the ADCs currently marketed and in clinical trials use linkers and coupling strategies originated from Seattle Genetics and Immunogen. These two companies used slightly different coupling strategies, but both used the sulfosuccinimide structure (thiosuccinimide linkage) formed via the reaction of a thiol group and a maleimide to connect the small molecule drugs and the targeting antibody (FIG. 1); Since this reaction is fast, quantitative and proceeds under mild conditions, it is widely used (Hermanson G T, Bioconjugate Techniques 2nd edition, 2008).

Unfortunately, the sulfosuccinimide linkage is not stable, this thiol group will reversibly exchange with other thiols in vivo (maleimide elimination reaction). Cysteine, glutathione and albumin in vivo provide high concentrations of thiol groups, which can capture the succinimide ring in the sulfosuccinimide linkage and exchange with the thiol group in the ADC. Such exchange reaction directly leads to the fall-off of the cytotoxins from the antibody in an ADC (Alley S C et al, Bioconjug Chem 2008; Shen B Q et. al, Nat Biotechnol 30, 184-189, 2012; Chudasama V L, et al., Clin. Pharmacol. Ther. 92, 520-527, 2012).

Based on previous chemical research, the sulfosuccinimide structure could be opened via hydrolysis (ring-opening hydrolysis). After ring-open, the in vivo thiol exchange reaction with sulfosuccinimide will not take place (FIG. 1, a schematic view of a ring-open reaction), thereby increasing the in vivo stability of the ADC. Conventional chemical ring opening conditions include: base treatment, molybdate treatment, etc. (Kalia J et al., 2007), but these conditions cannot be applied directly to the succinimide ring-open in ADCs, since these harsh processing conditions will cause irreversible damage to proteins (antibodies), so the above conditions cannot be applied directly to the succinimide ring-open in ADCs.

Much effort has been made to solve this problem. For example: at Genentech, they screened the antibody surface structure and evaluate the chemical properties to find a suitable location as the cytotoxic coupling site, which will accelerate the sulfosuccinimide ring-open reaction (Shen B Q et al, Nat Biotechnol 30, 184-189, 2012); at Seattle Genetics, they use diaminopropionic acid (DPR) to introduce a basic amino at a position adjacent to maleimide in the linker, to promote fast hydrolysis of sulfosuccinimide structure in ADCs (Lyon R P et al, Nat Biotechnol 2014 October; 32 (10): 1059-62; US2013/0309256 A1); at Pfizer, they used a mild alkaline borate buffer to promote hydrolysis of sulfosuccinimide structure (Tumey L N, et al, Bioconjugate Chem 2014, (25):1871-1880). The above strategies can all promote the hydrolysis of the sulfosuccinimide structure for a certain degree, thereby stabilizing ADCs, but they all face the same problem: the hydrolysis process must be carried out after the antibody-cytotoxin coupling, which makes the pharmaceutical preparation process of ADC more complicated with an additional ring opening step, and increases the risk of antibody damage and inactivation; more importantly, due to the hydrolysis process is carried out after the cytotoxin-antibody conjugation, the hydrolysis degree of the sulfosuccinimide structure cannot be accurate controlled, making the quality control standard difficult to set up.

However, the improved strategies above are only applicable to those using cysteines of antibody as the conjugation sites. As for those using antibody lysines as coupling sites, and the cytotoxin has a reactive thiol group(s) (for example, the marketed drug Kadcyla, using Immunogen's DM1 molecules and the corresponding SMCC linker), the cytotoxin can easily be replaced by the thiol group of abundant cysteine, glutathione and albumin in vivo. Currently, there is no effective way to actively promote ring opening reaction of sulfosuccinimide, and thus the break-off of cytotoxin in vivo is out of control, leaving a potential risk for drug safety.

The current mainstream conjugation technology is chemical coupling strategy mainly based on the lysine or cysteine residues in the antibody. Due to the diversity in number and location of these amino acids in antibody which can react with linkers, the number and location of the cytotoxins in the ADCs are variable, and ADCs thus obtained are heterogenous. This heterogeneity will affect the quality, stability, effectiveness, metabolism and toxicity of ADCs. For example, in the drug instruction of Kadcyla, an ADC which was marketed in 2013, it clearly indicated that the number of cytotoxins in each antibody is between 0 and 8, the average n is about 3.5. To solve the problem of heterogeneity of ADCs has become the main task and a big challenge in the development of a new generation of ADCs.

ErbB2/Her2 antigen, which is a member of the mammal (including human) epidermal growth factor receptor transmembrane receptor family, is over-expressed in about 20% of breast cancer and 16% of gastric cancer cell surface (Slamon et al. 1987, Science, Vol 235: 177-182). Humanized monoclonal antibody of Trastuzumab (tradename Herceptin) can selectively bind to the extracellular region of human ErbB2/Her2 antigen with high affinity (Kd=5 nM), inhibiting tumor cell proliferation and growth (Hudziak et al. 1989, Mol. Cell Biol, Vol 9: 1165-1172; Lewis et al. 1993, Cancer Immuno Immunother, Vol 37: 255-263; Baselga et al. 1998, Cancer Res, Vol 58:2825-2831). Herceptin showed more significant effects than chemotherapy alone when being used to treat ErbB2/Her2 positive patients and achieved a great commercial success. However, with the widely use of Herceptin, problem has gradually come out that some patients have less or non-response to the treatment.

SUMMARY OF THE INVENTION

This invention relates to a novel coupling functional linker (also referred to as coupling agent), a linker-payload intermediate, the ring-opening reaction thereof and the preparation method thereof. The present invention also relates to a conjugate formed by coupling of the C-terminus of proteins and peptides to linker-payload intermediate in a site-specific manner, and the preparation method thereof. The present invention further relates to a pharmaceutical composition comprising the conjugate. The present invention also relates to the use of the conjugate or the pharmaceutical composition comprising the conjugate in the treatment or prevention of a disease.

In one aspect, the present invention provides a compound of Formula (I), (II), (III) or (IV):

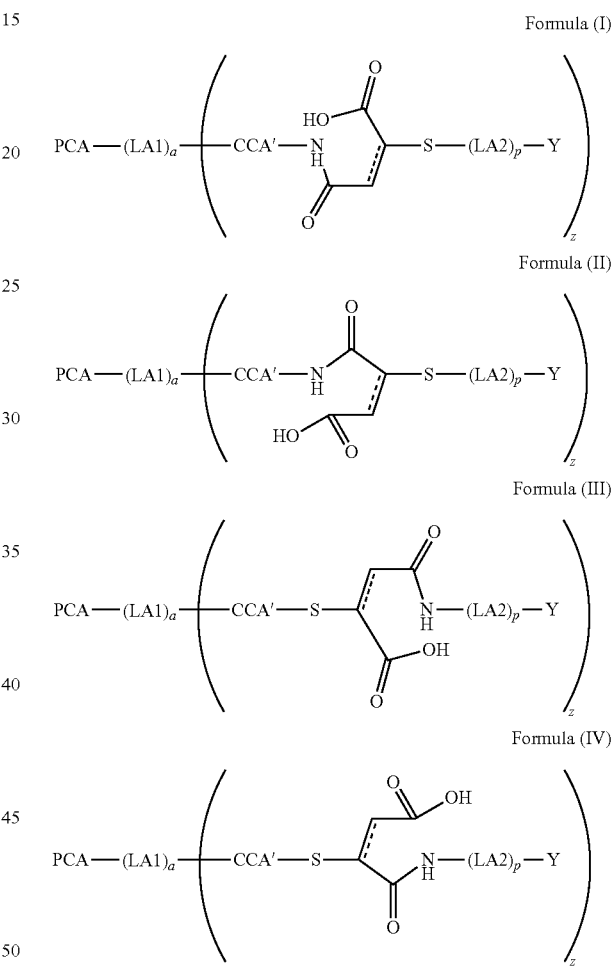

or a pharmaceutically acceptable salt thereof.

Wherein, PCA is a specific substrate recognition sequence of the ligase. The said ligase is capable of linking two molecules by forming a new chemical bond. In some embodiments, the ligase is a transpeptidase, including, but not limited to, various natural Sortases and those modified and optimized new transpeptidases. In some embodiments, the Sortase is Sortase A or Sortase B. In some embodiments, PCA is a specific recognition sequence of the ligase receptor substrate. In some embodiments, PCA comprises at least one series-connected structure units which are selected from the group consisting of one or more glycine and alanine. In certain embodiments, PCA comprises 1 to 100 series-connected structure units which are selected from the group consisting of one or more glycine and alanine. Preferably, PCA comprises 1 to 50 s series-connected structure units which are selected from the group consisting of one or more glycine and alanine. More preferably, PCA comprises 1 to 20 series-connected structure units which are selected from the group consisting of one or more glycine and alanine. More preferably, PCA comprises 5 series-connected structure units which are selected from the group consisting of one or more glycine and alanine. More preferably, PCA comprises 3 series-connected structure units which are selected from the group consisting of one or more glycine and alanine.

LA1, LA2 are linker moieties, a and p are independently 0 or 1, that is, LA1 and LA2 are independently present or absent. LA1 is the linkage between PCA and CCA', LA2 is the linkage between the —S— group and Y. CCA' is a chemical conjugation moiety. ----- represents a single or double bond. In certain embodiments, ----- represents a single bond.

Y is a payload, which is selected from the group consisting of a nucleic acid sequence, a short peptide sequence, a polypeptide, a protein, a small molecule and a biological substance. In certain embodiments, Y is a nucleic acid sequence, a nucleic acid analogue, a marker, a label or a drug. In certain embodiments, Y is a radioactive label, a fluorescent label, an affinity purification tag, a tracer molecule or small molecule. In certain embodiments, Y is a cytotoxin. In certain embodiments, Y is maytansine or a derivative thereof, Auristatin or a derivative thereof, epothilone or an analogue thereof, paclitaxel or a derivative thereof, or a vinca alkaloid compound. In certain embodiments, Y is maytansine or a derivative thereof.

z is any of the integers between 1 and 1000. Preferably, z is any of the integers between 1 and 100, between 1 and 50, between 1 and 40, between 1 and 30, between 1 and 20, between 1 and 10, or between 1 and 5.

In certain embodiments, the present invention provides a compound of the formula:

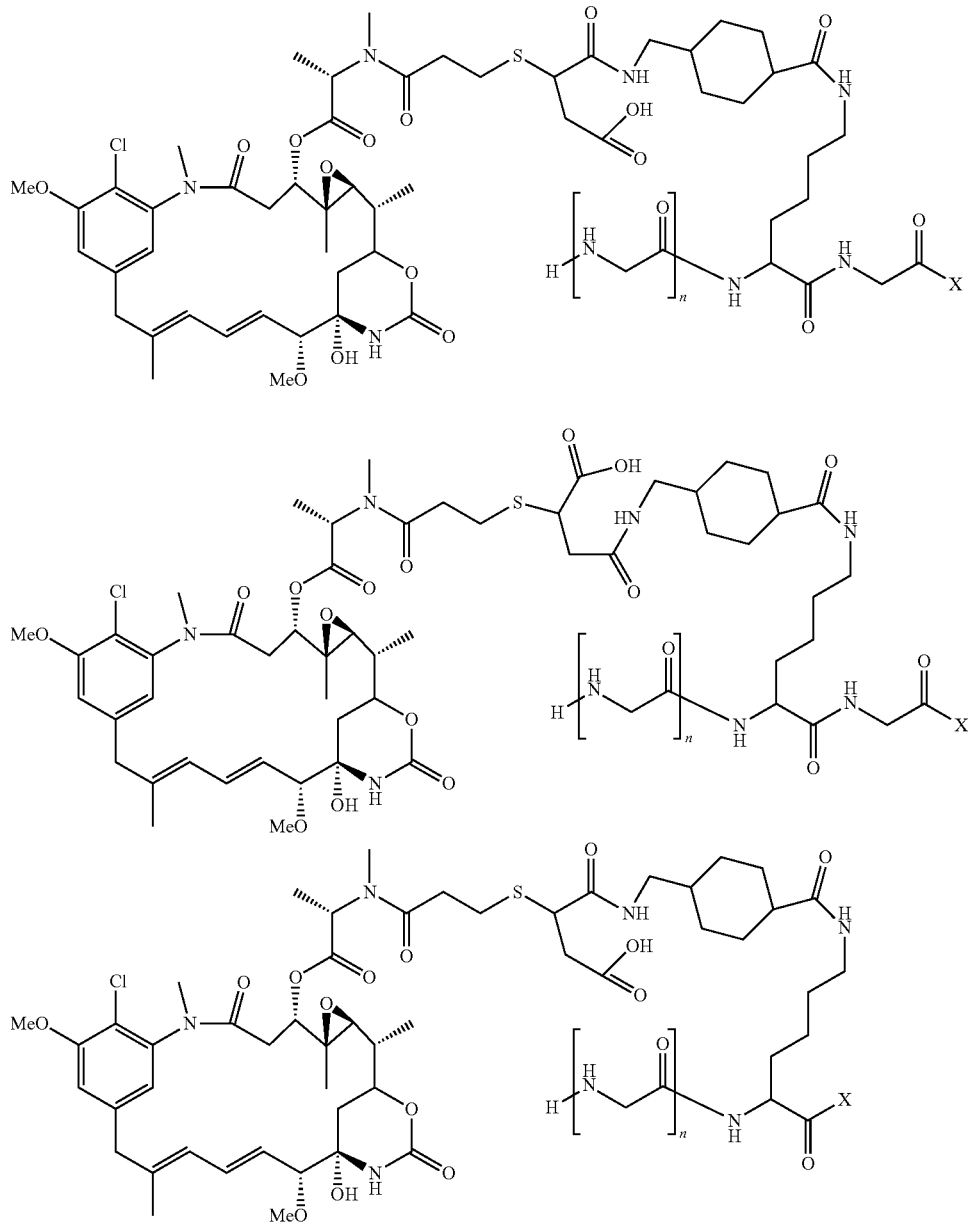

-continued
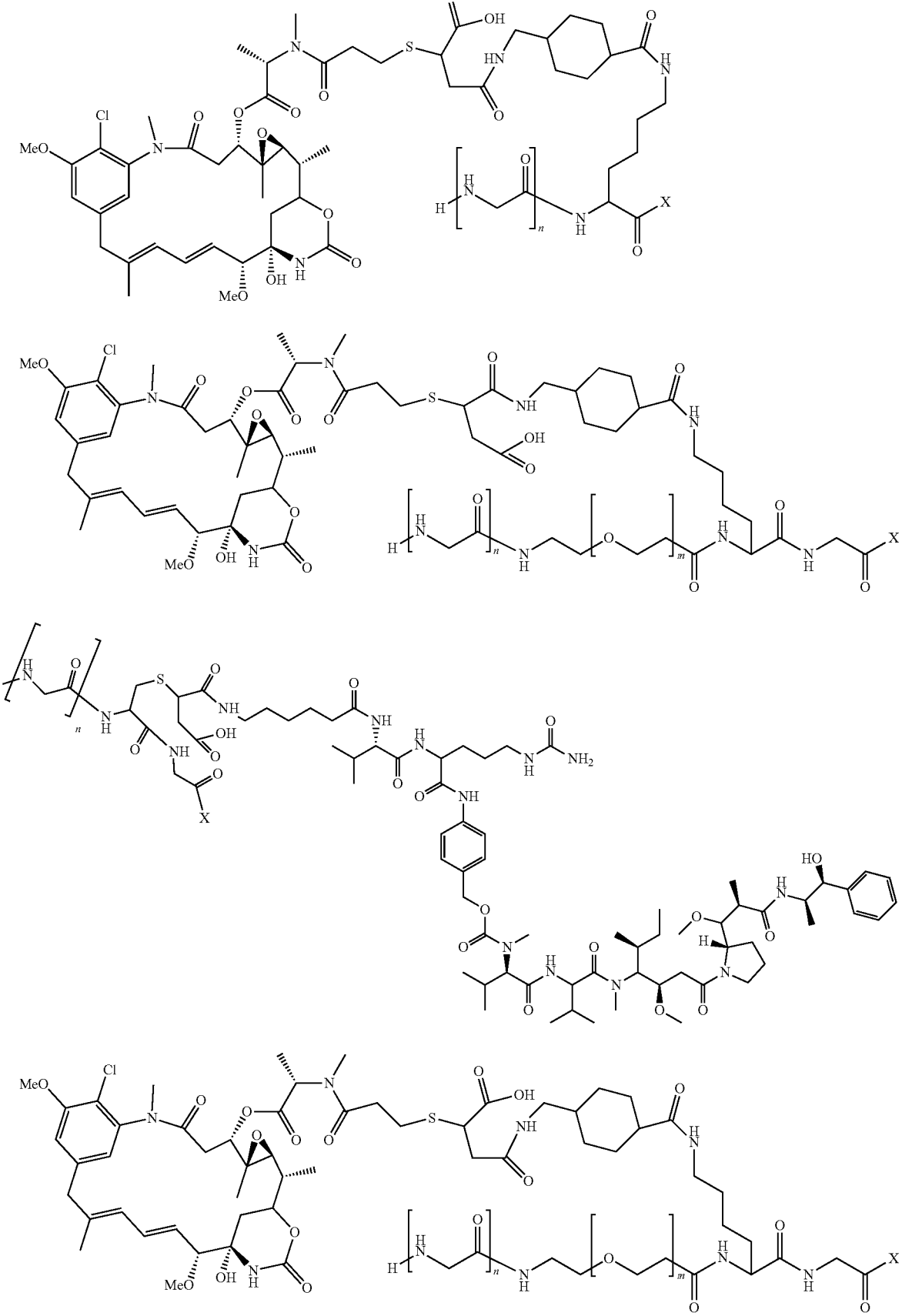

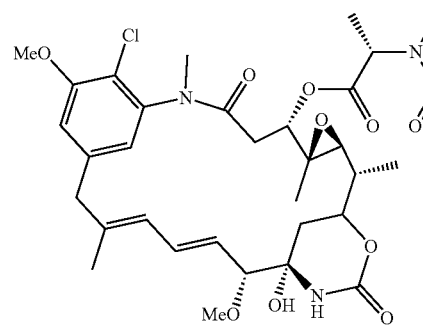
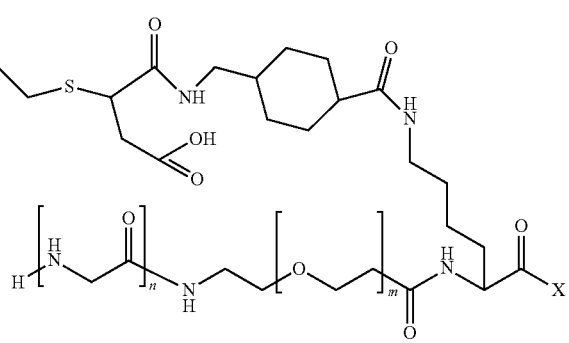
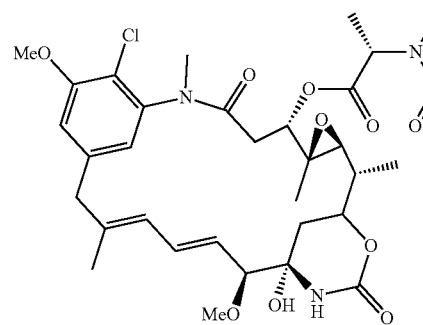
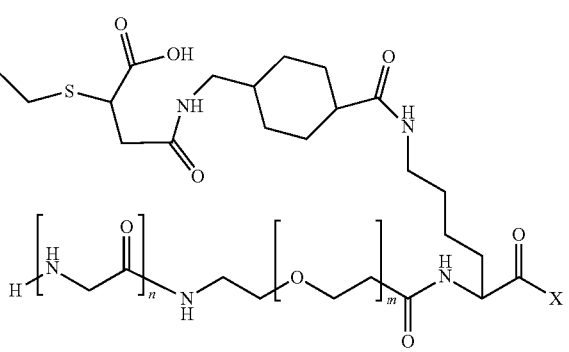
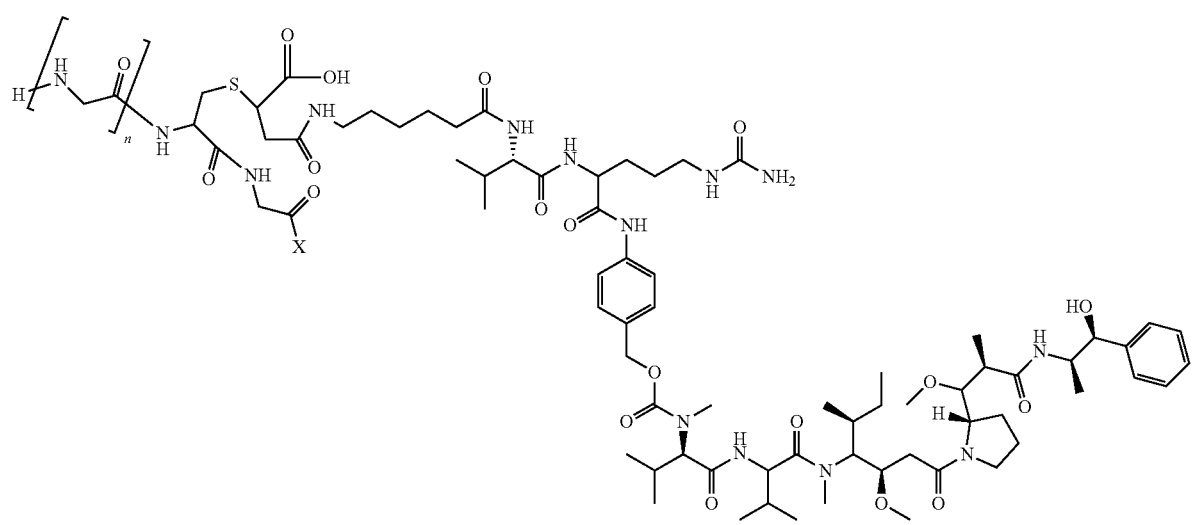

-continued
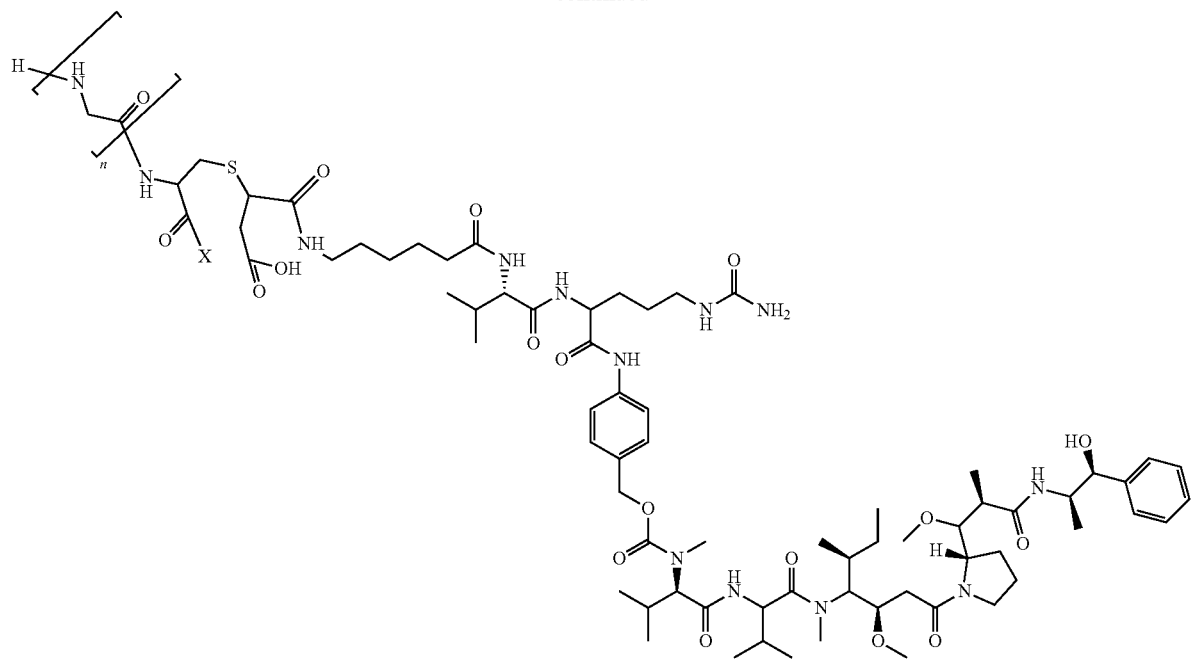
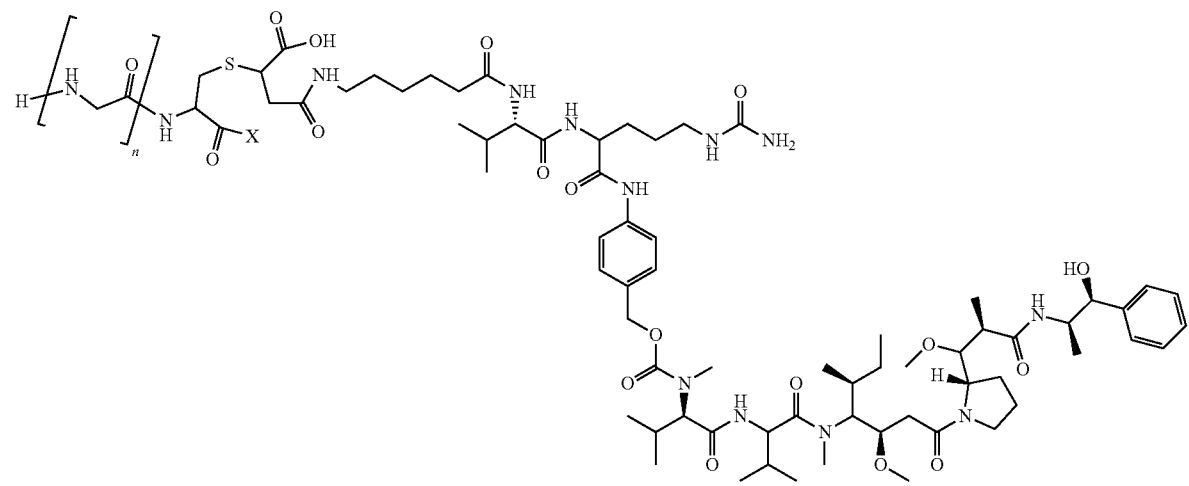
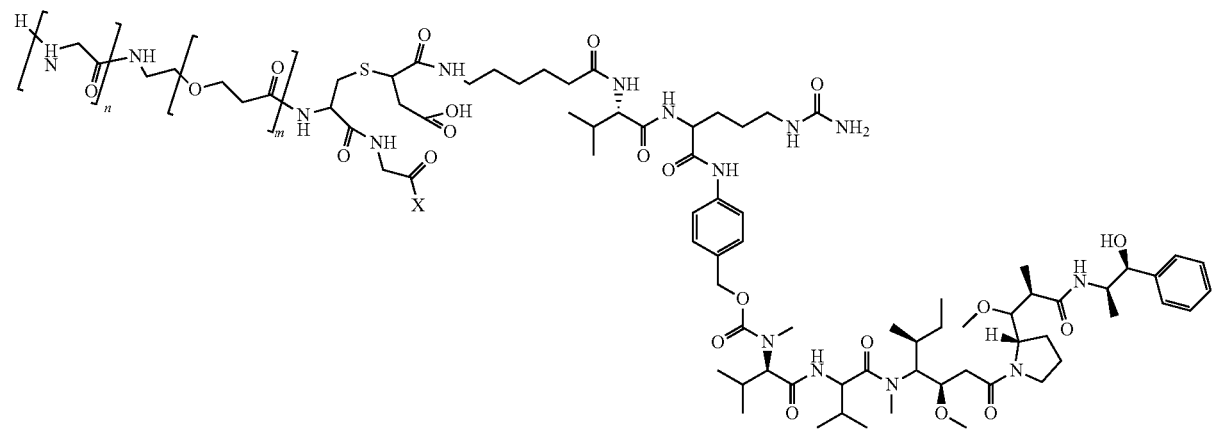

-continued
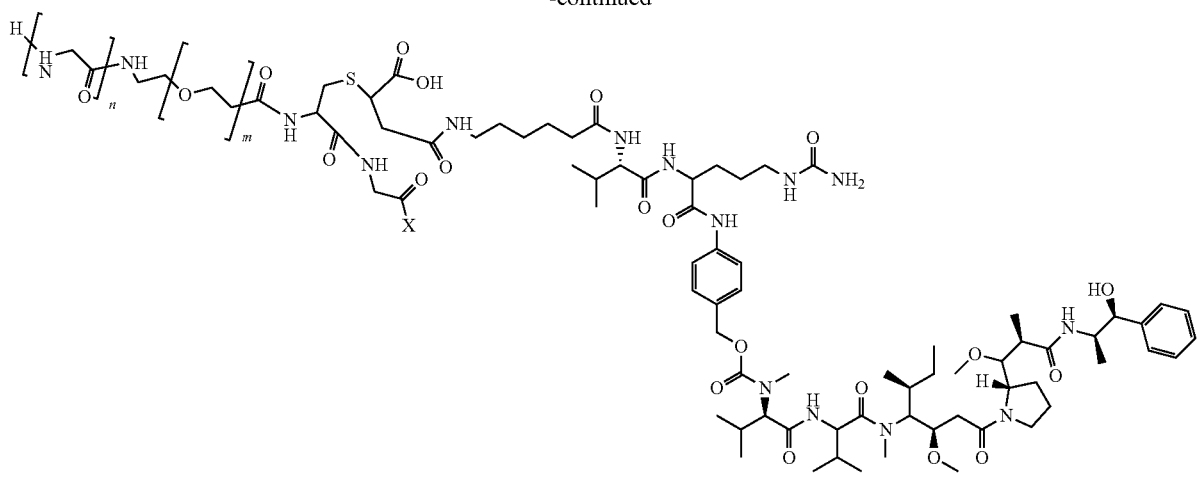
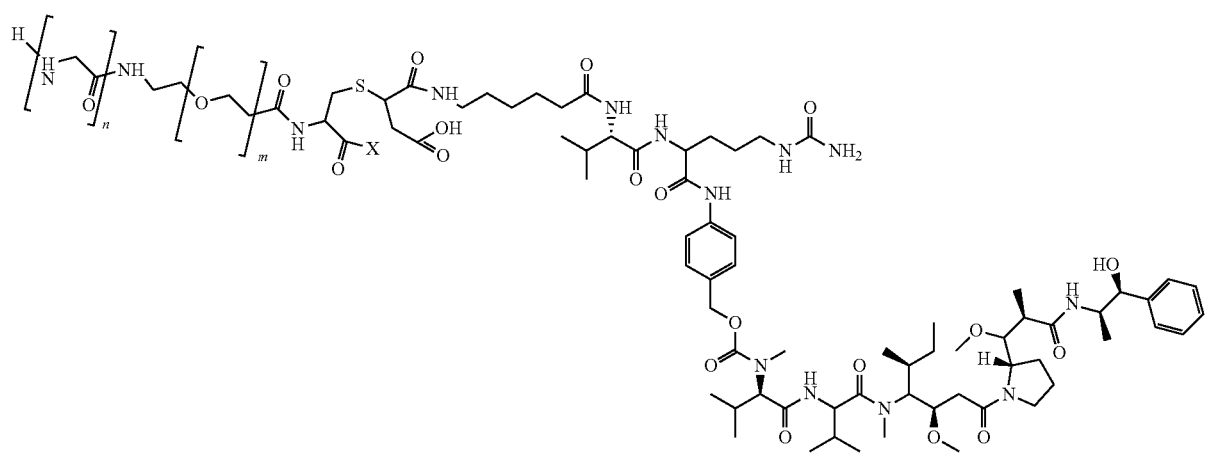
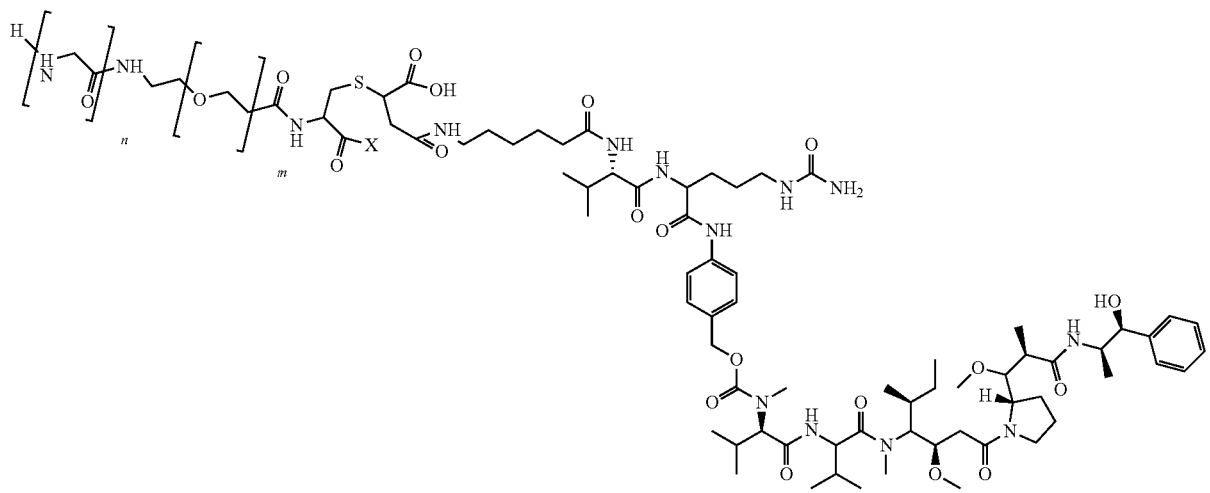

Wherein n represents any of the integers between 1 and 100, for example, n may be 1, 2, 3, 4, 5, 6, 7, 8, 9, 10, 15, 20 or the like. m is 0 or any of the integers between 1 and 1000, for example, m may be 1, 2, 3, 4, 5, 6, 7, 8, 9, 10, 20, 30, 40, 50, 60, 70, 80, 90, 100 or the like.

In another aspect, the present invention provides a composition comprising one or more of the above-described compounds, which is prepared by the following steps:

A) a solution of Y and a solution of

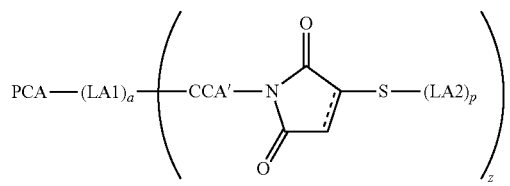

are mixed and incubated to obtain a solution of conjugate:

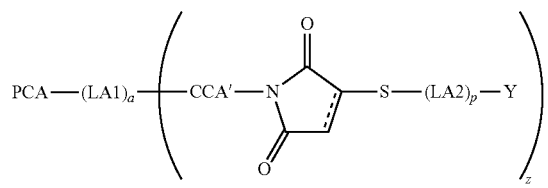

or
a solution of Y and a solution of

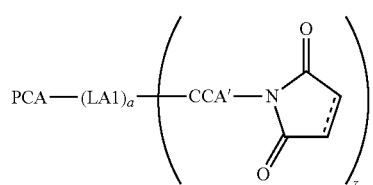

are mixed and incubated to obtain a solution of the conjugate

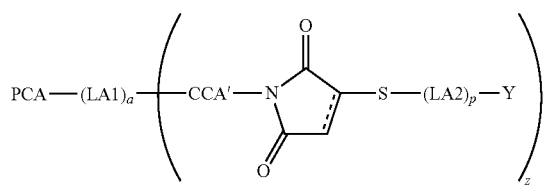

in this case, a —S-(LA2)$_p$ group is connected to Y;
or
a solution of Y and a solution of

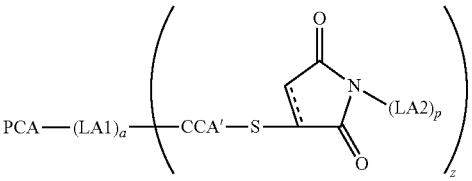

are mixed and incubated to obtain a solution of

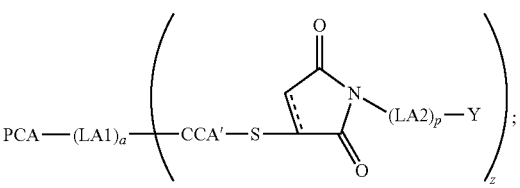

or
a solution of Y and a solution of

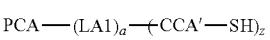

are mixed and incubated to obtain a solution of conjugate

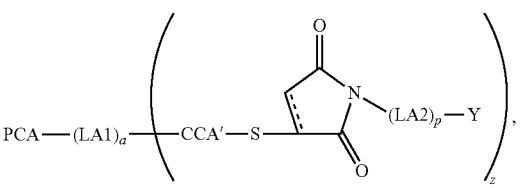

in this case, a

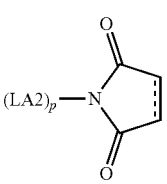

group is connected to Y;

B) to a solution of the conjugate

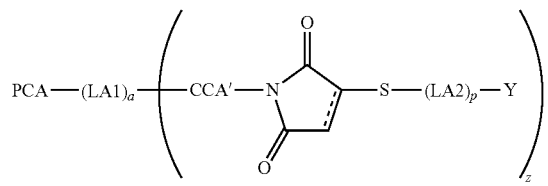

or

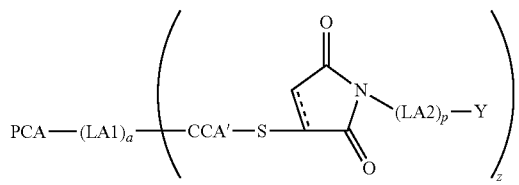

prepared in A) is added a Tris base solution or other solution which facilitates ring-open.

In certain embodiments, the above-described step further comprises purifying the obtained product by HPLC. In certain embodiments, the above-described step further comprises purifying the obtained product by semi-preparative/preparative HPLC. In certain embodiments, the total molar content of the compounds of Formula (I), (II), (III) or (IV) is more than 50%, e.g. more than 60%, 70%, 80%, 85%, 90%, 95%, 99% or more.

In another aspect, the present invention also provides a compound of Formula (V), (VI), (VII) or (VIII):

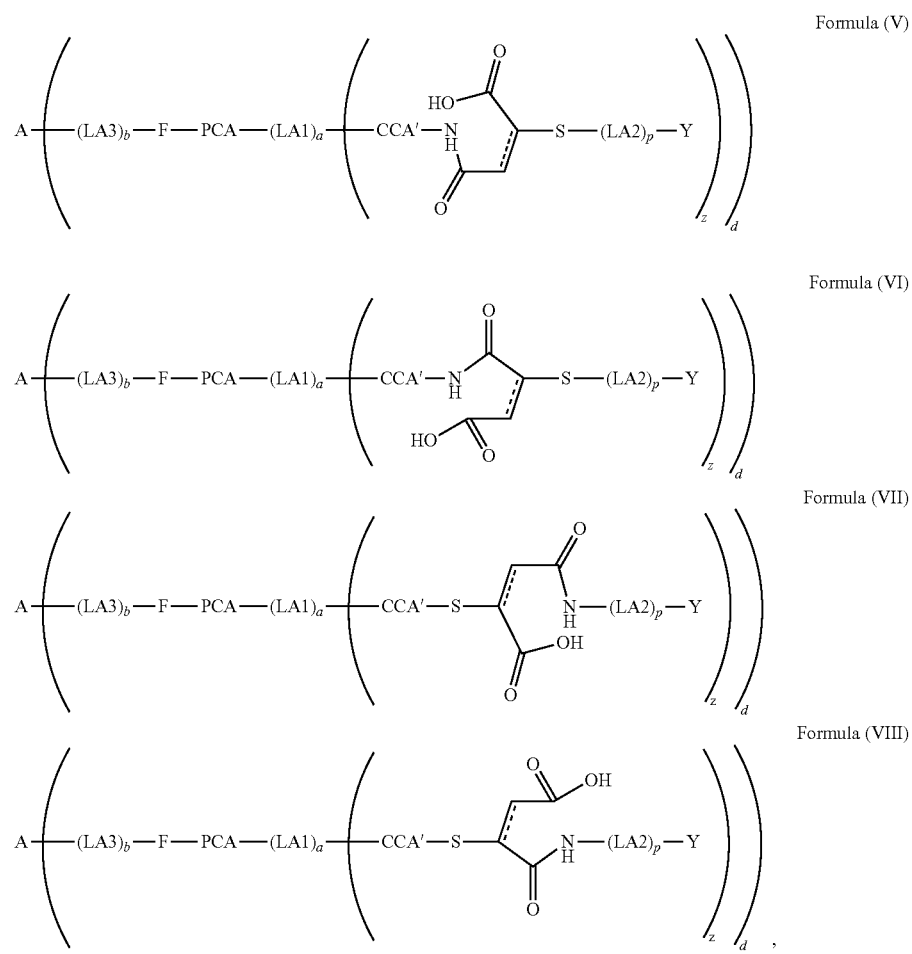

or its pharmaceutically acceptable salt thereof.

Wherein, A is a protein, a peptide, a signal transduction factor, a cell growth factor, an immunoglobulin or an antibody. In certain embodiments, the antibody is a recombinantly prepared monoclonal antibody, chimeric antibody, humanized antibody, antibody fragment and antibody mimic (e.g., Fab, ScFv, minibody, diabody, nanobody, etc.). In certain embodiments, A is an anti-ErbB2/Her2 antibody. In certain embodiments, the compound of Formula (V), (VI), (VII) or (VIII) can specifically bind the extracellular domain of Her2 receptor, and thus inhibit the growth of ErbB2/Her2 receptor positive tumor cells.

LA1, LA2 and LA3 are each independently a linker moiety. LA1 is a linkage between PCA and CCA', LA2 is a linkage between —S— group and Y, LA3 is a linkage between A and F. LA3 comprises 1 to 100 series-connected structure units which are selected from the group consisting of one or more glycine and alanine; preferably, LA3 comprises 1 to 50 series-connected structure units which are selected from the group consisting of one or more glycine and alanine. More preferably, LA3 comprises 1 to 20 series-connected structure units which are selected from the group consisting of one or more glycine and alanine. More preferably, LA3 comprises 5 series-connected structure units which are selected from the group consisting of one or more glycine and alanine. a, b and p are independently 0 or 1, that is, LA1, LA2 and LA3 may be independently present or absent.

PCA and F are specific recognition sequences of the ligase, respectively, by the action of said ligase the PCA can bind specifically to F. The ligases include, but not limited to, various natural Sortases and preferably modified and optimized new transpeptidases. In certain embodiments, the Sortase is Sortase A or Sortase B. In certain embodiments, F is a specific recognition sequence of the ligase donor substrate; PCA is a specific recognition sequence of the ligase receptor substrate. In certain embodiments, F is a specific recognition sequence of the ligase receptor substrate; PCA is a specific recognition sequence of the ligase donor substrate. In certain embodiments, PCA comprises at least one series-connected structure units which are selected from the group consisting of one or more glycine and alanine. In certain embodiments, PCA comprises 1 to 100 series-connected structure units which are selected from the group consisting of one or more glycine and alanine. Preferably, PCA comprises 1 to 50 series-connected structure units which are selected from the group consisting of one or more glycine and alanine. More preferably, PCA comprises 1 to 20 series-connected structure units which are selected from the group consisting of one or more glycine and alanine. More preferably, PCA comprises 5 series-connected structure units which are selected from the group consisting of one or more glycine and alanine. In certain embodiments, F is linked to the C-terminus of A's heavy or light chain through LA3 or directly through a covalent bond. In certain embodiments, F is $X_1X_2X_3TX_4X_5$, with $X_1$ being leucine or asparagine, $X_2$ being proline or alanine, $X_3$ being any of the natural or unnatural amino acids, T being threonine, $X_4$ representing glycine, serine or asparagine or being absent, and $X_5$ being any of the natural or unnatural amino acid or being absent. In certain embodiments, F is $LPX_3T$ or $LPX_3TGG$ (SEQ ID NO: 17), with L being leucine, P being proline, $X_3$ being any of the natural or unnatural amino acids, T being threonine and G being glycine.

CCA' is a chemical conjugation moiety. ----- represents a single or double bond. In certain embodiments, ----- represents a single bond.

Y is a payload, which is selected from the group consisting of a hydrogen, a nucleic acid sequence, a short peptide sequence, a polypeptide, a protein, a compound, and a biological substance. In certain embodiments, Y is a nucleic acid sequence, a nucleic acid analogue, a marker, a label or a drug. In certain embodiments, Y is a radioactive label, a fluorescent label, an affinity purification tag, a tracer molecule or small molecule. In certain embodiments, Y is a cytotoxin. In certain embodiments, Y is maytansine or a derivative thereof, Auristatin or a derivative thereof, epothione or an analogue thereof, paclitaxel or a derivative thereof, or a vinca alkaloid compound. In certain embodiments, Y is maytansine or a derivative thereof.

z is any of the integers between 1 and 1000. Preferably, z is any of the integers between 1 and 100, between 1 and 50, between 1 and 40, between 1 and 30, between 1 and 20, between 1 and 10, between 1 and 5. d is any of the integers between 1 and 20, for example, d may be 1, 2, 3, 4, 5, 6, 7, 8, 9, 10, 11, 12, 13, 14, 15, 16, 17, 18, 19, 20 or the like.

In certain embodiments, the present invention provides a compound of any of the following formula:

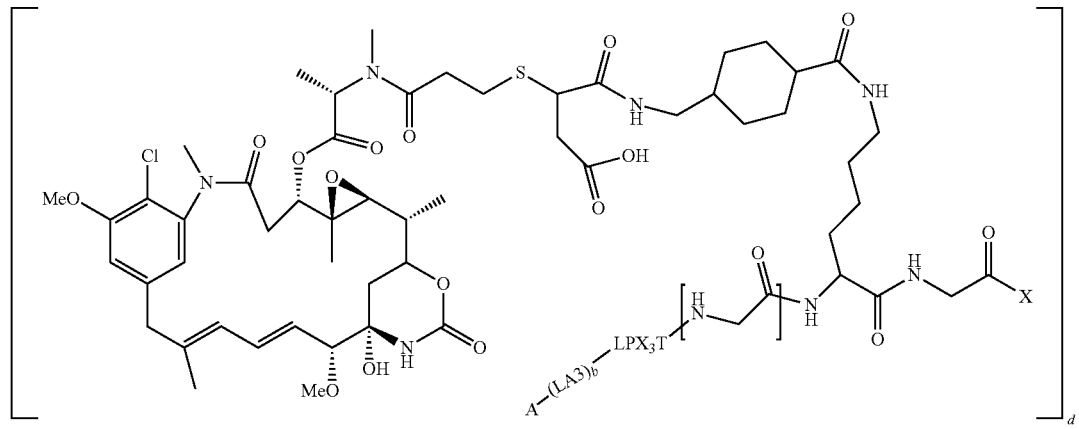

21
22
-continued
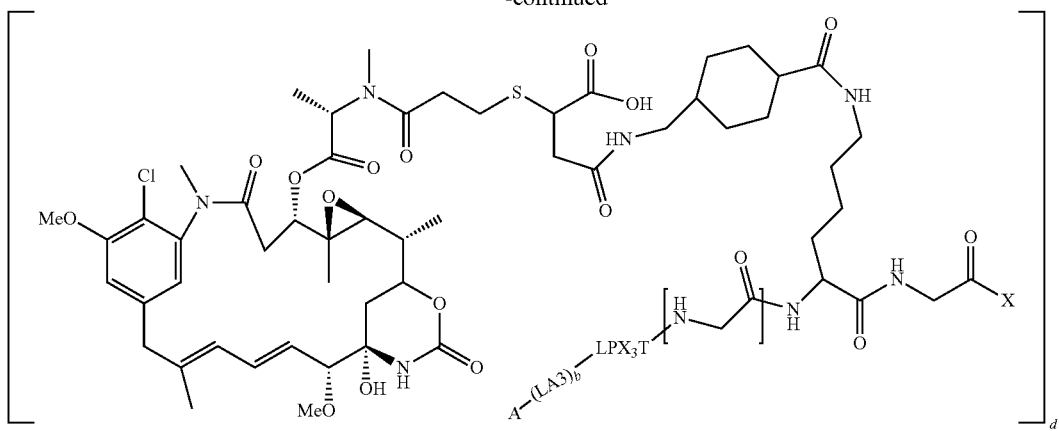
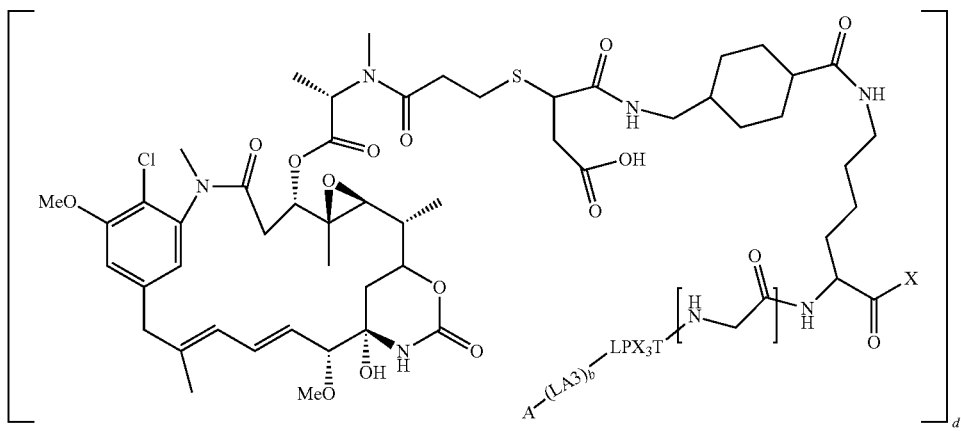
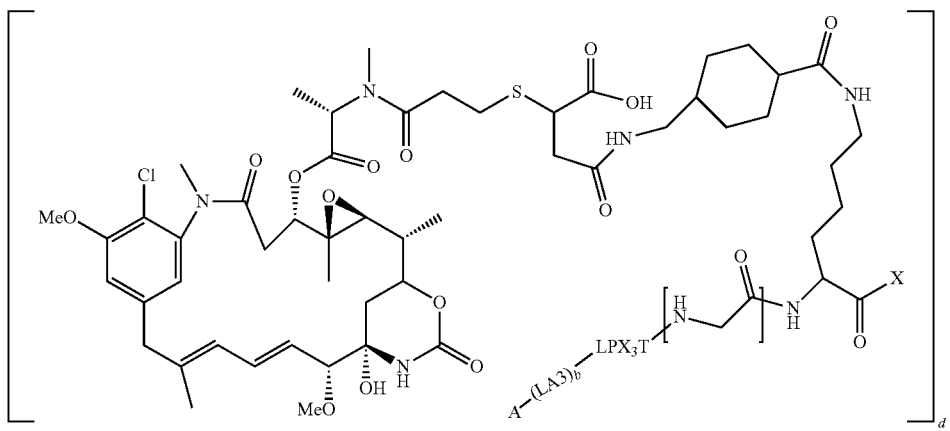

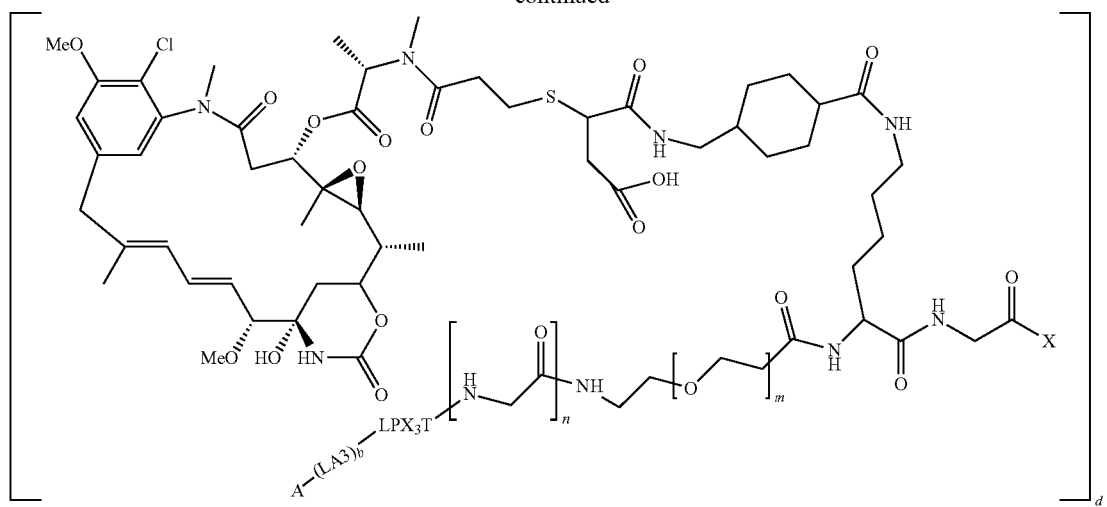
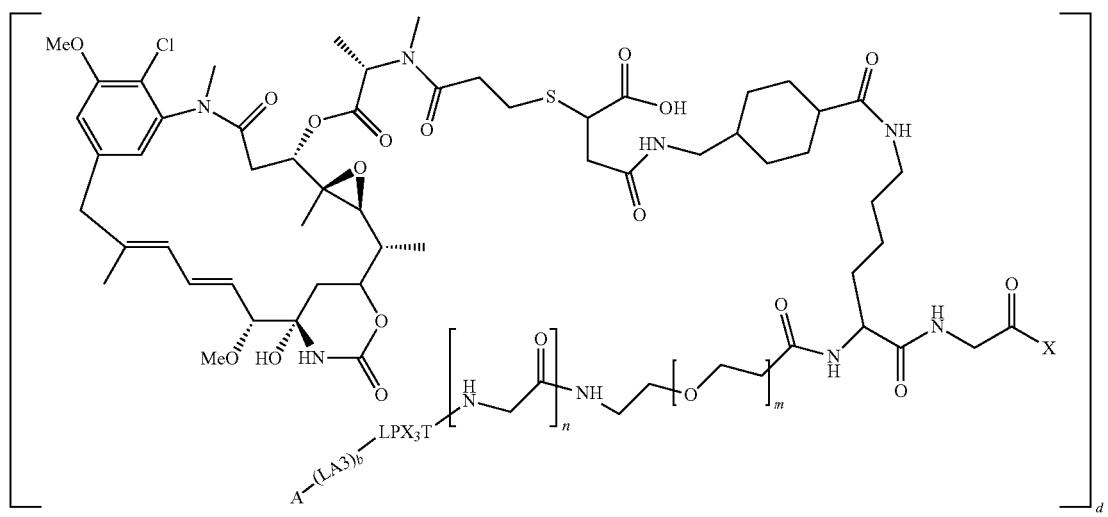
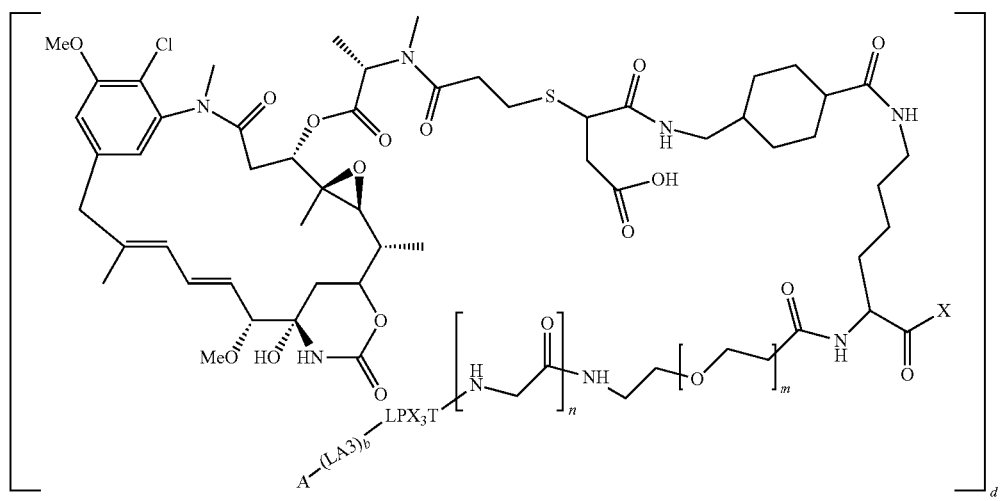

-continued
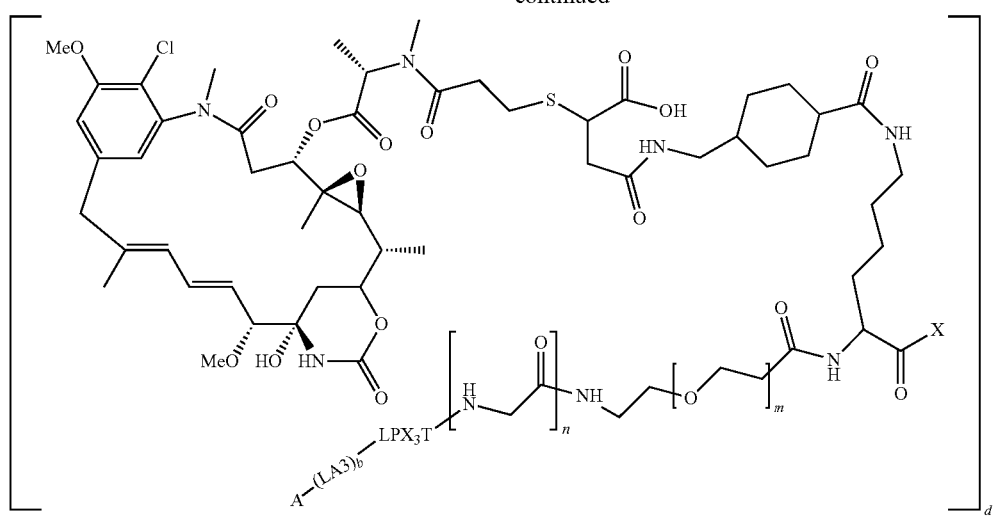
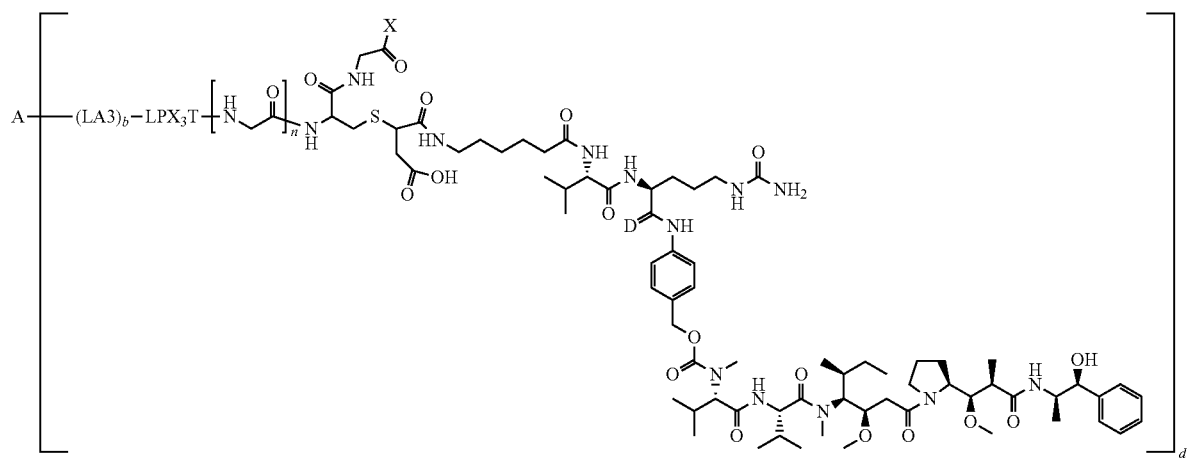
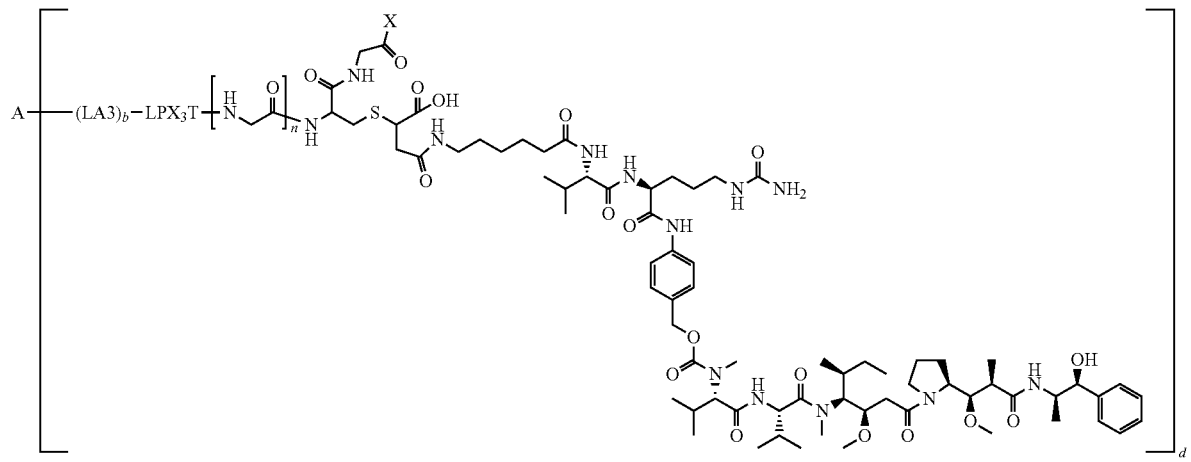

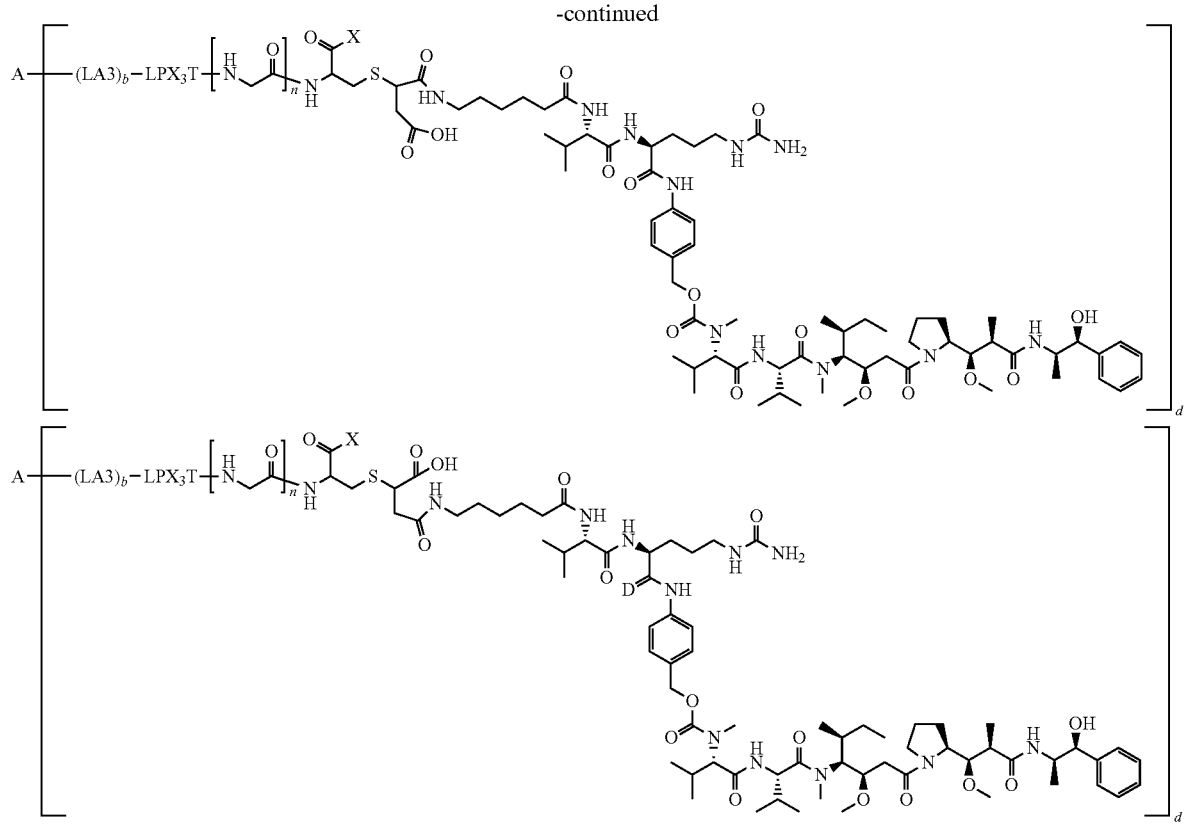

Wherein Ab is any of the sequences of SEQ ID NOs: 1-8, z represents any of the integers between 1 and 20, n represents any of the integers between 1 and 100, m is 0 or any of the integers between 1 and 1000, d represents any of the integers between 1 and 20, LA3 comprises 1 to 100 structural units connected in series which are selected from the group consisting of one or more glycine and alanine; b is independently 0 or 1, that is, LA3 can be independently present or absent.

In another aspect, the present invention provides a composition comprising any of the above compounds, which is prepared by the following steps:

i) a compound of Formula (I), (II), (III) or (IV) is prepared;
ii) A-$(LA_3)_b$-F is prepared;
iii) A-$(LA_3)_b$-F obtained in step ii) and a compound of Formula (I), (II), (III) or (IV) are conjugated at the presence of a ligase and under conditions suitable for action of the ligase.

In certain embodiments, the total molar content of the compounds of Formula (V), (VI), (VII) or (VIII) in a composition obtained in the steps described above, was more than 50%, e.g. more than 60%, 70%, 80%, 85%, 90%, 95%, 99% or more.

In another aspect, the present invention provides a method for inhibiting cell proliferation in an animal, including treating the animal with the compound or the composition according to the invention. In certain embodiments, the animal is a mammal. In certain embodiments, the animal is a human.

In another aspect, the present invention provides the use of the compound according to the present invention in the manufacture of a medicament for the prevention or treatment of a disease in human. In certain embodiments, the disease includes a tumor and an autoimmune disease. In certain embodiments, the tumor cell surface has a specific antigen or a receptor protein which recognizes and binds to the compound or composition. In certain embodiments, the specific antigen or the receptor protein on the tumor cell surface is ErbB2/Her2. In certain embodiments, the tumor is breast cancer, gastric cancer, ovarian cancer, lung cancer, colon cancer, rectal cancer, colorectal cancer or esophageal cancer.

In another aspect, the present invention provides a pharmaceutical composition comprising the compound of Formula (V), (VI), (VII) or (VIII) or a pharmaceutically acceptable salt thereof, and a pharmaceutically acceptable carrier. In certain embodiments, the pharmaceutical composition is in the form of lyophilized powder for injection or injection liquid.

The present invention provides an improved coupling system, to solve the instability and heterogeneity issues associated with the current ADCs. The solutions provided in this invention can also be applied to the preparation of targeting nucleic acid drugs, targeting diagnostic tracer reagents, and the like. The present invention includes a series of linkers and the preparation methods thereof, linker-payload intermediates and the preparation methods thereof, stable ring-open linker-payload intermediates and preparation methods. The present invention comprises a series of genetically engineered Herceptin-based or other anti-human ErbB2/Her2 antibodies (Ab), linkers, as well as modified maytansine and its derivatives or Auristatin derivative MMAE, and new ADCs thus obtained using our LDC platform technology, preparation methods and uses thereof.

The present invention utilizes a unique ligase catalyzed conjugation technology (Ligase dependent conjugation, LDC) to prepare ADCs, as shown in FIG. 2. The ligase herein refers to transpeptidase, including, but not limited to, various natural Sortases (including Sortase A, B, C, D, and L. plantarum Sortase, etc., see patent US20110321183A1) and a variety of optimized and modified new transpeptidases. The conjugation reaction is catalyzed by a bioenzyme and under mild conditions, significantly reduces the physical and chemical damage of the antibodies during the coupling process, making the ADC production process more optimized, easy to upgrade, and beneficial for the quality control of ADC products.

The core advantages of the LDC technology are the one-step enzyme catalyzed conjugation by means of bioenzyme catalysis, which allows the efficient coupling of the cytotoxins to the antibody in a site-specific way, ensuring the high homogeneity of ADCs drugs thus obtained. The sulfosuccinimide ring-open reaction is carried out during the preparation of the linker-cytotoxin intermediates, which does not involve the macromolecular antibody. This approach has two advantages: firstly, only small molecules are involved in the ring-opening reaction, a variety of hydrolysis conditions can thus be applied without the risk of antibody damaging; on the other hand, even if the sulfosuccinimide ring open reaction is not completed, the ring-opened product can be easily purified by HPLC to give highly purified ring-opened product.

The present invention is applicable to preparation of any ADC, target nucleic acid drug, and target tracer which comprises a sulfosuccinimide structure.

1. Linker

The present invention is related to a series of bi-functional linkers, which is composed of three parts: a Protein Conjugation moiety (PCA), a Linker moiety 1 (LA1) and a Chemical Conjugation moiety (CCA), shown in the schematic structure:

PCA-(LA1)a-CCA wherein PCA can be a suitable receptor substrate of Sortase A, including but not limited to oligomeric glycine (Gly) sequence Gn (n is typically 1-100), the α-carboxyl group of the C-terminal amino acid is used to couple with LA; wherein PCA may also be a suitable receptor substrate of other Sortase or preferably optimized Sortase, such as oligo alanine (Ala) sequence or oligo glycin/alanine mixing sequence.

LA1 is the linkage moiety between PCA and CCA, a is 0 or 1, that is, LA1 may be present or absent. The structure of LA1 is shown below:

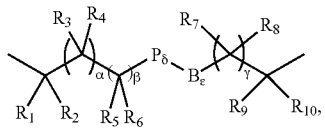

wherein R1, R2, R3, R4, R5, R6, R7, R8, R9 and R10 are the same or different, and are each independently H; a linear alkyl group having 1 to 6 carbons; a branched or cyclic alkyl group having 3 to 6 carbons; a linear, branched or cyclic alkenyl/alkynyl group having 2 to 6 carbons; a charged group selected from anionic and cationic substituted groups—the said anion is selected from SO3-, X—SO3-, OPO32-, X—OPO32-, PO32-, X—PO32-, CO2- and the said cation is selected from nitrogen-containing heterocyclic ring, N+R11R12R13 or X-N+R11R12R13, or a phenyl, wherein: R11, R12 and R13 are the same or different and are each independently H, a linear alkyl group having 1 to 6 carbons or a branched or cyclic alkyl group having from 3 to 6 carbons;

α, β and γ is 0 or any of the integers between 1 and 4;

B is phenyl or substituted phenyl, wherein the substituent is a linear alkyl group having 1 to 6 carbons, a branched or cyclic alkyl group having from 3 to 6 carbons; a charged group selected from anionic and cationic substituents—said anion is selected from SO3-, X—SO3-, OPO32-, X—OPO32-, PO32-, X—PO32-, CO2- and said cation is selected from nitrogen-containing heterocyclic ring, N+R11R12R13 or X-N+R11R12R13, wherein X has the same definition as above described), y is 0 or 1; P is a polyethylene glycol unit of Formula (OCH2CH2)z, wherein z is 0 or any of the integers between 1 and 1000.

LA2 in the present invention may be of the same meaning as LA1, may be a peptide or peptiod formed from natural or unnatural amino acids by amide bond formation, and may also be a suitable combination of both definitions. LA3 comprises 1 to 100 structural units connected in series which are selected from the group consisting of one or more glycine and alanine.

CCA and CCA' both contain suitable functional groups, which could be covalently couple with small molecules, nucleic acids, or tracer molecules by amide bonds, disulfide bonds, thioether bonds, thioester bonds, peptide bonds, hydrazone bonds, ester bonds, ether bonds or urethane bonds. Preferred chemical groups include, but not limited to: N-succinimidyl ester and N-sulfosuccinimidyl ester (to react with primary amine); maleimide group (to react with thiol group); pyridyldithio (to react with a sulfhydryl group and form a disulfide bond); and haloalkyl or haloacetyl (to react with a thiol group); an isocyanate group (to react with a hydroxyl group).

The preferred CCA1 in this present invention contains a peptide sequence (amide bond is formed by the condensation reaction of α-amino and carboxyl groups), wherein it must contain a Lys (Lysine) (number 1-100), the α-amino of the N-terminal amino acid of this peptide will form an amide bond with LA (or directly with the PCA). Based on the desired number of couplings, the ε-amino of lysine can either be used to introduce a maleimide functional group by a suitable bifunctional crosslinking agent, or be used to form an amido bond with the α-carboxyl group of another lysine to form a branched chain, and then the α- and ε-aminos of the lysine in the branched chain can be used to introduce maleimide groups by a suitable bifunctional crosslinker. And so on, by increasing the number of the lysine in the main chain and branched side chain, the number of functional groups introduced by such a CCA1 can achieve 1-1000. Preferred bifunctional cross-linking agents for introducing maleimide functional group include, but are not limited to, N-succinimidyl 4-(N-maleimidomethyl) cyclohexane-1-carboxylate (SMCC), the "long chain" SMCC analogue N-[alpha-mal eimidoacetoxy] succinimide ester (AMAS), N-gamma-Maleimidobutyryl-oxysuccinimide ester (GM-BS), 3-MaleiMidobenzoic acid N-hydroxysucciniMide ester (MBS), 6-maleimidohexanoic acid N-hydroxysuccinimide ester (EMCS), N-succinimidyl 4-(4-maleimidophenyl) butyrate (SMPB), Succinimidyl 6-[(beta-maleimidopropionamido) hexanoate (SMPH), Succinimidyl 4-(N-maleimidomethyl) cyclohexane-1-carboxy-(6-amidocaproate) (LC-SMCC), N-succinimidyl 11-(maleimido) undecanoate (KMUS), and a bifunctional crosslinking agent comprising N-hydroxy succinimide-(polyethyleneglycol alcohol) n (SM (PEG) n), wherein n indicated there are 2, 4, 6, 8, 12 or 24 polyethylene glycol (PEG) units.

Some examples of the preferred linkers which meet the above requirements are shown in FIGS. 3-6, but are not limited thereto. Linkers 1, 2, 3 and 4, all of which have a maleimide structure, can rapidly react with any thiol containing compounds (see below the 'payload') in a quantitative way, to form a sulfosuccinimide structure.

Another group of the preferred CCA2 has oligo cysteine sequences (the number of cysteines is 1-100, to form an amide bond through the condensation of α-amino and carboxyl groups), the α-amino group of the N-terminal cysteine will form an amide bond with LA (or directly with PCA), and its side chain thiol groups can be coupled to any molecules comprising a maleimide functional group.

The preferred linkers that meet the above requirements are shown in FIG. 7-10, but are not limited thereto.

The linker of the present invention, can be made by conventional solid phase polypeptide synthesis method with modifications, as shown in the following steps:

(1) Resin selection: for the C-terminal amide a Rink amide-MBHA Resin is used, and for the C-terminal carboxylic acid Wang resin is used.

(2) The swollen of resin: take the calculated amount of resin based on the target amount of peptide, add to a reaction column soaked with DCM, wash twice with DCM, the then merge in DMF for 30 min to allow fully swollen.

(3) Fmoc removal: treat the resin with a 20% solution of piperidine in DMF for 10 min under nitrogen, and remove by filtration, add the above solution again and react for another 5 min. The resin is washed twice with DCM, three times with DMF, followed by ninhydrin assay, resin should be reddish brown or dark blue.

(4) Coupling of the amino acid: weigh 2-4 equivalents of the amino acid to be coupled, add just enough DMF to dissolve, followed by suitable equivalents of coupling agent DIC or HBTU, activate for 5 min. The activated mixture is added to the column reactor under nitrogen to react for 2 h. Ninhydrin assay is used to test the resin, and repeat the coupling until it is colorless, which showed complete reaction. The resin is washed twice with DCM, and three times with DMF.

(5) Repeat steps (3) and (4) until all amino acids in the sequence are coupled. Boc protected amino acid is used for the last residue.

(6) Attachment of the side chain SMCC or other bifunctional molecules: Depending on the Lys side chain protecting groups, using different method to remove it. For example, catalytic hydrogenation is employed to take off Z, and hydrazine hydrate to remove ivDde. The activated SMCC or other bifunctional molecules are introduced directly to the exposed lysine side-chain amino group. If there is no side chain modification, the reaction is completed.

(7) Treatment and cleavage of Resin: After completion of the reaction, the resin composite was dried by nitrogen. A cleavage cocktail (TFA/phenol/H20/thioanisole/EDT/TIS) (80/5/5/5/3/2) was added (10 ml/g of resin), the reaction was stirred for 2 h at 0-5° C. under nitrogen. The resin was filtered, and to the filtrate was added 30× volumes of cold ether and leave for 2 h in refrigerator. The precipitate was collected by centrifugation, freeze-dried to give the crude peptide.

(8) Purification and mass spectrometry characterization: The crude peptide was dissolved in an appropriate proportion of aqueous acetonitrile and purified to the desired purity by reverse HPLC, MS is used to verify whether the molecular weight is consistent with the theoretical values.

2. The Payload

The payloads in the present invention are small molecules, nucleic acids, nucleic acid analogues, tracer molecules (including caged radionuclides and fluorescent molecules, etc.), the preferred small molecules are cytotoxins.

The said cytotoxins are selected from microtubule inhibitors such as paclitaxel and its derivatives, maytansine and derivatives, Auristatin and its derivatives, epothilone and analogues, Combretastatin A-4 phosphate, Combretastatin A-4 and its derivatives, indole-sulfa compounds, vinca alkaloids compounds such as vinblastine, vincristine, vindesine, vinorelbine, vinflunine, vinglycinate, anhydrovinblastine, dolastatins 10 and analogues, halichondrin B and Eribulin, indole-3-oxalyl amides, substituted indol-3-oxalyl amides, podophyllotoxins, 7-diethylamino-3-(2'-benzoxazolyl)-coumarin (DBC), discodermolide, Laulimalide; DNA topoisomerase inhibitors such as camptothecin and its derivatives, mitoxantron; mitoguazone; nitrogen mustard analogues such as Chlorambucil, Chlornaphazine, cyclophosphamide, Estramustine, ifosfamide, Mustine, Nitromin, Melphalan, Novembichin Phenamet, Phenesterine, Prednimustine, Trofosfamide, Uramustine; nitrosoureas such as Carmustine, streptozotocin, Fotemustine, Lomustine, Nimustine, Ranimustine; antibiotics such as the enediyne antibiotics, Dynemicin, Esperamicin, Neocarzinostatin, Aclacinomycin, Actinomycin, Anthroamycin, Azaserine, Bleomycins, actinomycin C, Carabicin, Idarubicin, Carzinophilin, Carminomycin, Actinomycin D, Daunorubicin, Doxorubicin, 6-diazo-5-oxo-L-norleucine, Adriamycin, Epirubicin, Esorubicin, Idarubicin, Marcellomycin, Mitomycins, Mycophenolic acid, Nogalamycin, Olivomycin, Peplomycin, Bofeimeisu, Puromycin, Adriamycin-Fe, Rodorubicin, Streptonigrin, Streptozocin, Tubercidin, Ubenimex, Zinostatin, Zorubicin; folic acid analogues such as Denopterin, Methotrexate, Pteropterin, Trimetrexate, Edatrexate; Purine analogues such as Fludarabine, 6-mercaptopurine, Thiamiprine, Thioguanine; pyrimidine analogues such as Ancitabine, Gemcitabine, Enoxaparin, Azacitidine, 6-Azauridine, Carmofur, Cytarabine, dideoxyuridine, deoxy-fluorouridine, Fluoruridine; androgens such as Calusterone, Dromostanolone propionate, Epitiostanol, Mepitiostance, Testolactone; anti-adrenal compounds such as Aminoglutethimide, Mitotane, Trilostane; trichothecenes such as T-2 toxin, verracurin A, Roridin A and Anguidine; arizidines such as Benzodopa, Carboquone, Meturedopa and Uredopa; platinum analogs such as Cisplatin, Carboplatin, Oxaliplatin, Miriplatin, Etoposide; anti-androgens such as Flutamide, Nilutamide, Bicalutamide, Leuprolide and Goserelin; protein kinase and proteasome inhibitors.

The preferred cytotoxins of the present invention are maytansine and its derivatives DM1, DM4 and Auristatin derivatives MMAE, MMAF, MMAD and the like.

3. Linker-Cytotoxin Intermediate and the Ring-Open Reaction

The preferred CCA1 containing linkers all have a maleimide ring structure in CCA1, which may react with any compound with a thiol group to form a sulfosuccinimide structure. The said compound with a thiol group may be a small molecule, a short peptide, a polypeptide, a peptide analogue, a protein, a nucleic acid, and a nucleic acid analogue. The said coupling intermediate can be treated under any appropriate conditions for sulfoccinimide ring-opening, to give the corresponding stable ring-open intermediate, as shown below:

PCA-(LA1)a-CCA1open-Y wherein, CCA1open-Y contains the following structure:

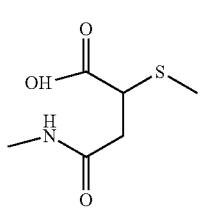

(IX)

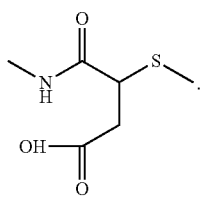

(X)

It has been reported that the succinimide ring of maleimide will form a pair of sulfosuccinimide isomers when being coupled with a thiol group. The sulfosuccinimide also forms isomers when the ring is opened, as shown in Formula (IX) and (X), but the activity is not affected.

A solution of the preferred linker 1, 2, 3 or 4 of the present invention is incubated with a solution of the preferred cytotoxin, maytansine derivative DM1, to form a linker-DM1 intermediate containing sulfosuccinimide structure, as shown in FIG. 11-14 respectively. The molecules formed by coupling of the preferred linker 1, 2, 3 or 4 of the present invention with the preferred cytotoxin DM1, followed by ring-open are shown in FIGS. 15-18. The ring-open reaction can be carried out under the following conditions but not limited to: 0.1-0.5M Lys, 0.1-0.5M Arg, 0.1-0.5M Tris Base, 0.1-0.5M sodium bicarbonate, 0.1-0.5M sodium carbonate, 0.1-0.5M sodium borat, at room temperature for 2-12 h. Under the preferred conditions, the ring-open efficiency can reach 10%, 20%, 30%, 50%, 60%, 70%, 80%, 90%, or nearly 100%. A complete ring-open process of linker 2-DM1 intermediate (n=3) is illustrated in the examples.

Most importantly, the preparation of a highly pure ring-open intermediate can be achieved by semi-preparative/preparative HPLC or other suitable separation methods regardless of the succinimide ring-open efficiency, thus ensuring the subsequent use in antibody coupling (see the Examples).

The said preferred CCA2 containing linkers all have a thiol group in CCA2, which may react with any maleimide containing molecule to form a sulfosuccinimide structure. The substance which comprises a maleimide may be a small molecule, a short peptide, a polypeptide, a peptide mimic, a protein, a nucleic acid, and a nucleic acid analogue. The above-described coupling intermediate can be fully treated under any appropriate ring-open conditions for succinimide ring, to give the corresponding stable ring-open structure, as shown below:

PCA-(LA1)a-CCA2open-Y

Wherein, CCA2 open-Y contains the following structure:

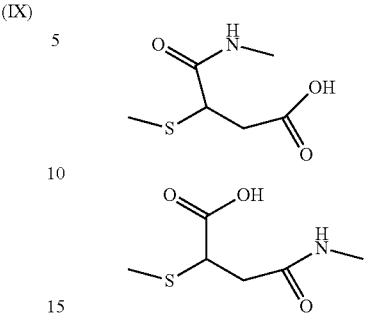

(XI)

(XII)

It has been reported that the succinimide ring of maleimide will form a pair of sulfosuccinimide isomers when being coupled with a thiol group. The sulfosuccinimide also forms isomers when the ring is opened, as shown in Formula (XI) and (XII), but the activity is not affected.

A solution of the above linker 5, 6, 7 or 8 is coupled to MC-VC-PAB-MMAE respectively to form a linker-MMAE intermediate containing sulfosuccinimides shown in FIG. 19-22, the cytotoxins used in this invention include but not limited to MMAE. The molecules formed by coupling of the preferred linker 5, 6, 7 or 8 of the present invention with the preferred cytotoxin MMAE, followed by ring-open are shown in FIGS. 23-26. The ring-open reaction can be carried out under the following conditions but not limited to: 0.1-0.5M Lys, 0.1-0.5M Arg, 0.1-0.5M Tris Base, 0.1-0.5M sodium bicarbonate, 0.1-0.5M sodium carbonate, 0.1-0.5M sodium borate, at room temperature for 2-12 h. Under the preferred conditions, the ring-open efficiency can reach 10%, 20%, 30%, 50%, 60%, 70%, 80%, 90%, or nearly 100%. A complete ring-open process of linker 5-MMAE intermediate (n=3) is illustrated in example 13.

Most importantly, the preparation of a highly pure ring-open intermediate can be achieved by semi-preparative/preparative HPLC or other suitable separation methods regardless of the succinimide ring-opening efficiency, thus ensuring the subsequent use in antibody coupling (see the Examples).

4. Antibody (Ab)

The antibody of the present invention is a recombinantly prepared monoclonal antibody, a chimeric antibody, a humanized antibody, an antibody fragment and antibody mimic (e.g., Fab, ScFv, minibody, diabody, nanobody, etc.).

The preferred antibodies of the invention are genetically engineered recombinant antibodies, the C-terminus of the heavy and/or light chain of which contains a specific modification based on the ligase recognition sequence, the said ligase herein refers to a transpeptidase, including but not limited to various natural Sortases (including Sortase A, B, C, D, and *L. plantarum* Sortase, etc., see patent US20110321183A1) and a variety of optimized and modified new transpeptidases. The ligase recognition site can be a typical recognition sequence (LPXTG (SEQ ID NO: 18)) derived from *Staphylococcus aureus* Sortase A, wherein X may be any natural or unnatural amino acid; the ligase recognition site can also be a recognition sequence of other types of Sortases (the recognition sequence of the donor substrate of Sortase are: NPQTN (SEQ ID NO: 19) for *Staphylococcus aureus* Sortase B, NPKTG (SEQ ID NO: 20) for *Bacillus anthracis* Sortase B, LPXTG (SEQ ID NO: 18) for *Streptococcus pyogenes* Sortase A, LAXTG (SEQ ID NO: 21) for *Streptomyces coelicolor* Sortase subfamily 5, LPQTSEQ (SEQ ID NO: 22) for *Lactobacillus plantarum*

Sortase etc.); the ligase recognition site can also be other totally new recognition sequence of transpeptidase optimized by manual screening.

Antibodies of the present invention are more preferably a series of genetically engineered anti human ErbB2/HER2 antibodies, the anti-ErbB2/HER2 antibodies are selected from monoclonal antibodies, chimeric antibodies, humanized antibodies, antibody fragments and antibody mimics (such as Fab, ScFv, minibody, diabody, nanobody etc.). The anti-ErbB2/HER2 antibody specifically binds to the extracellular domains of ErbB2/HER2 receptor, and inhibits the growth of tumor cells which highly express Her2 receptors, in vivo and in vitro.

A combination of engineered anti-ErbB2/HER2 antibody based on Herceptin/Trastuzumab transformation is preferred in the present invention. The light chain (LC) of said antibody includes 3 types: a wild type (LC); a C-terminal modified light chain, which is modified by direct introduction of a ligase recognition sequence LPETGG (SEQ ID NO: 23) (LCCT); a C-terminal modified light chain which is modified by the introduction of a short linker moiety (Gly-Ala) plus a ligase recognition sequence LPETGG (SEQ ID NO: 23) (LCCT$_L$). The heavy chain (HC) of said antibody also includes 3 types: a wild type HC; a C-terminal modified heavy chain, which is modified by the direct introduction of a ligase recognition sequence LPETGG (SEQ ID NO: 23) (HCCT); a C-terminal modified heavy chain which is modified by the introduction of a short linker moiety (Gly-Ala) plus a ligase recognition sequence LPETGG (SEQ ID NO: 23) (HCCTL$_L$). Combinations of the heavy chain and the light chain described above will form 3 preferred antibodies. Combinations of any one of heavy chain and any one of light chain will form 8 preferred antibodies. The sequences of amino acid residues are listed in the amino acid sequence list.

5. The Preparation and Quality Control of ADCs

ADCs prepared by traditional chemical coupling are not site specific. The drug antibody ratio (DAR) varies a lot, resulted in ADC with serious heterogeneity, which cannot be further purified. The ADC of the present invention is prepared by site-specific coupling.

1) The Preparation Method

Step 1, the ring-open linker-cytotoxin intermediates shown in Formula (I), (II), (III) or (IV) as described previously are prepared. The separation and preparation of product of a high purity is achieved by semi-preparative/preparative HPLC, regardless the efficiency of the succinimide ring-open reaction.

Step 2, Genetically engineered recombinant antibody containing the ligase specific recognition sequence is expressed in CHO cell or other suitable mammalian cell culture system, and purified.

Step 3, The coupling reaction between the recombinant antibody (or antibody mimic) and the linker-cytotoxin ring-open intermediate. The recombinant antibody, of which the C-terminus of light chain and/or heavy chain containing a ligase specific recognition site, is coupled to a linker-cytotoxin intermediate by appropriate ligase (or ligase combination) under appropriate catalytic conditions.

The preferred antibodies react with a linker-cytotoxin intermediates through ligase catalysis to give a series of preferred ADCs, which are shown in FIGS. 27-32. The details of which are described in the corresponding examples.

2) Structure Analysis of the ADCs

ADCs provided by the present invention can be characterized in several ways. The efficiency of the coupling reaction can be primarily assayed by SDS-PAGE method, the precise molecular structure can be obtained from high accuracy mass spectrometry (ESI-MS), DAR distributions can be analyzed by hydrophobic interaction high performance liquid chromatography (HIC-HPLC), and the degree of antibody aggregation may be analyzed by molecular sieve high performance liquid chromatography (SEC-HPLC).

6. ADC Activity Assay

1) The Binding Affinity Assay of the ADC to the Tumor Cell Surface Specific Antigen The present invention provides a method for the determination of the binding affinity of the ADC with tumor cell surface specific antigen, for screening and identifying highly potent ADCs which recognize and bind to the tumor cell surface antigens or receptors. In a particular embodiment, an ADC candidate is incubated with cells derived from stable breast cancer cell lines (10-60 min), and FACS was used to assay the binding affinity of candidate drug GQ1001 to the ErbB2/Her2 receptors on the breast cancer cell surface. The results showed that ADC, such as GQ1001 obtained by the linker and coupling method of the present invention can specifically recognize cell surface ErbB2/Her2 receptor, and the binding affinity is not significant different from that of Herceptin, suggesting that the linkers and the coupling methods of the present invention has little effect on the antibody itself.

2) The Selective Inhibition of ADCs on Tumor Cell Proliferation

To study the selective inhibition of a candidate ADC on tumor cells (e.g. ErbB2/Her2 high expressing tumor cells), the following assays were used to determine the cytotoxicity or proliferation inhibition of candidate ADCs: the mammalian tumor cells with tumor-associated antigen or receptor protein (e.g. breast cancer cells with high or low ErbB2/Her2 expression) were incubated with the candidate ADC for about 12-120 h, the Cell Titer Glo method was used to determine the cell viability.

In one example, ADC GQ1001 were incubated with human breast cancer cells (such as BT474, HCC1954, SK-BR-3, MCF-7, MDA-MB-468), human ovarian carcinoma cells (SK-OV-3), human gastric cancer cells (NCI-N87) 24-120 h, intracellular ATP was detected by Cell Titer Glo assay, and the amount of ATP will reflect the cell viability. The results show that GQ1001 selectively inhibits the proliferation of cells with high expression of ErbB2/HER2.

3) The Metabolism and Stability in Rat

ADC candidate drugs were injected to rat tail vein at 5-50 mg/kg, blood samples were collected at different time points after administration, and the concentration of candidate ADCs in serum was detected by ELISA. In a particular example, GQ1001 or Kadcyla was administered via tail vein in a single injection to SD rats, blood samples were collected at different time points from 1 h to 28 days after administration, ELISA assay was carried out to detect the serum GQ1001 or Kadcyla concentration. No significant difference was observed between the concentration change of GQ1001 and Kadcyla in rats during the experiment using the current assay.

4) The In Vivo Efficacy of ADCs

The in vivo anti-tumor effect of the candidate ADC was determined using xenograft model of nude mice after administration of the candidate ADC. In one example, human breast tumor cell was used as the xenograft model and the growth of the tumor was observed after a single tail veil injection of ADC GQ1001 at 0.5-50 mg/kg. The results confirm a single intravenous injection of GQ1001 in the dose range of 0.5-50 mg/kg can significantly inhibit the proliferation of ErbB2/Her2 positive tumor cells.

5) Toxicity for Rodents

The acute toxicity of the candidate ADC was evaluated in rats. Female Sprague-Dawley rats were injected with high doses (60 mg/kg or more) of ADCs, and impact of drugs on the animals was then observed and analyzed, and index such as body weight, clinical signs, hematology, clinical biochemistry and histopathology were studied to evaluate the toxicity of the candidate ADC. It was found that at the same dose level (60 mg/kg), the toxicity of the ADC GQ1001 was significantly less than Kadcyla.

The present invention provides a special class of linkers, which can be used for connection of proteins, especially various antibodies with a variety of small molecules, peptides, nucleic acids, tracers and other substances, to prepare conjugate which can be used in academic research, clinical diagnostic and treatment.

The linkers provided in this invention may be used in the site-specific ligation of small molecules with antibody, resulting in highly homogeneous ADCs. The present invention especially provides a class of ADCs formed by site-specific connection of small molecule cytotoxic agents, especially maytansine and derivatives to anti-human ErbB2/Her2 antibodies.

The ADCs of the present invention are useful for treating a variety of diseases or disorders such as tumor and autoimmune diseases. Tumors susceptible to ADC treatment include those with specific tumor-associated antigens or cell surface receptors, and which will be specifically recognized by the antibody of the ADC, and then killed by the cytotoxic small molecule connected in the ADC.

The ADC of the present invention, GQ1001, which is formed by connection of anti-human ErbB2/Her2 antibody with small molecule cytotoxin, can bind specifically with the ErbB2/Her2 on the tumor cell surfaces, thus selectively kill the tumor cells which highly express ErbB2/Her2, and cure various ErbB2/Her2-positive tumors, including but not limited to breast cancer, gastric cancer, lung cancer, ovarian cancer, etc.

1) The linkers of the present invention can be applied to the site-specific ligation of a variety of proteins, especially antibodies to small molecules, peptides, nucleic acids, fluorescent tracers, indicator and many other substances. The coupling conditions are mild, with no adverse effect on the activity of biological molecules, thus may have wide applications.

2) The linkers of the present invention are a succinimide ring-open structure, in comparison with the ring-closed structure, it is more stable in mammals, less easily to inter-change with thiols of cysteine, glutathione and albumin. ADC obtained with this linker can be more stable in vivo, overcoming the problem of off-target release of small molecules in the current ADCs.

3) The ADC of the present invention is a product of site-specific coupling, which is highly homogeneous. In comparison with ADCs prepared by traditional non-site-specific coupling, the ADCs of the present invention make a significant improvement in quality control and drug safety, provide a fundamental solution to the disturbed of ADC heterogeneity problem of pharmaceutical industry.

BRIEF DESCRIPTION OF THE DRAWINGS

FIG. 15A and FIG. 15B are isomers)

FIG. 16A and FIG. 16B are isomers)

FIG. 17A and FIG. 17B are isomers)

FIG. 18A and FIG. 18B are isomers)

FIG. 23A and FIG. 23B are isomers)

FIG. 23A and FIG. 23B are isomers)

FIG. 25A and FIG. 25B are isomers)

FIG. 26A and FIG. 23B are isomers)

FIG. 27A and FIG. 27B are isomers).

FIG. 28A and FIG. 28B are isomers).

FIG. 29A and FIG. 29B are isomers).

FIG. 30A and FIG. 30B are isomers).

FIG. 31A and FIG. 31B are isomers).

FIG. 32A and FIG. 32B are isomers).

FIG. 35A, FIG. 35B, FIG. 35C, FIG. 35D, and FIG. 35E are the UPLC results of ring-open reaction which was carried out for 20 minutes, 40 minutes, 60 minutes, 2 hours and 4 hours respectively.

BEST MODE FOR CARRYING OUT THE INVENTION

The present invention is further illustrated in combination with specific examples shown below. It should be understood that these examples are merely intend to illustrate the present invention but not to limit the scope of the invention.

Unless otherwise stated, all scientific and technical terms used herein are of the same meaning as those understood by a person skilled in the art. In addition, any methods and materials similar or equivalent to the contents described is applicable in the method of the present invention. The preferred implementation method and the material described herein are exemplary only.

EXAMPLE

Example 1—The Production, Purification and Characterization of Anti-Human ErbB2/Her2 Antibody T-LCCT$_L$-HC 1) The Production of Antibody T-LCCTL-HC SEQ ID No.1 antibody T-LCCTL-HC encoding plasmid construct was transfected into CHO cells and the cell population was established and screened for a highly expressed cell population, which was cultured with reference to the culture process of Trastuzumab in a 5-10 L reactor, and supernatant was collected.

2) The Purification of Antibody T-LCCT$_L$-HC

The purification of T-LCCT$_L$-HC was carried out in a standard process using the combination of Mab Select affinity chromatography and Sepharose S cation exchange chromatography, the purified products were dissolved in the original Trastuzumab drug buffer (5 mM histidine-HCl, 2% Trehalose, 0.009% Polysorbate 20, PH 6.0), and frozen in small aliquots.

3) The Quality Control of Antibody T-LCCT$_L$-HC

The purity of the above purified antibody T-LCCT$_L$-HC is 98.5% by SDS-PAGE; the content of high molecular weight polymer of the sample is less than 0.4% by SEC-HPLC; endotoxin content is less than 0.098 EU/mg.

Example 2—The Preparation of Linker 2-DM1 Intermediate (n=3, Ring-Open)

1) The Preparation and Quality Control of Linker 2-DM1 Intermediate (n=3, Ring-Closed)

Figure 1:
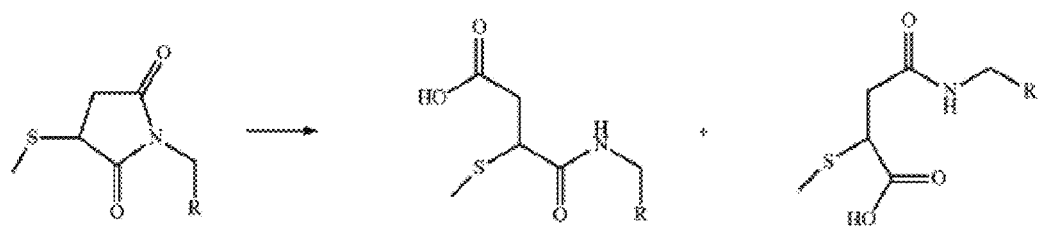
FIG. 1 The schematic diagram of ring-open reaction.
Figure 2:
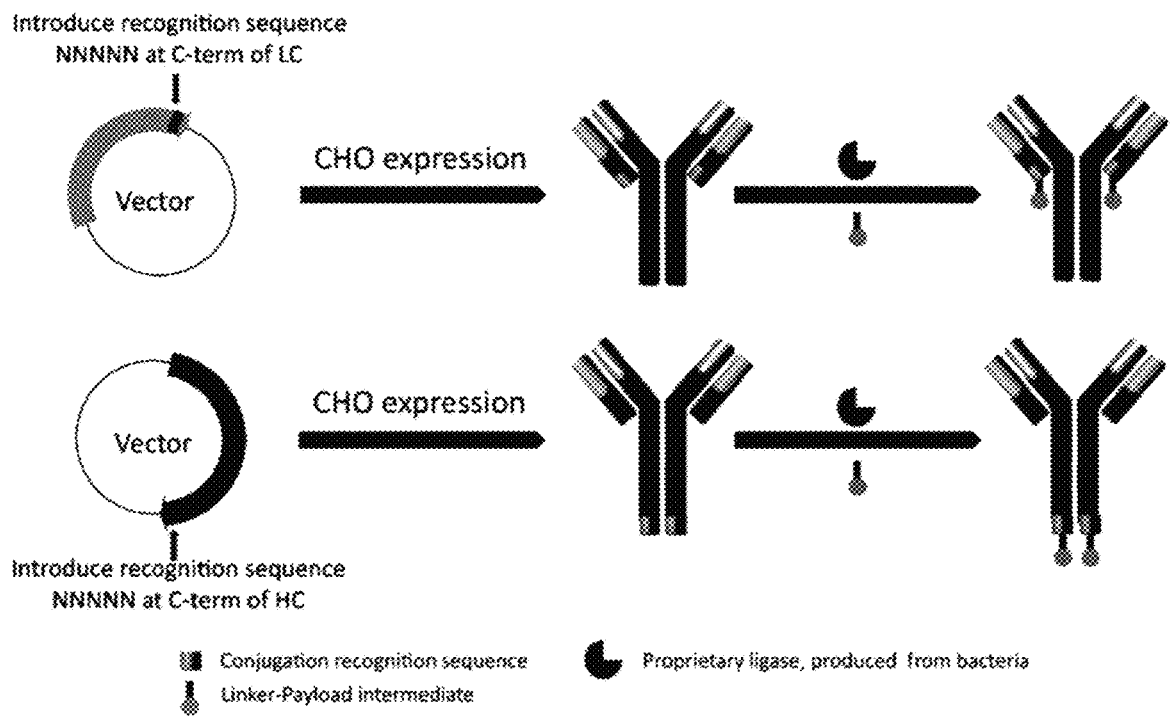
FIG. 2, The schematic diagram of enzyme-catalyzed coupling technology.
Figure 3:
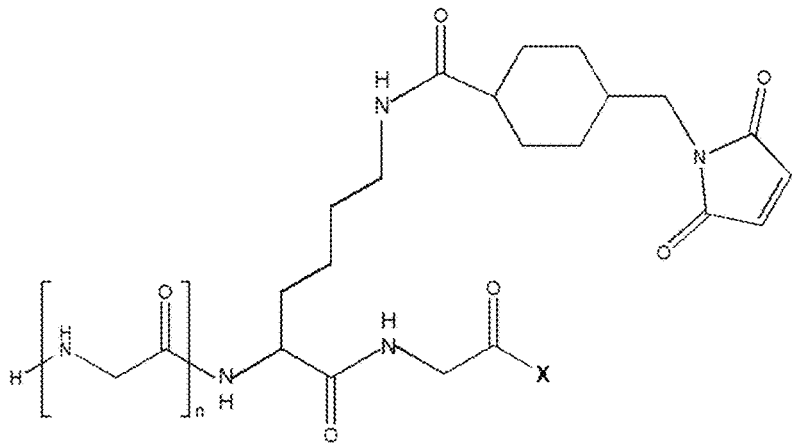
FIG. 3. The chemical structure of linker 1 (n is an integer from 1-100, x is —OH or —NH$_2$ group)
Figure 4:
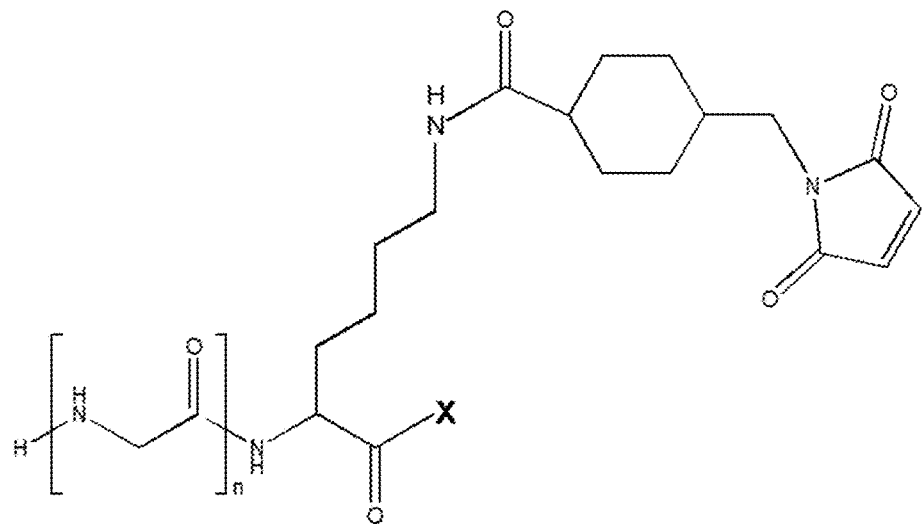
FIG. 4. The chemical structure of linker 2 (n is an integer from 1-100, x is —OH or —NH$_2$ group)
Figure 5:
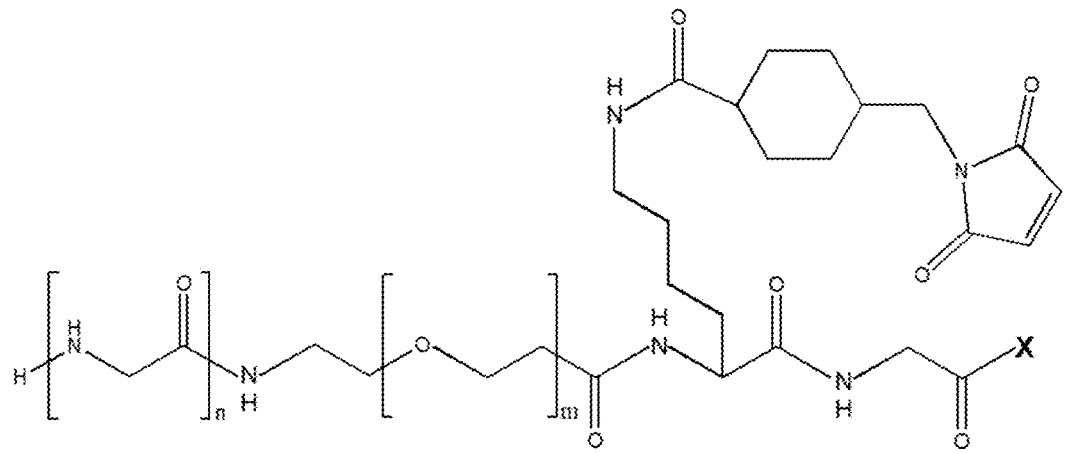
FIG. 5. The chemical structure of linker 3 (n is an integer from 1-100, m is 0 or any of the integers from 1-1,000, X is —OH or —NH$_2$ group)
Figure 6:
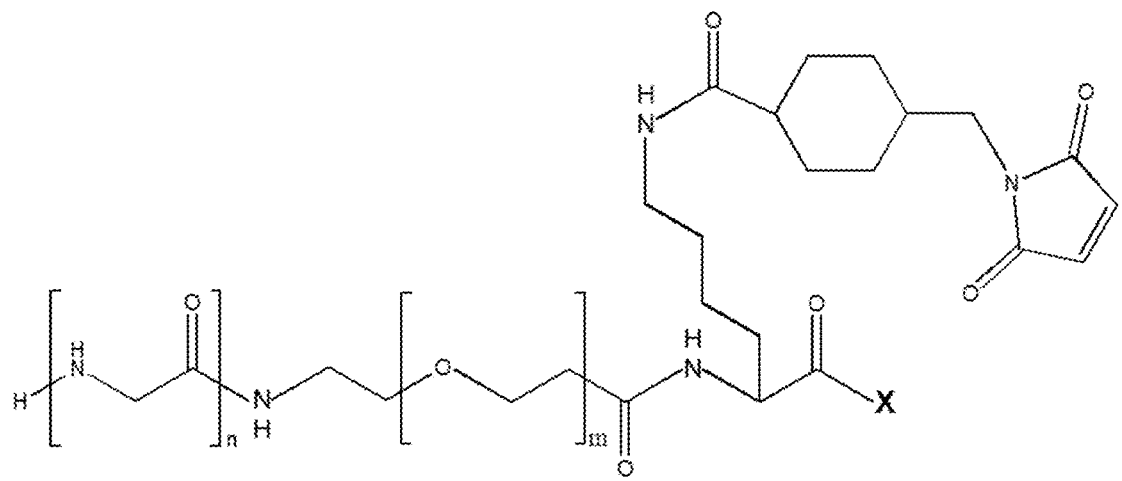
FIG. 6. The chemical structure of linker 4 (n is an integer from 1-100, m is 0 or any of the integers from 1-1,000, X is —OH or —NH$_2$ group)
Figure 7:
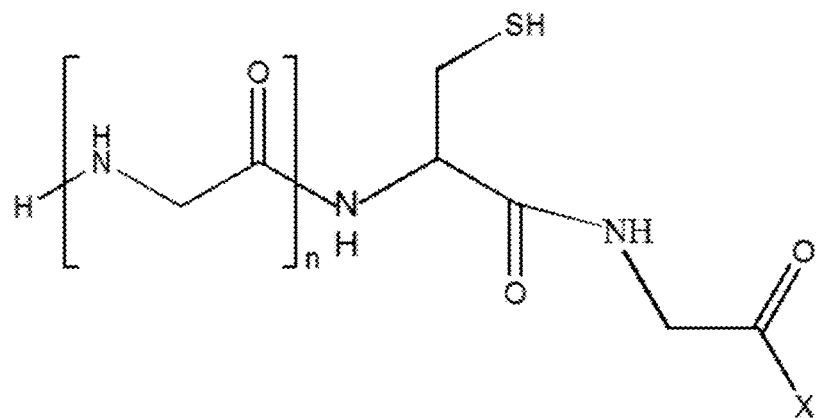
FIG. 7. The chemical structure of linker 5 (n is an integer from 1-100, x is —OH or —NH$_2$ groups)
Figure 8:
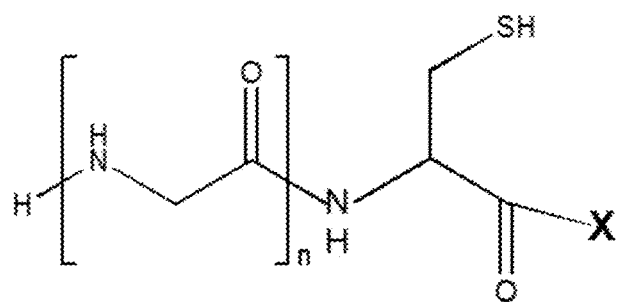
FIG. 8. The chemical structure of linker 6 (n is an integer from 1-100, x is —OH or —NH$_2$ groups)
Figure 9:
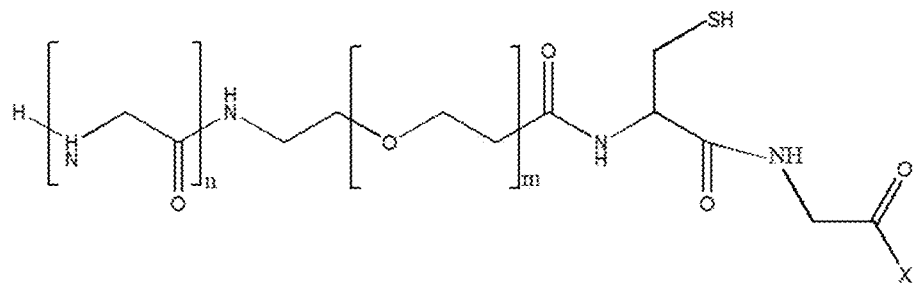
FIG. 9. The chemical structure of linker 7 (n is an integer from 1-100, m is 0 or any of the integers from 1-1,000, x is —OH or —NH$_2$ group)
Figure 10:
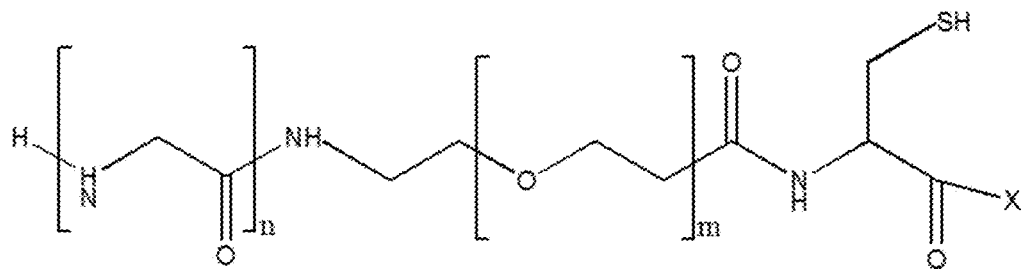
FIG. 10. The chemical structure of linker 8 (n is an integer from 1-100, m is 0 or any of the integers from 1-1,000, x is —OH or —NH$_2$ groups)
Figure 11:
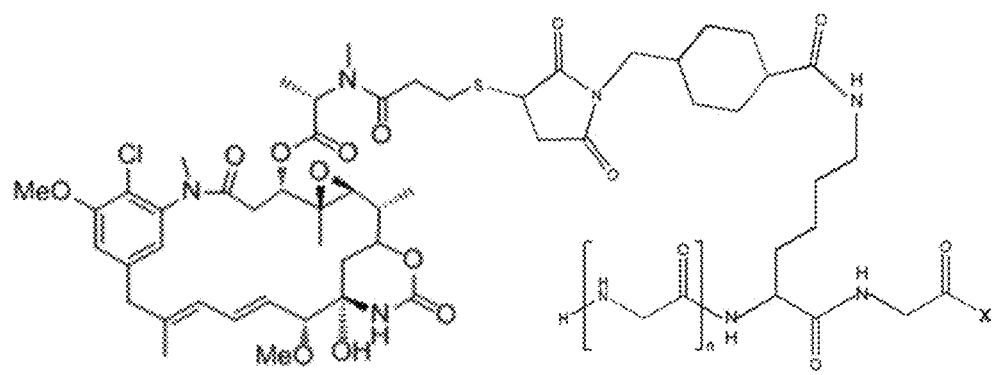
FIG. 11. The molecular schematic diagram of linker 1-DM1 intermediate (n is an integer from 1-100, x is —OH or —NH$_2$ group)
Figure 12:
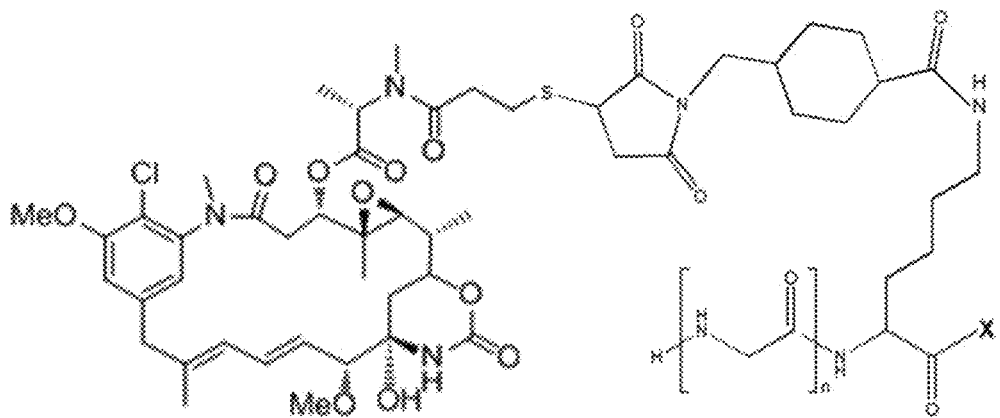
FIG. 12. The molecular schematic diagram of linker 2-DM1 intermediate (n is an integer from 1-100, x is —OH or —NH$_2$ group)
Figure 13:
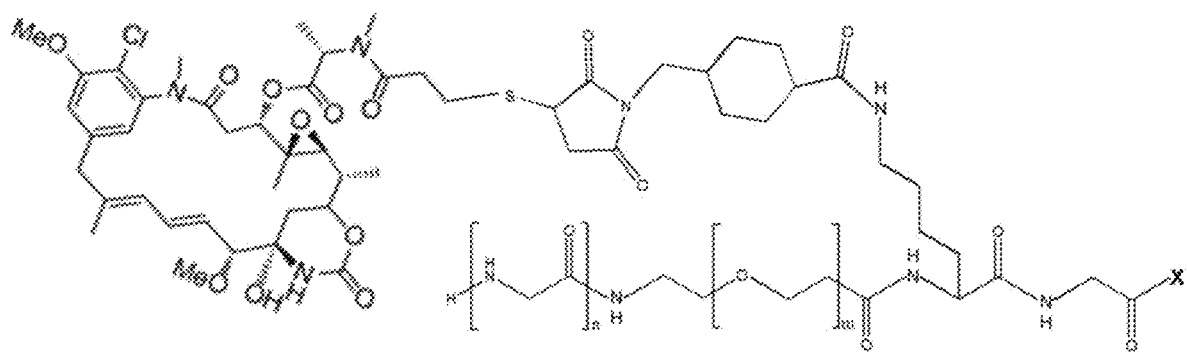
FIG. 13. The molecular schematic diagram of linker 3-DM1 intermediate (n is an integer from 1-100, m is 0 or any of the integers from 1-1000, x is —OH or —NH$_2$ group)
Figure 14:
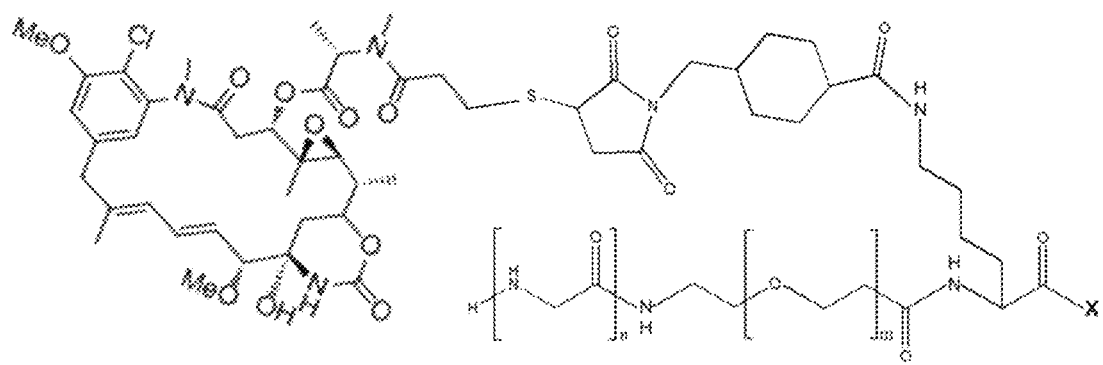
FIG. 14. The molecular schematic diagram of linker 4-DM1 intermediate (n is an integer from 1-100, m is 0 or any of the integers from 1-1000, x is —OH or —NH$_2$ group)
Figure 15A:
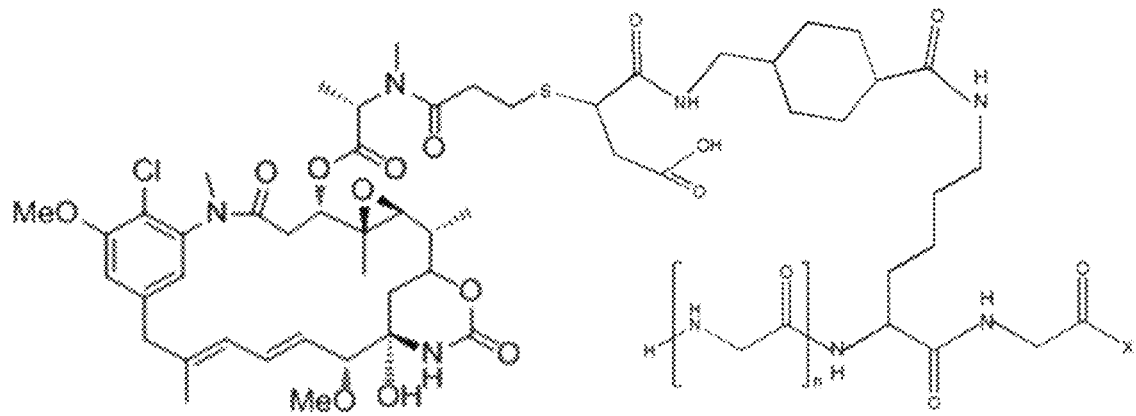
FIG. 15A and FIG. 15B. The ring-open molecular schematic diagram of linker 1-DM1 intermediate (n is an integer from 1-100, x is —OH or —NH$_2$ group.
Figure 15B:
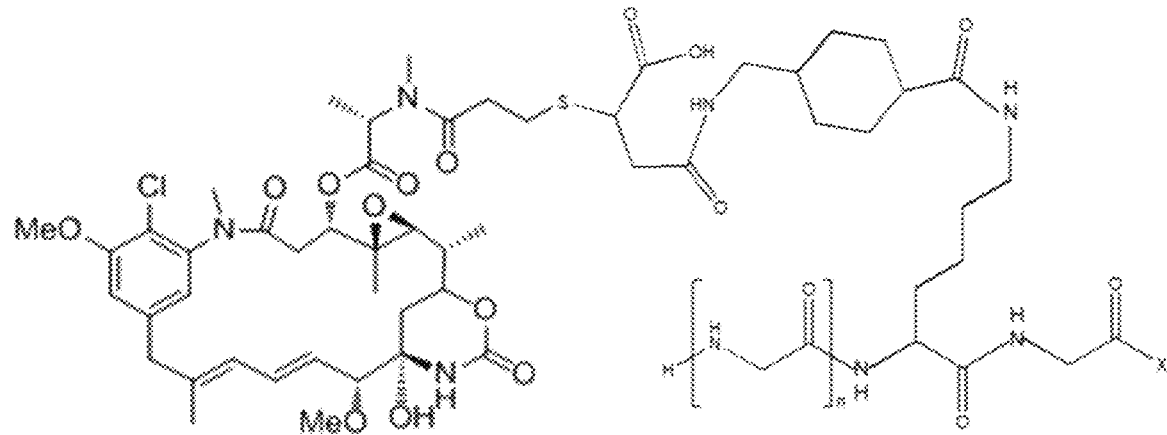
Figure 33:
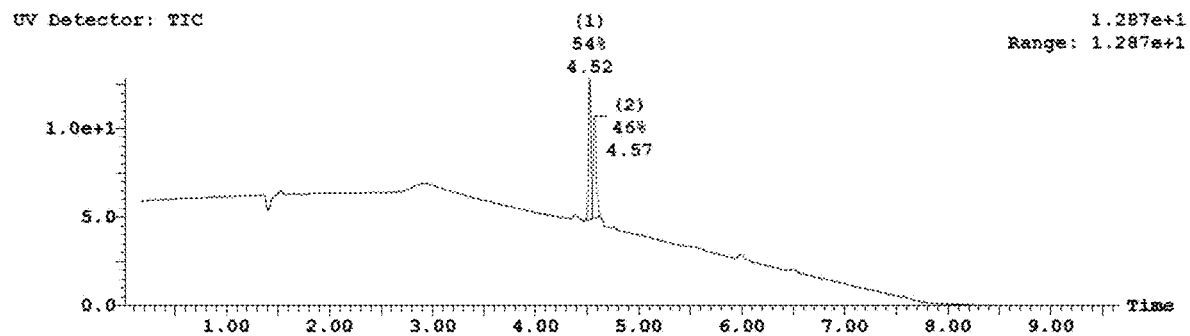
FIG. 33. The UPLC results of linker 2-DM1 intermediate (n=3, ring closed).
Figure 34:
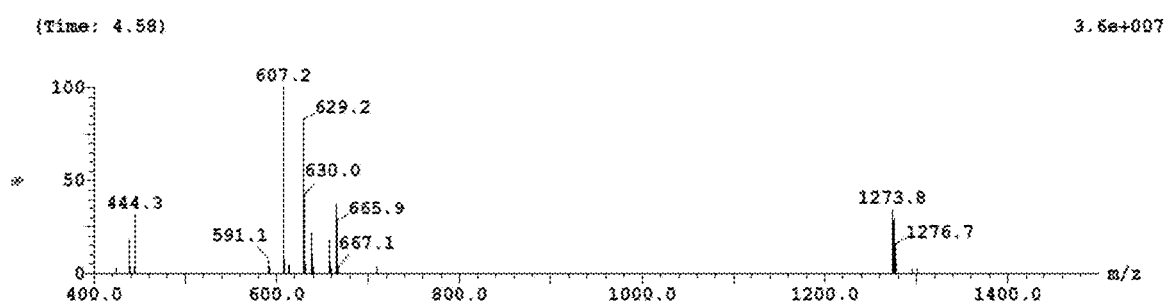
FIG. 34. The MS results of linker 2-DM1 intermediate (n=3, ring closed).
Figure 35A:
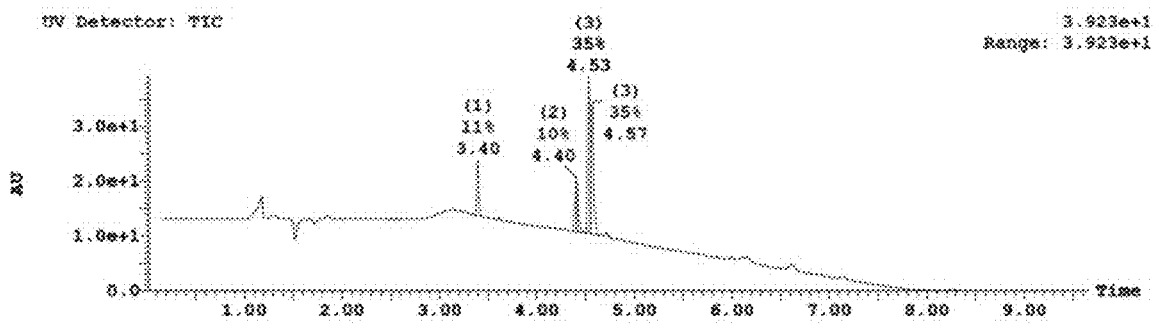
FIG. 35A, FIG. 35B, FIG. 35C, FIG. 35D, and FIG. 35E. The ring-open process of linker 2-DM1 intermediate (n=3, ring closed)
Figure 35B:
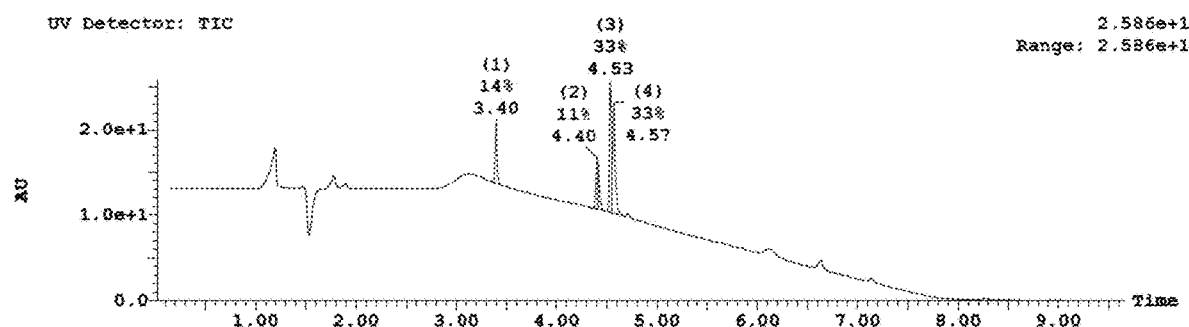
Figure 35C:
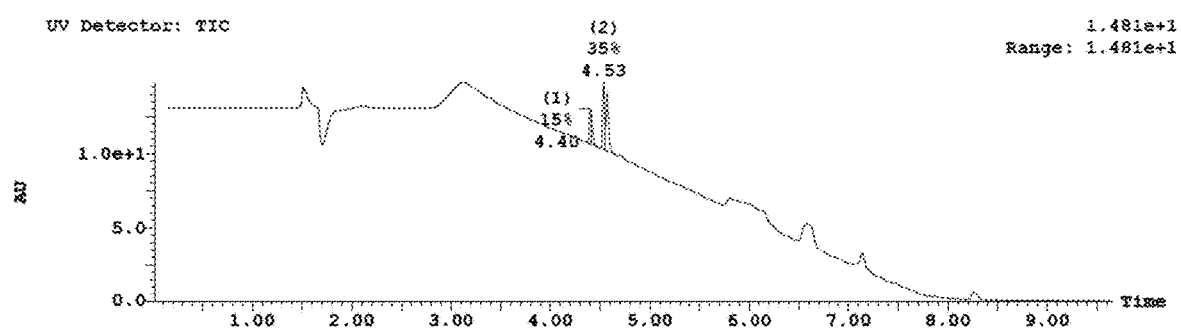
Figure 35D:
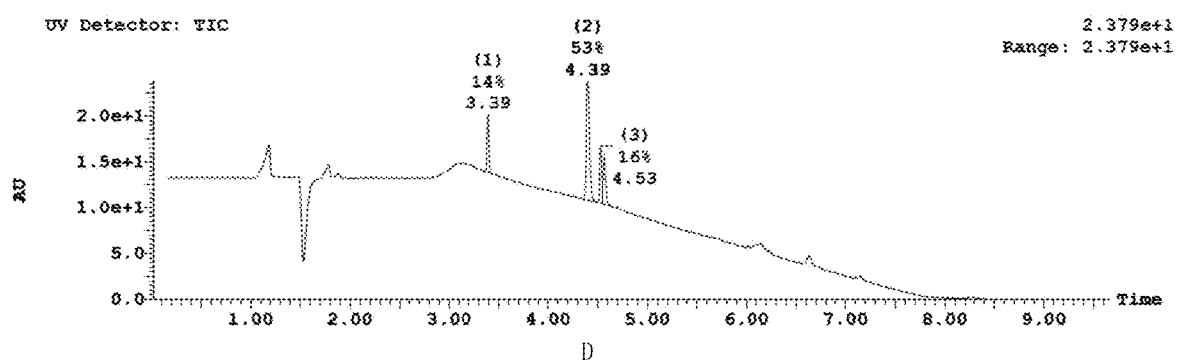
Figure 35E:
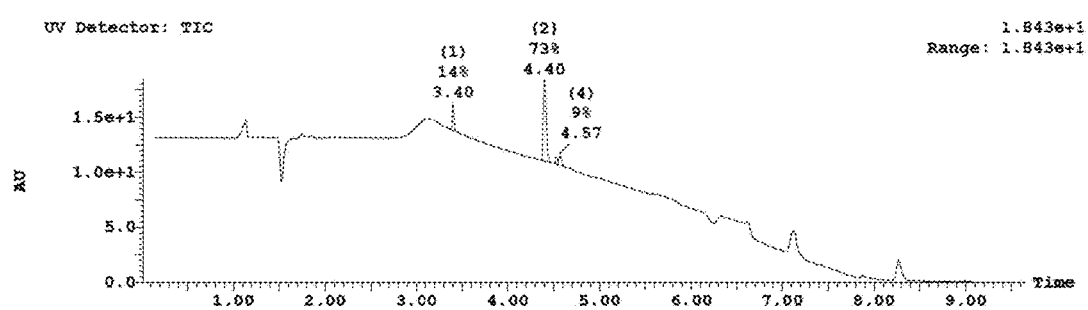

Linker 2 (n=3) and DM1 was weighed in a 1:1 molar ratio, mixed and dissolved sufficiently and react at 0-40° C. for 0.5-20 h, to give linker 2-DM1 intermediate (n=3, ring-closed, structure as shown in FIG. 12). The purity and molecular weight of linker 2-DM1 intermediate (n=3, ring-closed) were detected by UPLC-M, and results showed that the apparent purity is 100% (a mixture of isomers, roughly in 1:1 ratio, shown in FIG. 33), the found molecular weight is 1274 (FIG. 34), which is consistent with expectation.

2) The Ring-Open Reaction and Purification of Linker 2-DM1 Intermediate (n=3, Ring-Closed)

Figure 16A:
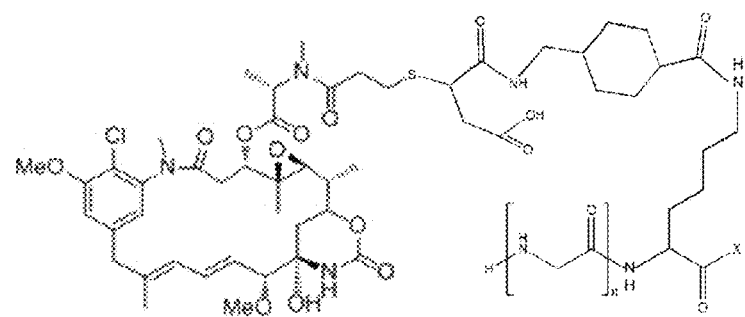
FIG. 16A and FIG. 16B. The ring-open molecular schematic diagram of linker 2-DM1 intermediate (n is an integer from 1-100, x is —OH or —NH$_2$ group.
Figure 16B:
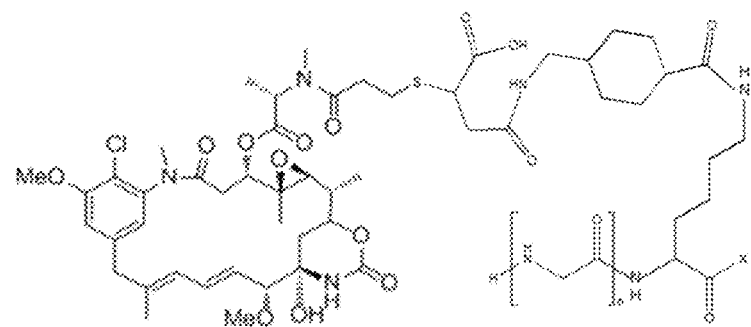
Figure 17A:
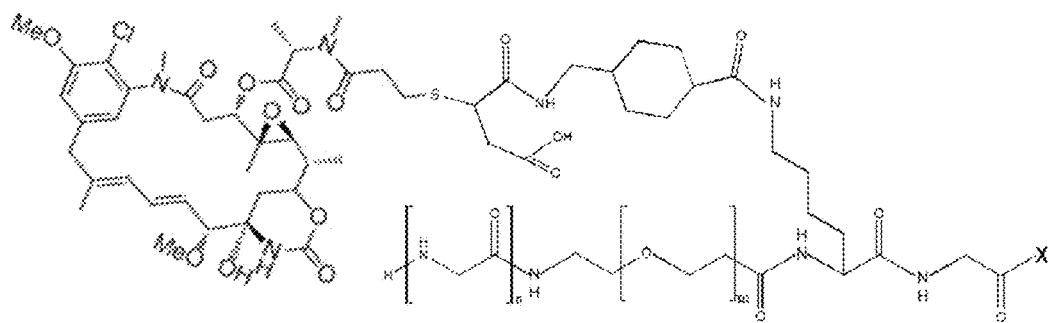
FIG. 17A and FIG. 17B. The ring-open molecular schematic diagram of linker 3-DM1 intermediate (n is an integer from 1-100, m is 0 or any of the integers between 1-1000, x is —OH or —NH$_2$ group.
Figure 17B:
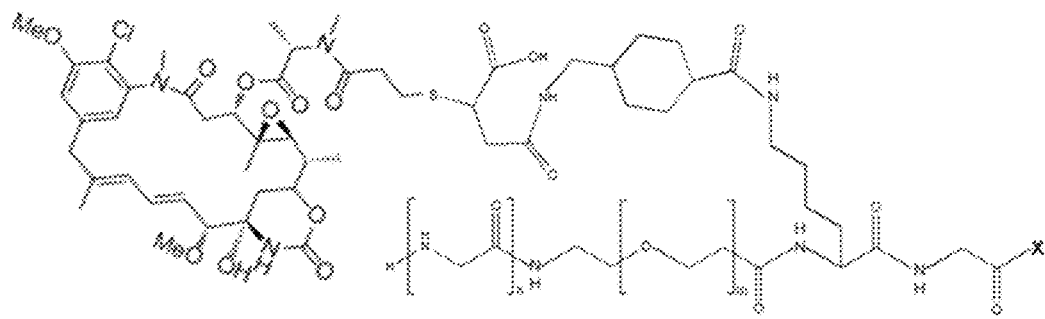
Figure 18A:
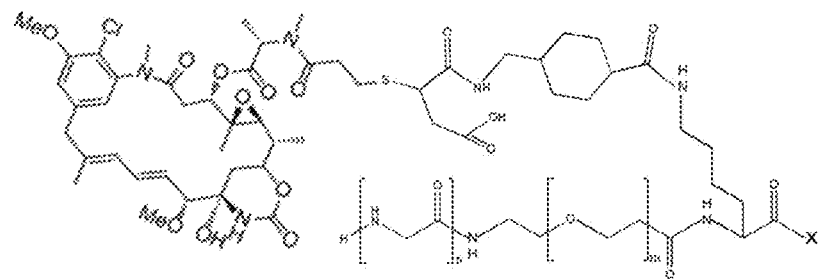
FIG. 18A and FIG. 18B. The ring-open molecular schematic diagram of linker 4-DM1 intermediate (n is an integer from 1-100, m is 0 or any of the integers between 1-1000, x is —OH or —NH$_2$ group.
Figure 18B:
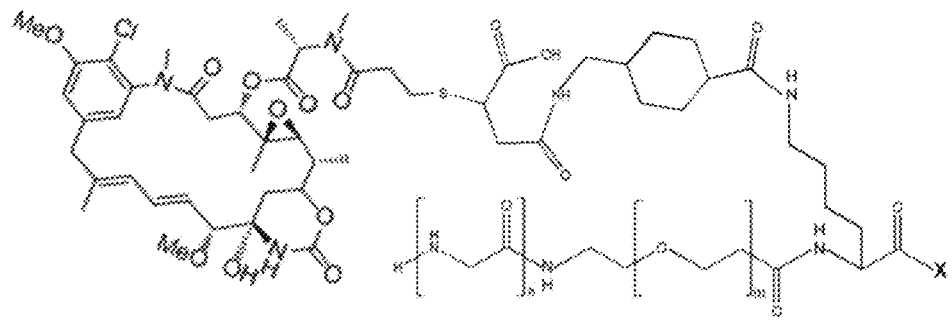

The solution of linker 2-DM1 intermediate (n=3, ring-closed) was mixed with an appropriate amount of Tris Base solution or other solution to promote the ring-open reaction, the reaction was carried out at 0-40° C. for 0.2-20 h, the resulting structure of linker 2-DM1 intermediate (n=3, ring-open) is shown in FIG. 16. UPLC results of ring-open reaction at 20 minutes, 40 minutes, 60 minutes, 2 hours and 4 hours were shown in FIG. 35 A-E. As the reaction proceeds, the ratio of linker 2-DM1 intermediate (n=3, ring-open) in the reaction mixture increased (from 10 to 73%). The preparation of a highly pure linker 2-DM1 intermediate (n=3, ring-open) can be achieved by semi-preparative/preparative HPLC, regardless of the succinimide ring-open efficiency in linker 2-DM1 intermediate (n=3, ring-open), thus ensuring the subsequent use in antibody coupling.

3) Quality Control of Linker 2-DM1 Linker Intermediate (n=3, Ring-Open)

Figure 36:
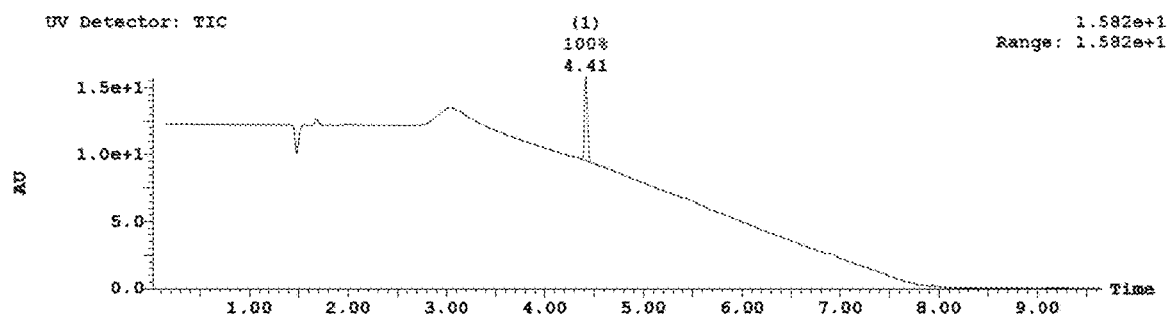
FIG. 36. The UPLC results of linker 2-DM1 intermediate (n=3, ring open).
Figure 37:
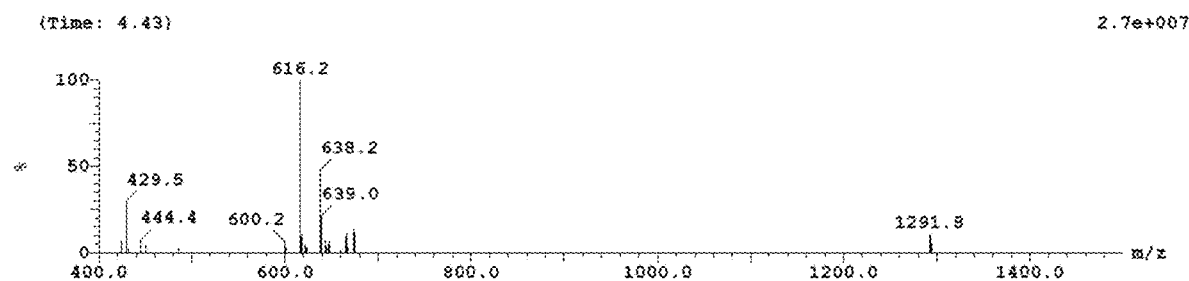
FIG. 37. The MS results of linker 2-DM1 intermediate (n=3, ring open).

An appropriate amount of linker 2-DM1 intermediate (n=3, ring-open) was weighed and the purity and molecular weight was detected by UPLC-MS, the results are shown in FIG. 36 and FIG. 37. The purity of the HPLC-purified linker 2-DM1 intermediate (n=3, ring-open) is 100%, the found mass is 1291.8, which is consistent with expectation, laying a solid foundation for the subsequent production of ADCs GQ-1001.

Example 3—Preparation of ADC GQ1001

Figure 28A:
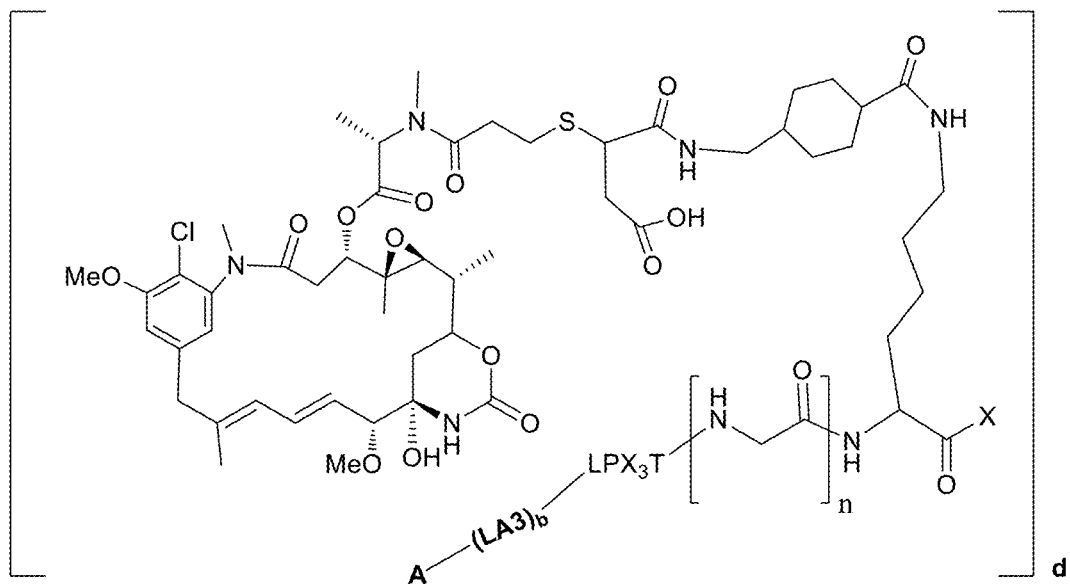
FIG. 28A and FIG. 28B. The molecular schematic diagram of preferred ADC2 molecules (n is an integer from 1-100, d is any of the integers from 1-20, X in ligase recognition sequence LPXT of is glutamic acid (E) or any other natural/unnatural amino acid; Ab is an antibody, LA3 is linker moiety, comprising 1 to 100 series-connected structure units which are selected from the group consisting of one or more glycine and alanine; each b is independently 0 or 1, indicating the presence or absence of LA3; x is —OH or —NH$_2$ group.
Figure 28B:
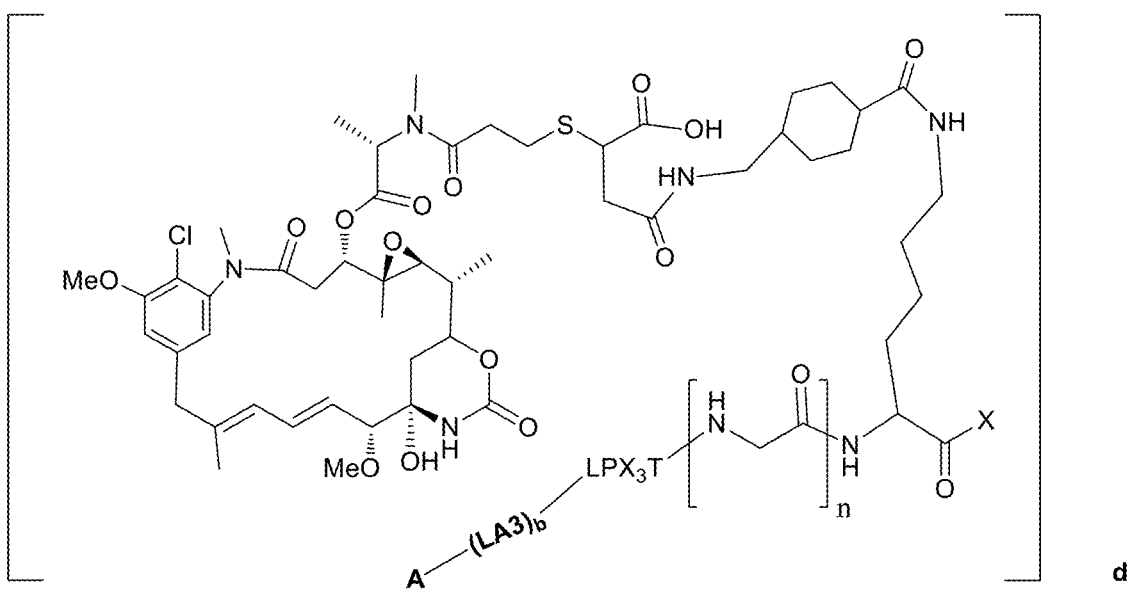
Figure 29A:
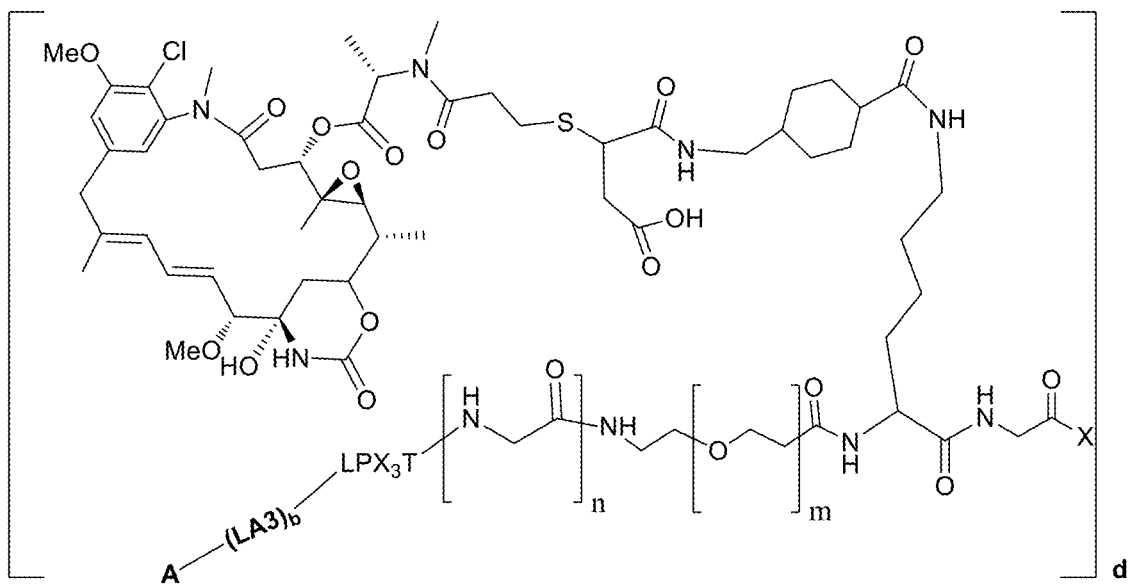
FIG. 29A and FIG. 29B. The molecular schematic diagram of preferred ADC3 molecules (n is an integer from 1-100, d is any of the integers from 1-20, X in ligase recognition sequence LPXT of is glutamic acid (E) or any other natural/unnatural amino acid; m is 0 or any of the integers from 1-1000, Ab is an antibody, LA3 is linker moiety, comprising 1 to 100 series-connected structure units which are selected from the group consisting of one or more glycine and alanine; each b is independently 0 or 1, indicating the presence or absence of LA3; x is —OH or —NH$_2$ group.
Figure 29B:
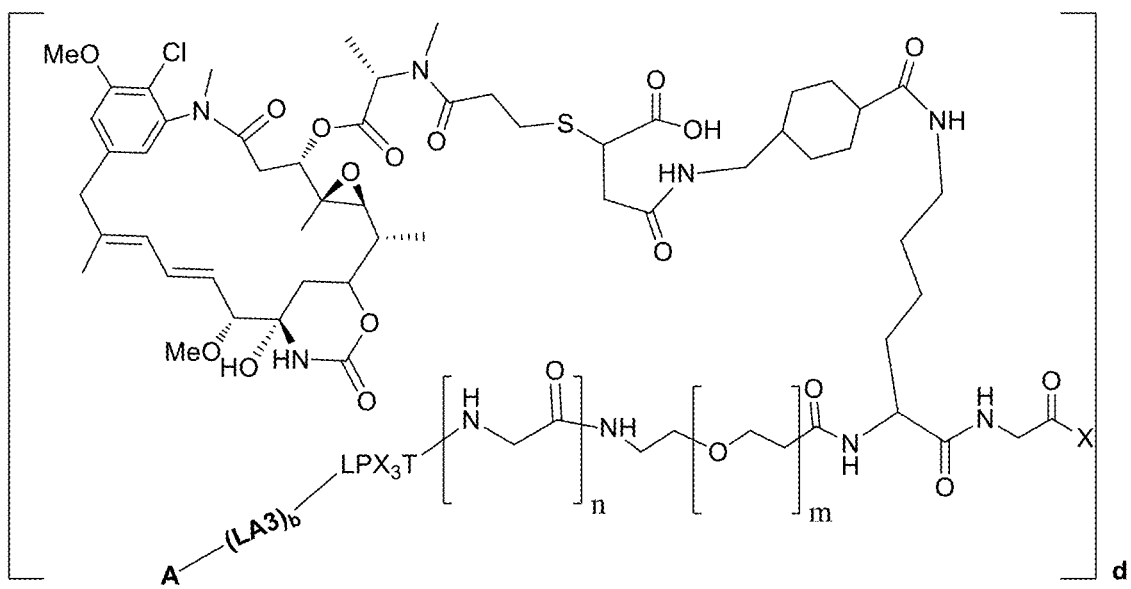
Figure 30A:
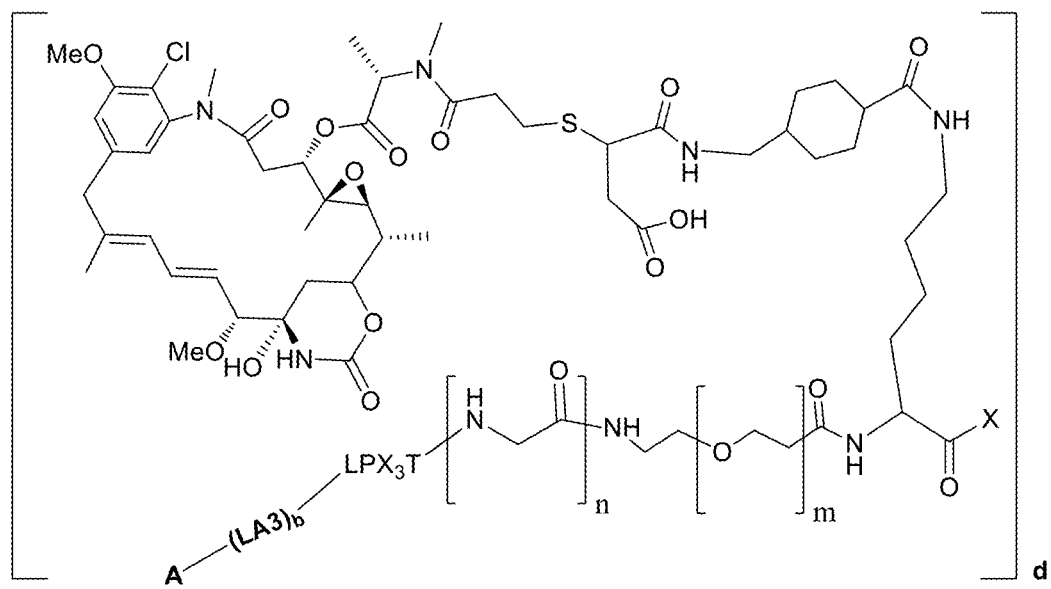
FIG. 30A and FIG. 30B. The molecular schematic diagram of preferred ADC4 molecules (n is an integer from 1-100, d is any of the integers from 1-20, X in ligase recognition sequence LPXT of is glutamic acid (E) or any other natural/unnatural amino acid; m is 0 or any of the integers from 1-1000, Ab is an antibody, LA3 is linker moiety, comprising 1 to 100 series-connected structure units which are selected from the group consisting of one or more glycine and alanine; each b is independently 0 or 1, indicating the presence or absence of LA3; x is —OH or —NH$_2$ group.
Figure 30B:
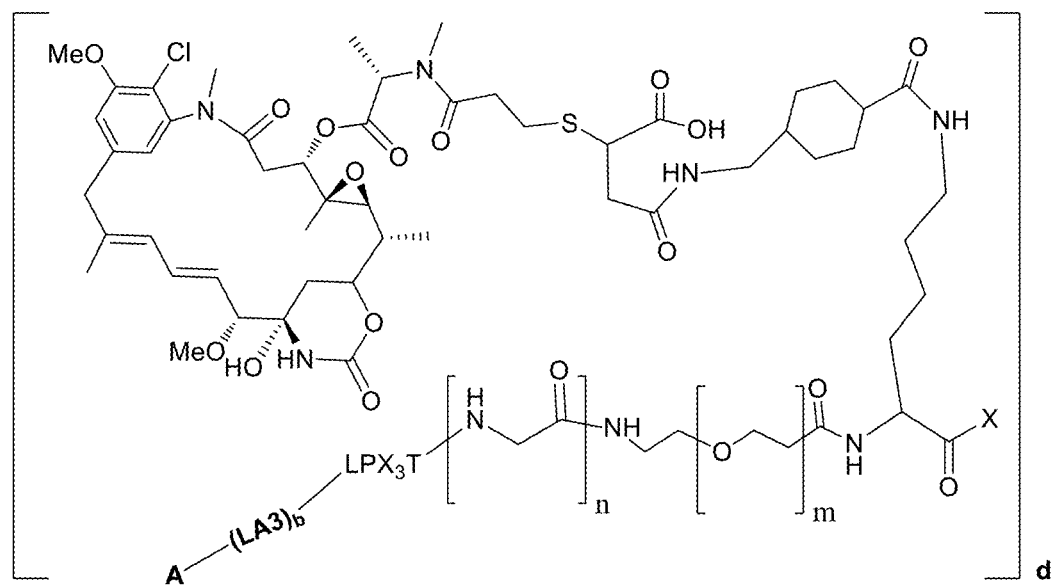
Figure 31A:
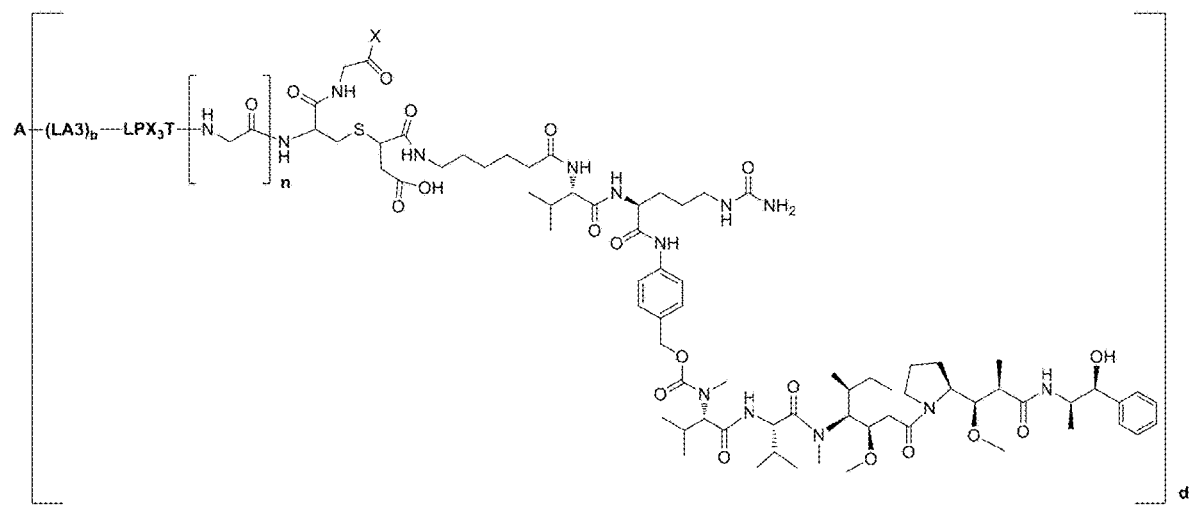
FIG. 31A and FIG. 31B. The molecular schematic diagram of preferred ADC5 molecules (n is an integer from 1-100, d is any of the integers from 1-20, X in ligase recognition sequence LPXT of is glutamic acid (E) or any other natural/unnatural amino acid; Ab is an antibody, LA3 is linker moiety, comprising 1 to 100 series-connected structure units which are selected from the group consisting of one or more glycine and alanine; each b is independently 0 or 1, indicating the presence or absence of LA3; x is —OH or —NH$_2$ group.
Figure 31B:
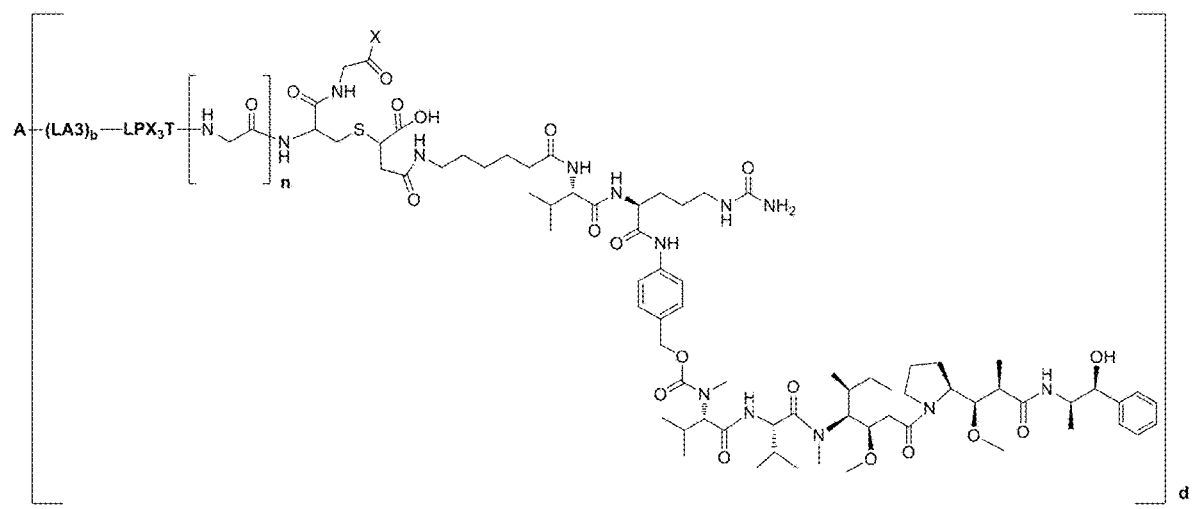
Figure 32A:
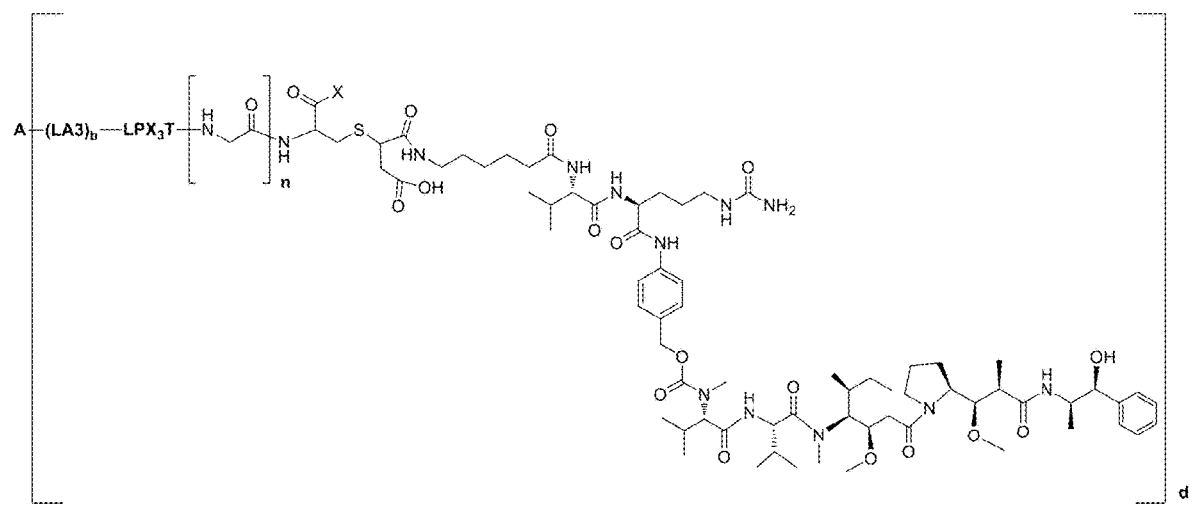
FIG. 32A and FIG. 32B. The molecular schematic diagram of preferred ADC6 molecules (n is an integer from 1-100, d is any of the integers from 1-20, X in ligase recognition sequence LPXT of is glutamic acid (E) or any other natural/unnatural amino acid; Ab is an antibody, LA3 is linker moiety, comprising 1 to 100 series-connected structure units which are selected from the group consisting of one or more glycine and alanine; each b is independently 0 or 1, indicating the presence or absence of LA3; x is —OH or —NH$_2$ group.
Figure 32B:
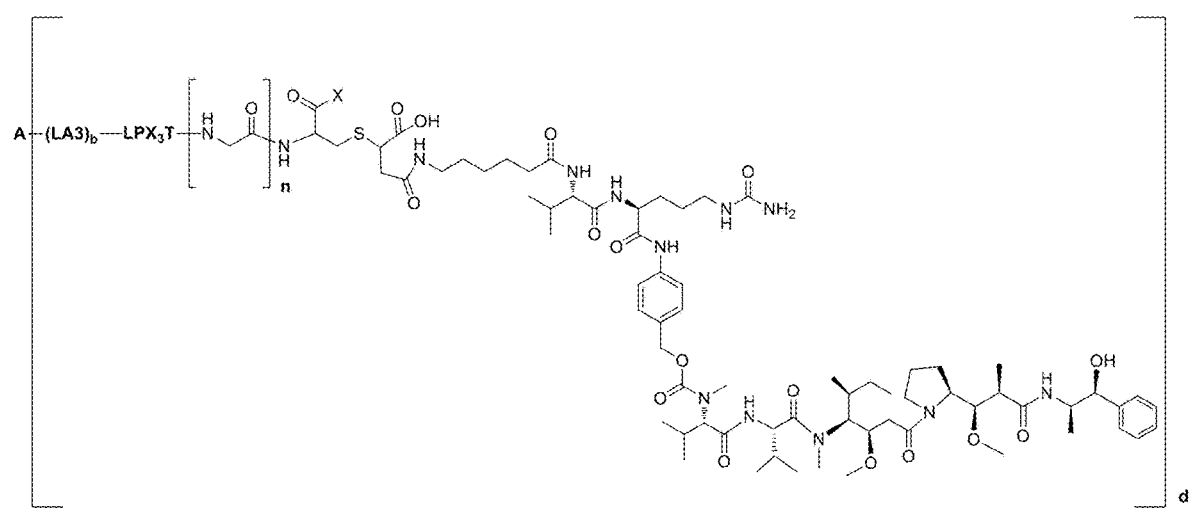

The ADC of this invention is prepared by site-specific coupling of linker 2-DM1intermediate (n=3, the ring-open) with antibody T-LCCT$_L$-HC under the catalysis of a transpeptidase (FIG. 28), wherein, n is 3, d is 2, the X in the ligase recognition sequence LPXT is a glutamic acid (E).

1) The Treatment of Antibody T-LCCT$_L$-HC

The storage buffer of antibody T-LCCT$_L$-HC was exchange to 1× ligase buffer by ultrafiltration, dialysis or desalination. The main component of 1× ligase buffer was 50 mM Tris-HCl (pH 5-8), 150 mM NaCl, with or without CaCl$_2$).

2) Solid-Phase Preparation of ADC GQ1001

The present invention utilizes the coupling reaction of an optimized and engineered transpeptidase catalyzed antibody T-LCCT$_L$-HC based on Sortase with linker 2-DM1 intermediate (n=3, ring-open), to produce the ADC GQ1001.

In the 1× transpeptidase buffer, the antibody T-LCCT$_L$-HC and linker 2-DM1 intermediate (n=3, ring-open) were fully mixed at an appropriate mole ratio (1:1 to 1:100), and the mixture was injected into a solid phase coupling column. There are immobilized transpeptidase on the solid-phase matrix, which catalyze the coupling reaction between antibody T-LCCT$_L$-HC and linker 2-DM1 intermediate (n=3, ring-open). The coupling reaction is carried out at 4-40° C. for 0.5 to 20 hours. After reaction, the reaction mixture was removed from the solid phase coupling column, and treated by ultrafiltration or dialysis to remove unreacted drug intermediates. Purified ADC GQ1001 was stored in the original Kadcyla buffer (10 mM Sodium Succinate, pH5.0; 100 mg/ml Trahelose; 0.1% (w/v) Polysorbate 20; with reference to Kadcyla Formulation), and stored at 4° C. or −80° C.

Example 4—SDS-PAGE Analysis of ADC GQ1001

Figure 38:
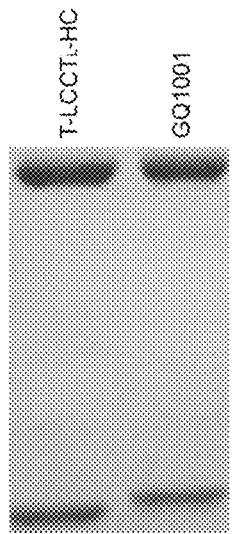
FIG. 38. The SDS-PAGE results of the ADC drug GQ1001 FIG. 39A and FIG. 39B. The high accuracy molecular weight mass spectrometry (ESI-MS) results of ADCs GQ1001 light chain.

The coupling efficiency and purity of GQ1001 can be detected by SDS-PAGE after the coupling reaction. As shown in FIG. 38, the coupling took place on the light chains of antibody T-LCCT$_L$-HC in a site-specific manner, and an obvious molecular weight change was observed for the DM1 coupled light chain of GQ1001, in comparison with the uncoupled T-LCCT$_L$-HC light chain. There is not any uncoupled light chain in the coupled product, which indicating a coupling efficiency as high as 95%. the purity of the coupled product is in consistent with expectation.

Example 5—The High Accuracy Molecular Weight Mass (ESI-MS) Analysis of ADC GQ1001

Figure 39A:
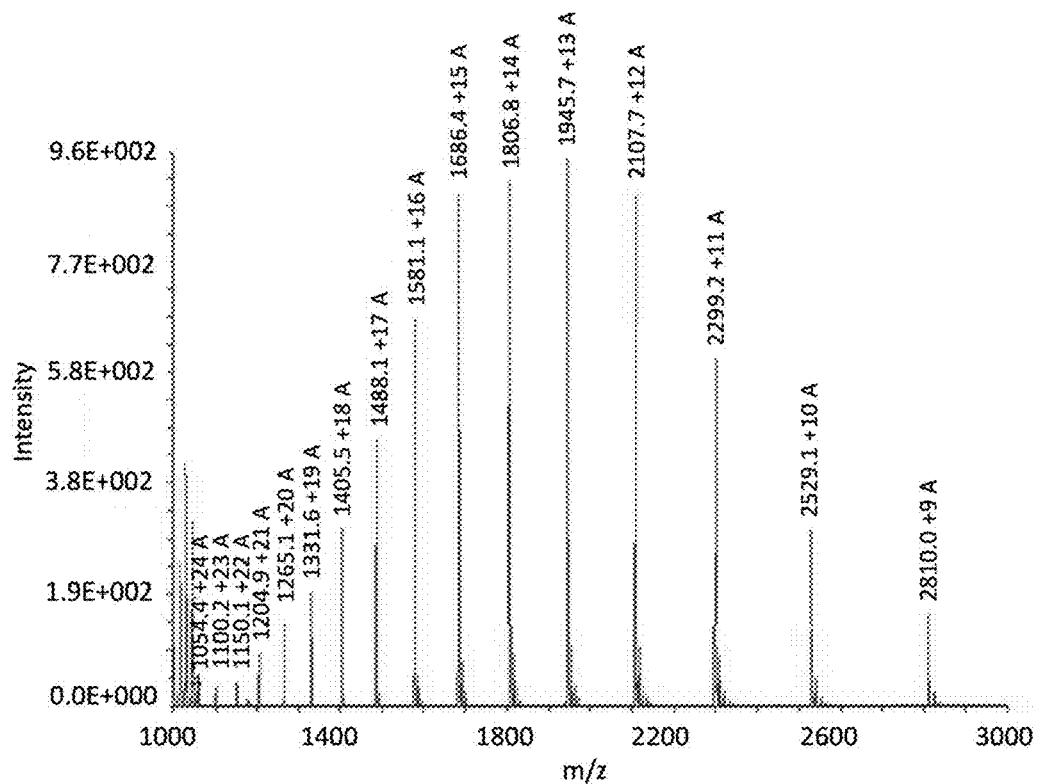
FIG. 39A, light chain spectrum.
Figure 39B:
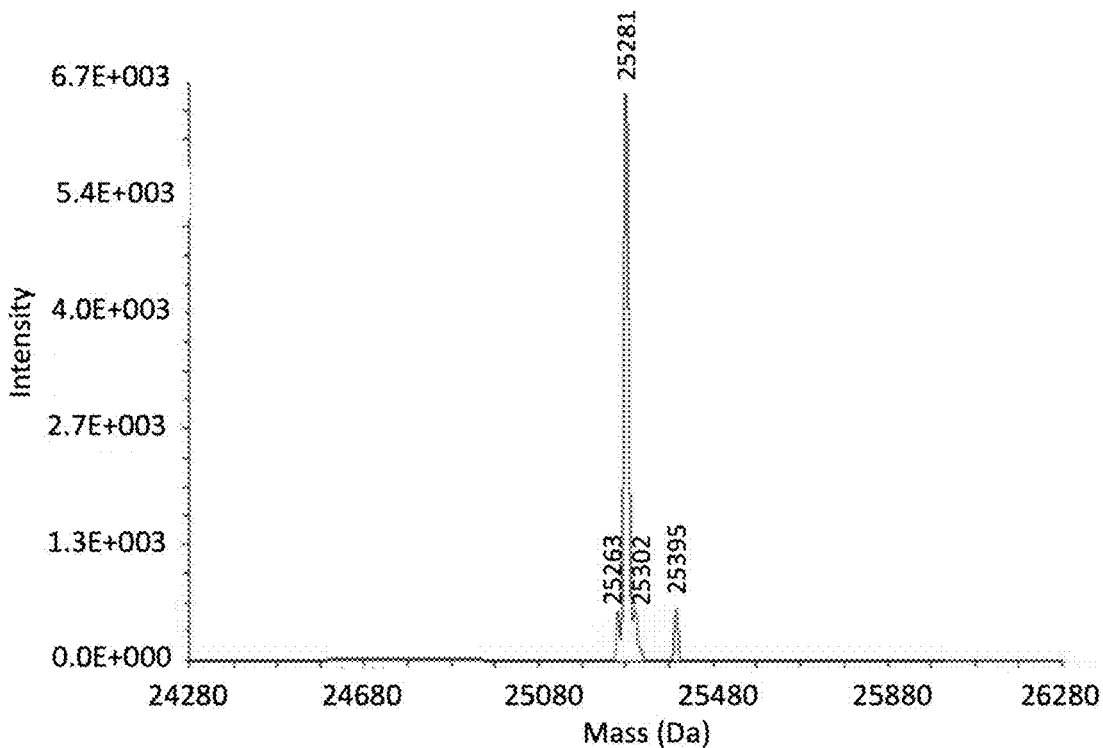
FIG. 39B, Relative molecular weight of light chain (25281) after deconvolution with software ProMass 2.8.

High accuracy molecular weight mass spectrometry was used to analyze the light chain of ADC GQ1001, and the results showed that the apparent mass is 25281, while the theoretical molecular weight is 25284, which is consistent with expectation, confirming that there is a cytotoxin coupled to the end of each light chain. The results of the high accuracy molecular weight mass spectrum (ESI-MS) are shown in FIGS. 39 A and B.

Figure 40:
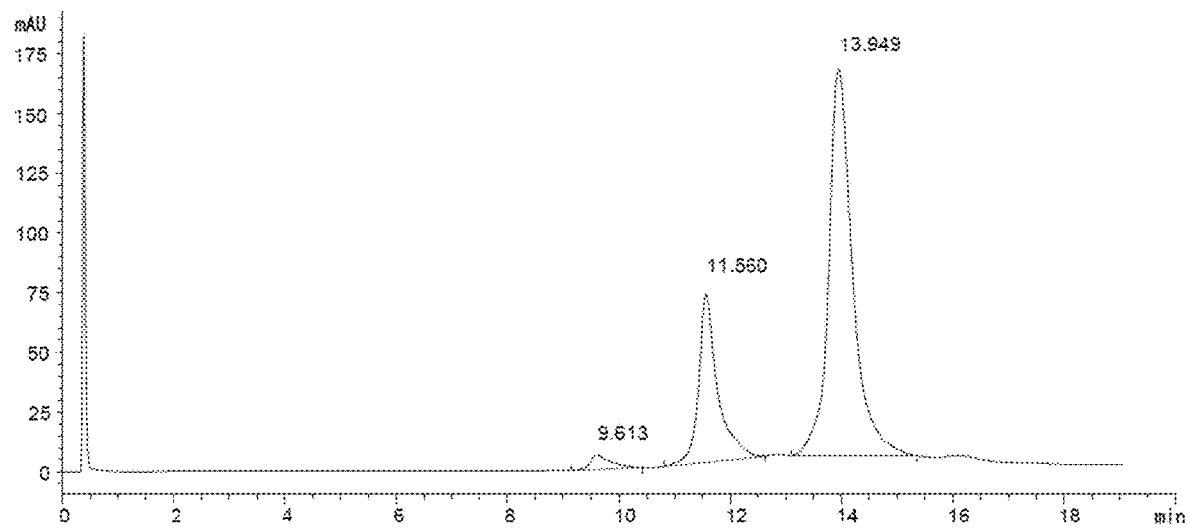
FIG. 40. The HIC-HPLC results of ADC GQ1001.

Example 6-HIC-HPLC analysis of the ADC GQ1001 Butyl-HIC column is used to detect the DAR distribution of ADC GQ1001, and the result is shown in FIG. 40. The cytotoxin-free antibody T-LCCT$_L$-HC is less than 5%; the majority of coupled product is GQ1001 with a DAR of 2, and the overall DAR of ADC GQ1001 is about 1.8.

Example 7—SEC-HPLC Analysis of the ADC GQ1001

Figure 41:
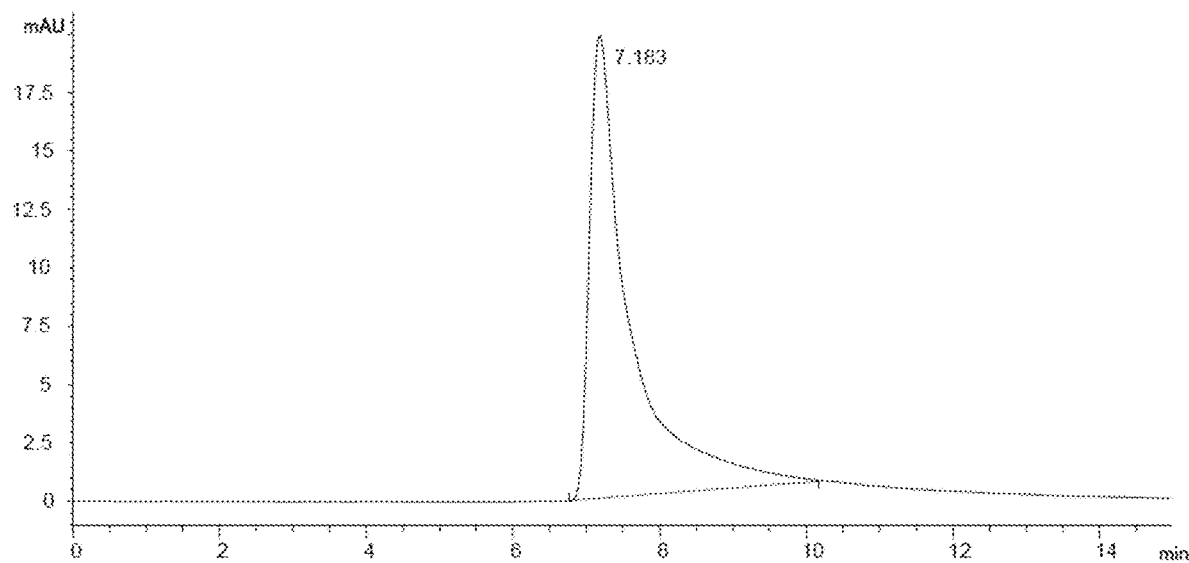
FIG. 41. SEC-HPLC results of ADC GQ1001.

SEC-HPLC was used to detect the degree of high molecular weight aggregation of ADC GQ1001. The result is shown in FIG. 41, high molecular weight polymer is not found in the ADC GQ1001, which indicated the damage caused by the coupling reaction is almost negligible.

Example 8—The Binding Affinity of ADC GQ1001 to the Cell Surface ErbB2/Her2

1) Human breast cancer BT-474 cells or SK-BR-3 cells were collected and made into single cell suspension, adjusted the cell density to (0.5-5)×10$^6$/ml. Take 5×10$^5$ cells/test, and 6.25 nM of Herceptin, T-LCCTL-HC, or GQ1001 was added respectively. The mixture was incubated at 4° C. for 60 min. 1 ml washing solution (PBS+1% BSA) was added, centrifuged at 1000 rpm for 5 min, and the supernatant was removed. The treatment was repeated twice.

Figure 42:
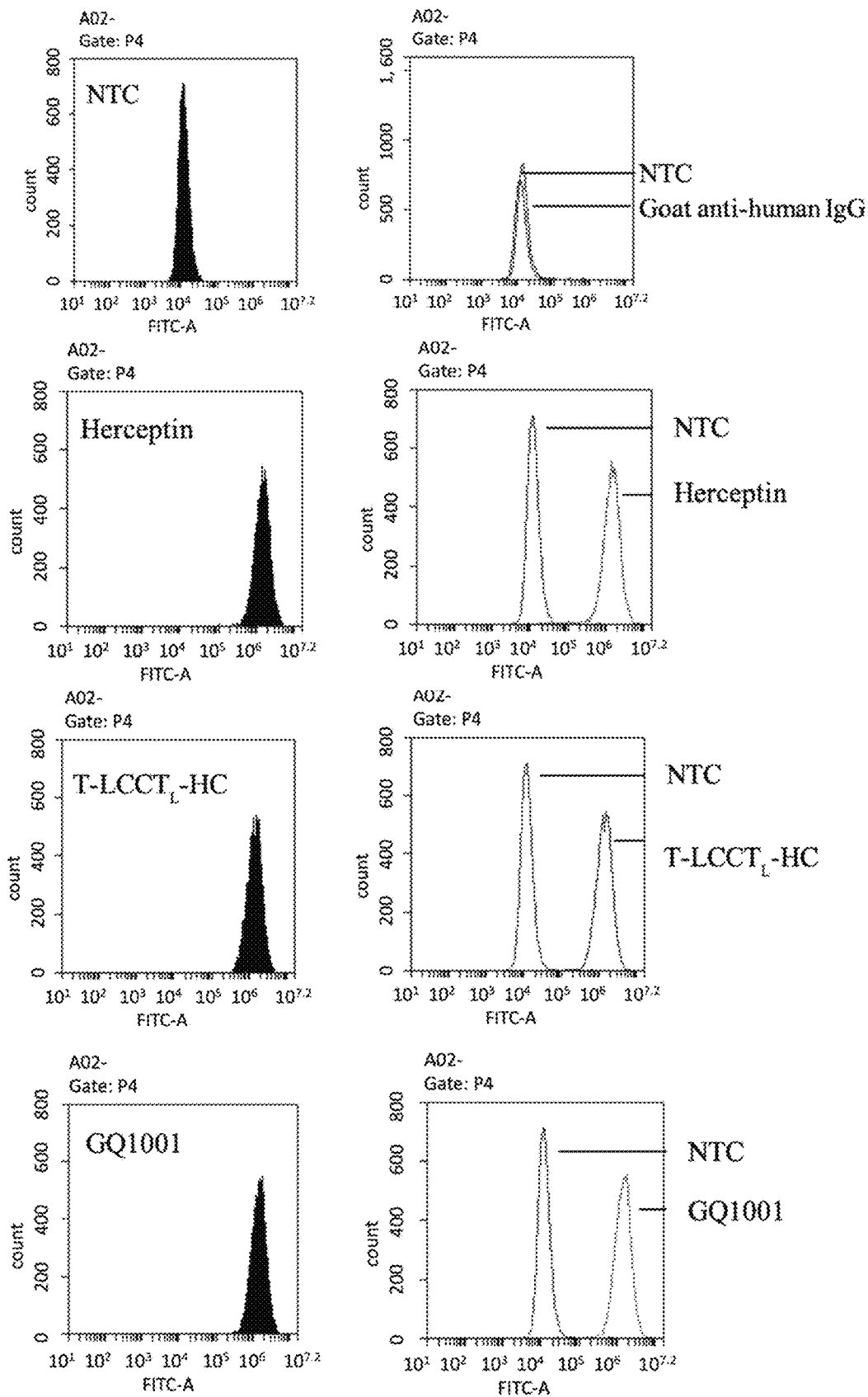
FIG. 42. The binding affinity of ADC GQ1001 with BT474 cell surface ErbB2/Her2 receptor.
Figure 43:
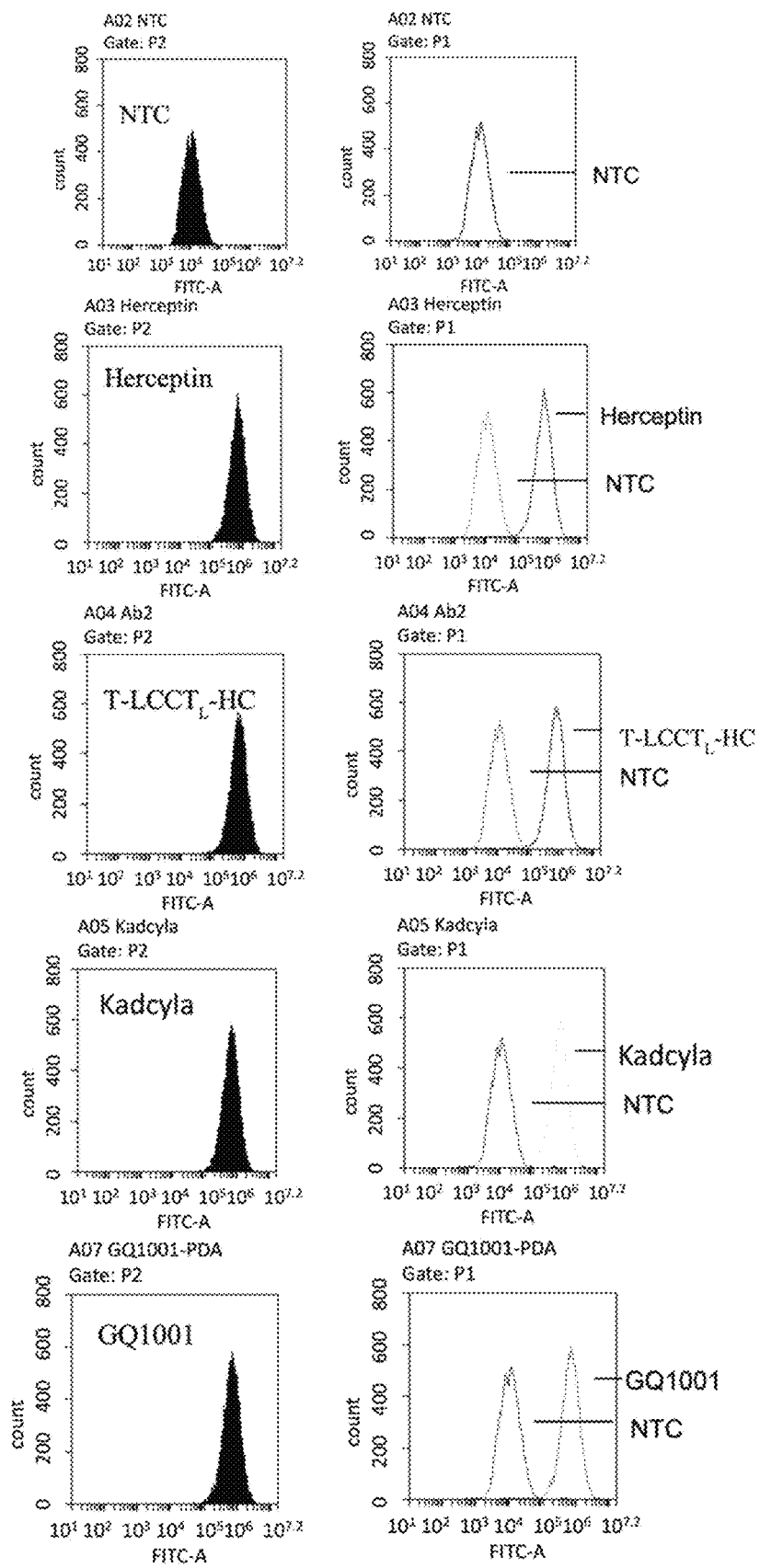
FIG. 43. The binding affinity of ADC GQ1001 with SK-BR-3 cell surface ErbB2/Her2 receptor.
Figure 44:
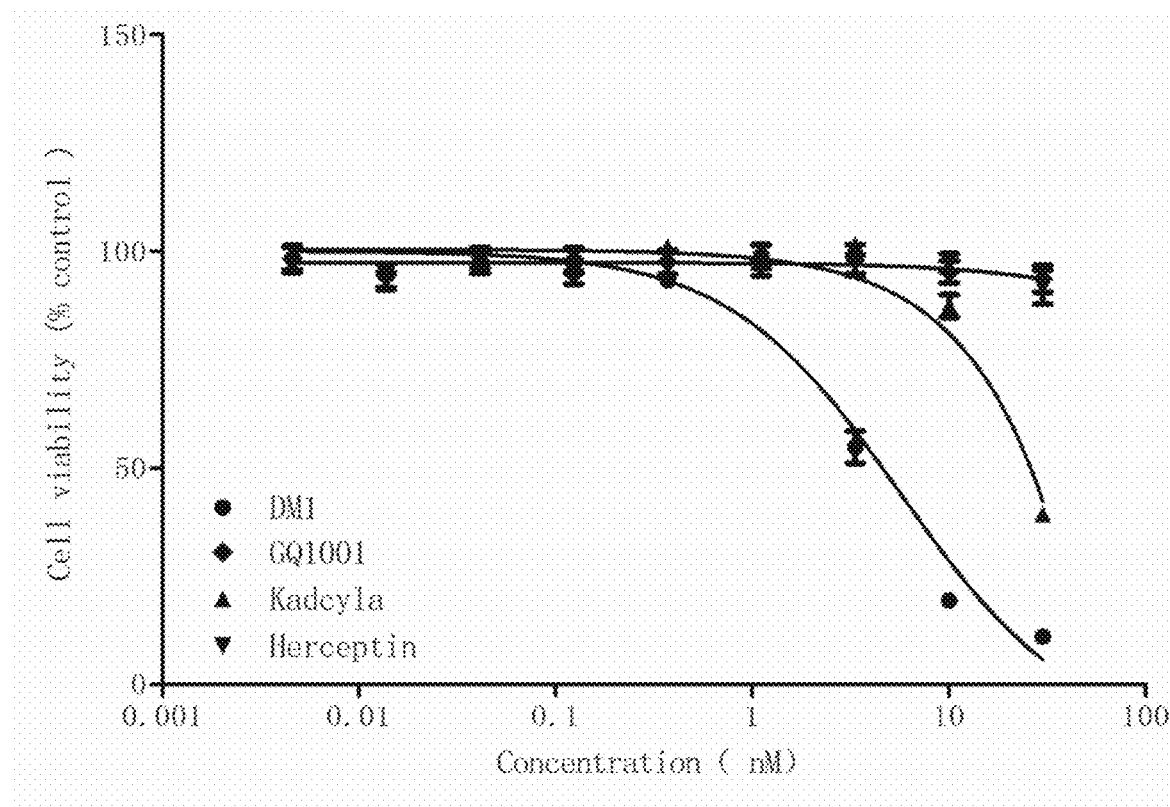
FIG. 44. The effect of GQ1001, Kadcyla, Herceptin, DM1 on MCF-7 cell proliferation.
Figure 45:
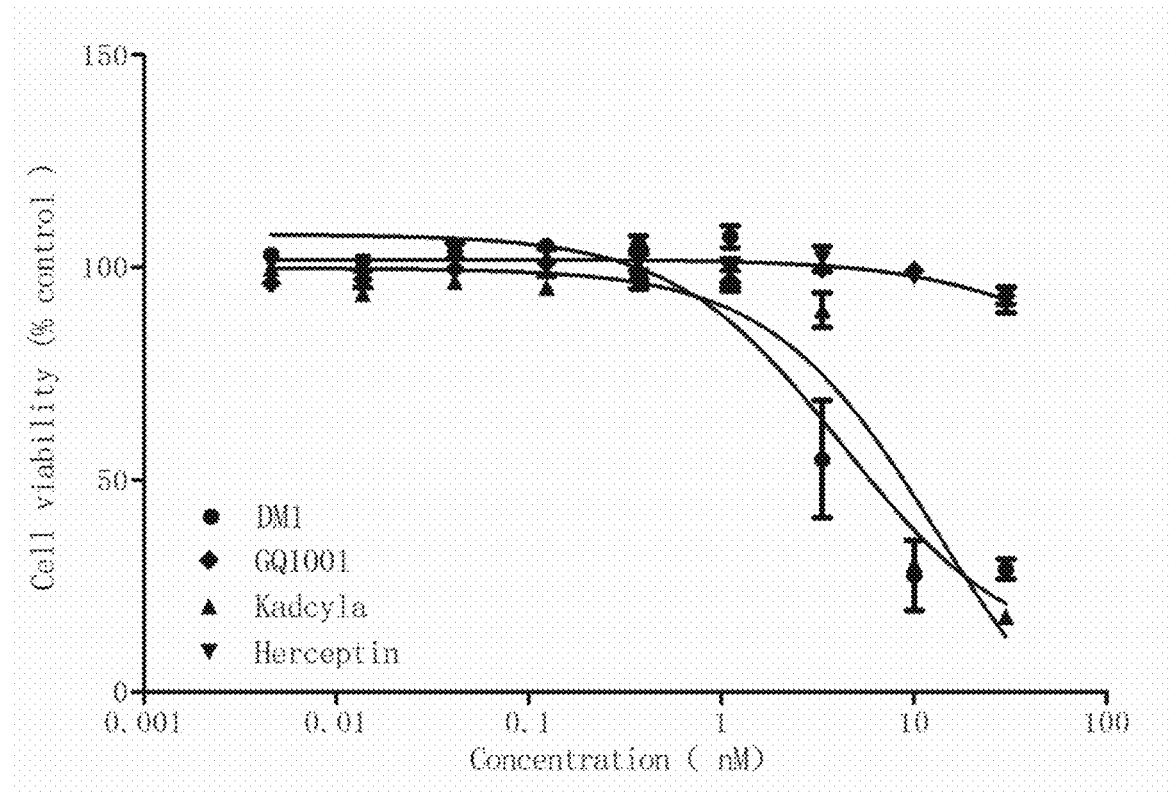
FIG. 45. The effect of GQ1001, Kadcyla, Herceptin, DM1 on MDA-MB-468 cell proliferation.
Figure 46:
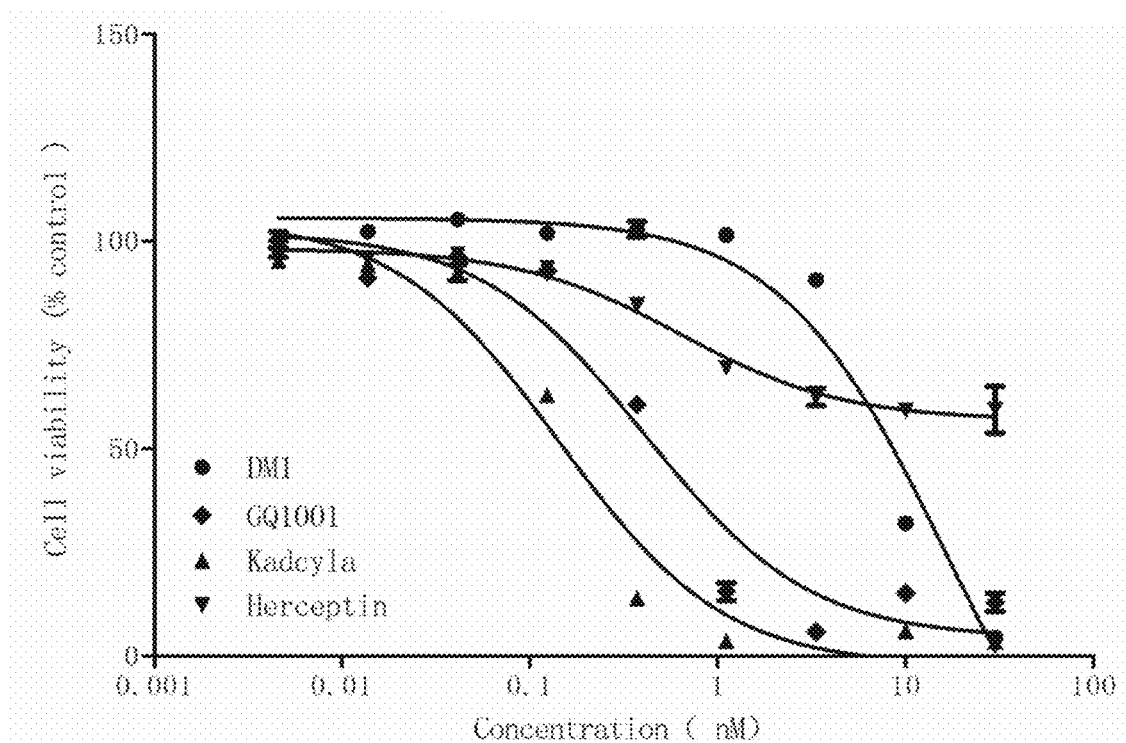
FIG. 46. The effect of GQ1001, Kadcyla, Herceptin, DM1 on BT-474 cell proliferation.
Figure 47:
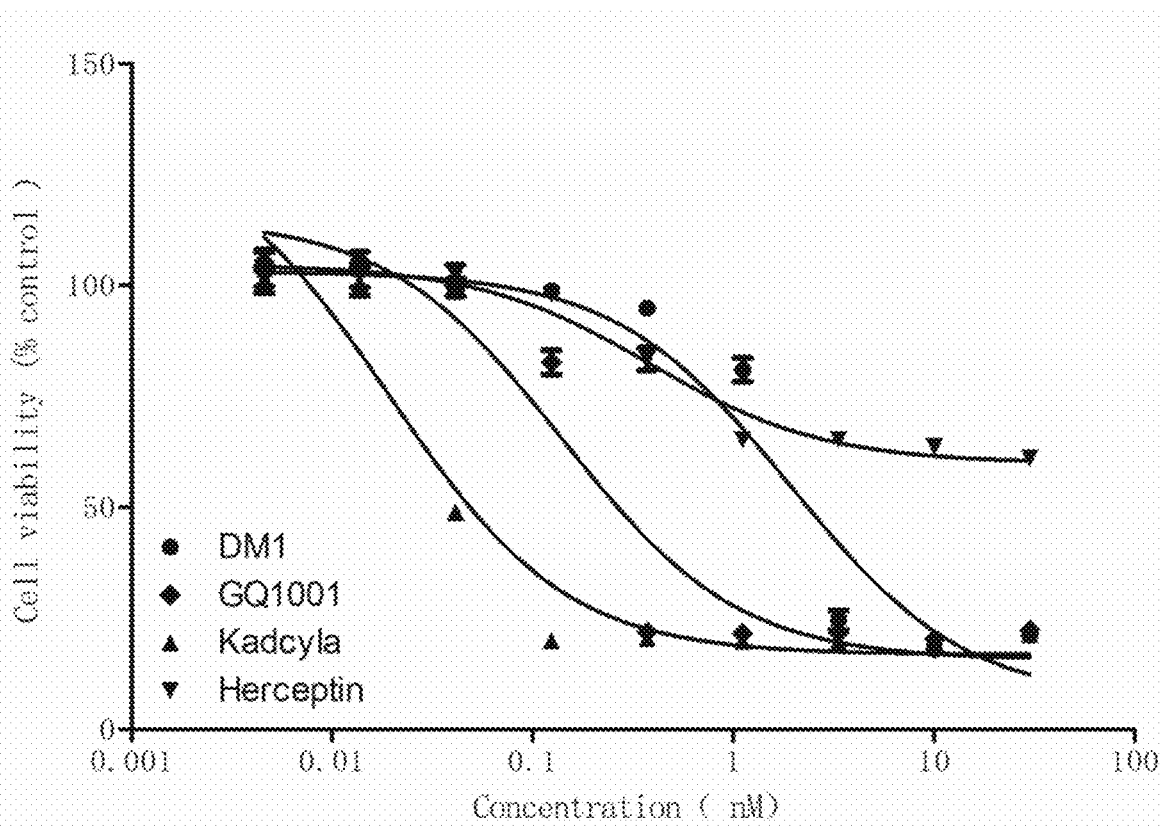
FIG. 47. The effect of GQ1001, Kadcyla, Herceptin, DM1 on SK-BR-3 cell proliferation.
Figure 48:
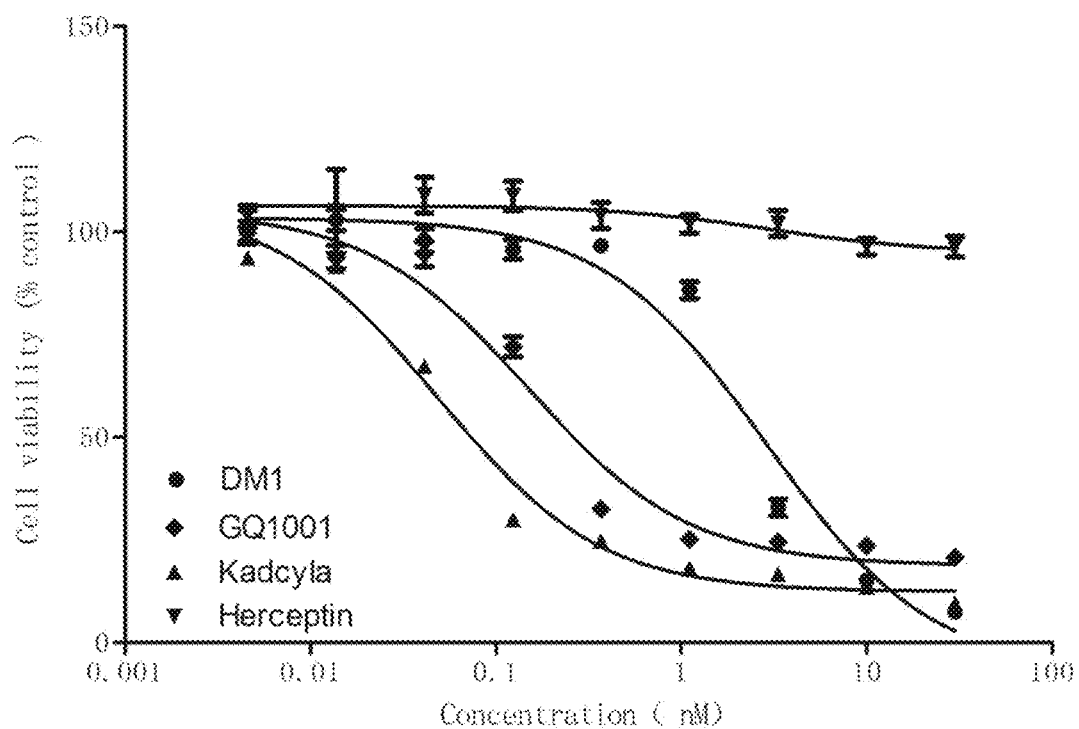
FIG. 48. The effect of GQ1001, Kadcyla, Herceptin, DM1 on HCC1954 cell proliferation.
Figure 49:
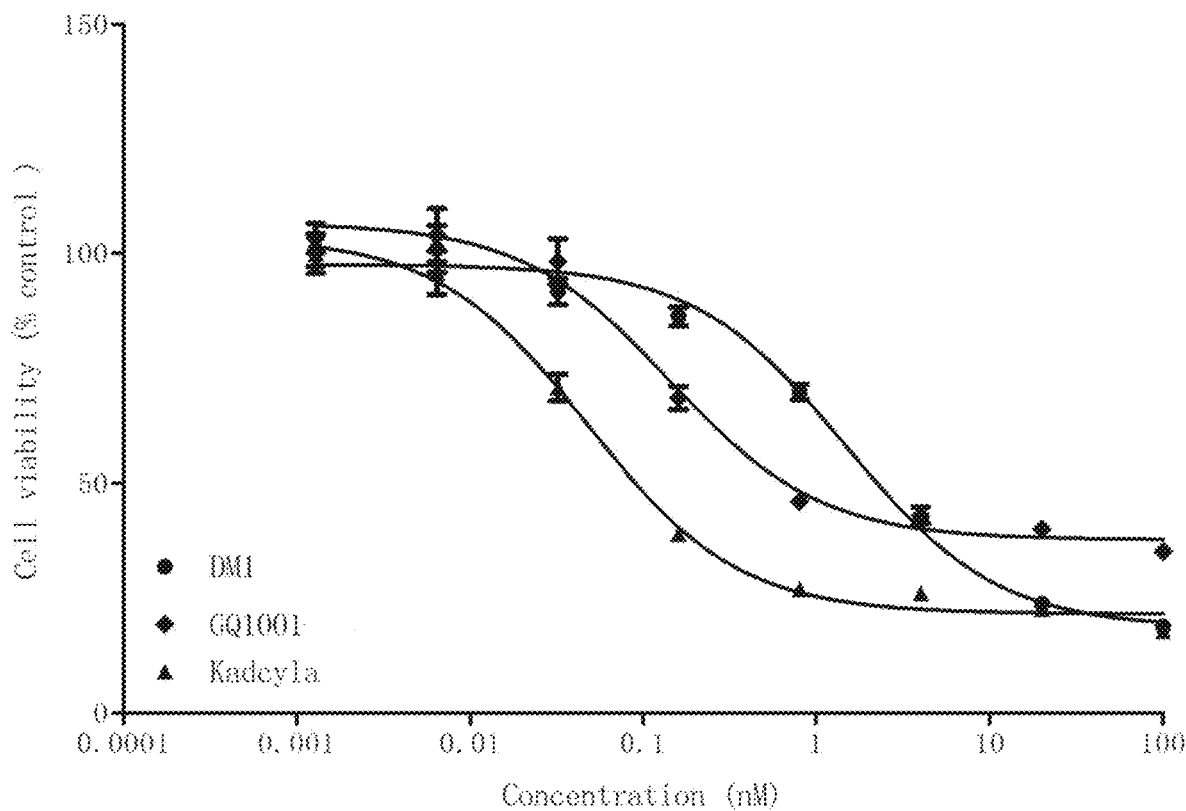
FIG. 49. The effect of GQ1001, Kadcyla, DM1 on SK-OV-3 cell proliferation.
Figure 50:
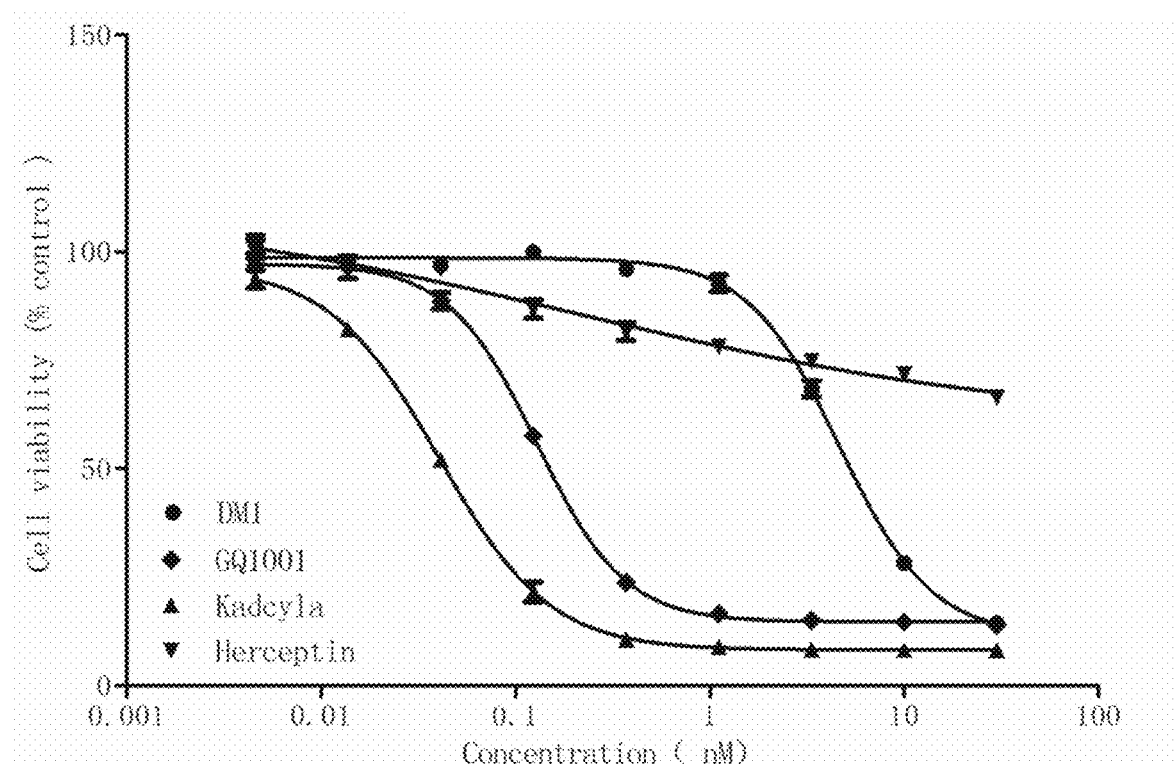
FIG. 50. The effect of GQ1001, Kadcyla, Herceptin, DM1 on NCI-N87 Cell Proliferation.

2) 100 μL FITC-Goat anti-human IgG antibody dilution was added to Herceptin, T-LCCTL-HC and GQ1001 incubated cells respectively, incubated at 4° C. for 30 min in dark. 1 ml washing solution was added, centrifuged at 1000 rpm for 5 min, and the supernatant was removed. The treatment was repeated twice. The cells are resuspended in 500 μL PBS, pass through a 300 mesh sieve, and stored in an ice box in dark, flow cytometer detection was carried out by the BD C6. The results were shown in FIGS. 42-43, The binding affinity of Herceptin, T-LCCT$_L$-HC, GQ1001 to the ErbB2/Her2 receptor on the surfaces of BT-474 and SK-BR-3 cells has no significant difference.

Example 9—The Effect of ADCs GQ1001 on the Proliferation of Tumor Cells with Different Levels of ErbB2/Her2 Expression 1) ErbB2/Her2 low expressing human breast cancer cells MCF-7, MDA-MB-468, ErbB2/Her2 high expressing human breast cancer cells BT-474, SK-BR-3, HCC1954, human ovarian cancer cells SK-OV-3, human gastric cancer cell NCI-N87 was seeded into a 96-well plate at 100 μl/well (containing 1000 to 10000 cells), and incubated in a cell culture incubator overnight (37° C., 5% CO2, 95% air, 100% humidity).

2) The cells incubated overnight was added GQ1001, Kadcyla, Herceptin, and DM1 at different concentrations (30, 10, 3.333, 1.111, 0.370, 0.123, 0.041, 0.014, 0.005 nM), the control group was added 50 μM Puromycin, incubated at 37° C. for a further 48~96 h.

3) The cell plate was removed from the incubator, equilibrated for about 30 minutes to room temperature. Each well was added 100 μl CellTiter Glo reagent, shocked in an oscillator for 2 min, then left stand for 10 min at room temperature in dark, the relative light units (RLU) is measured with a BioTech Gen5 microplate reader.

4) The results of effects of different drugs on the inhibition of tumor cell proliferation are shown in Table 1 and FIGS. 44-50. DM1 has a significant inhibition effect on the proliferation of all cells, either with high or low ErbB2/Her2 expression, but Herceptin and GQ1001 only have a significant inhibition effect on the proliferation of cells with high ErbB2/Her2 expression, and no significant inhibition was observed for cells with low ErbB2/Her2 expression. Kadcyla only inhibits the proliferation of cells with low ErbB2/Her2 expression at high concentrations.

TABLE 1

| | Inhibition effects of different drugs on tumor cell proliferation (IC$_{50}$, nM) | | | |
|---|---|---|---|---|
| | Drug | | | |
| Cell line | GQ1001 | Kadcyla | Herceptin | DM1 |
| MCF-7 | — | — | — | 5.708 |
| MDA-MB-468 | — | — | — | 4.218 |
| BT-474 | 0.410 | 0.144 | — | 16.270 |
| SK-BR-3 | 0.140 | 0.030 | — | 1.918 |
| HCC-1954 | 0.149 | 0.049 | — | 2.897 |
| SK-OV-3 | 0.144 | 0.049 | — | 1.593 |
| NCI-N87 | 0.113 | 0.031 | 0.229 | 7.185 |

NOTE:
"—" Not measured

Example 10—In Vivo Pharmacokinetic Study in Rats 1) 160~180 g SPF grade female SD rats were randomly divided into GQ1001 group, Kadcyla group and blank control group, with 4 rats in each group.

2) 10 mg/kg GQ1001 (batch number: 20141128, purity>98%) or Kadcyla (Lot N1003), were administered via intravenous injection, and an equal volume of PBS (pH 7.4) was administered for the control group.

3) 100~200 μL blood samples (with no anticoagulant added) were taken from the intraocular angular vein at 1 h, 1 day, 2 days, 3 days, 4 days, 6 days, 8 days, 13 days, 17 days, 21 days, 28 days after the drug administration. The collected blood samples were placed on ice for 1~2 h, then centrifuged at 4000 rpm for 20 min (4° C.), the supernatant was divided into small aliquots and added to new EP tubes, and stored at −80° C. for subsequent use.

4) The total contents of GQ1001 and Kadcyla in serum were detected by ELISA.

Figure 51:
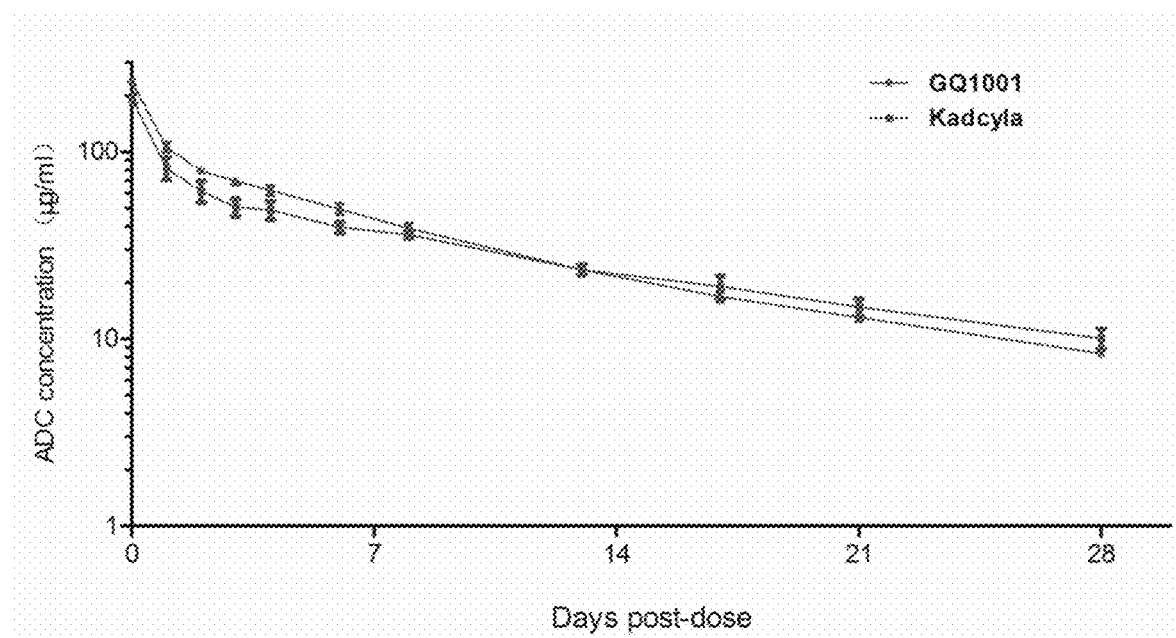
FIG. 51. The pharmacokinetic analysis of rats given a single intravenous injection of GQ1001, Kadcyla. SD rats are injected GQ1001 (10 mg/kg) or Kadcyla (10 mg/kg) via the tail vein, ELISA method is used to detect total ADC concentration in rat serum.

5) The results show that, one day after the administration, the blood concentrations of GQ1001 and Kadcyla decreased rapidly, which were respectively 44.7% and 42.5% of those detected 1 h after administration, no significant difference was observed between the two. This reduction is due to the rapidly systemic distribution of the ADCs after administration. 6 days after administration, GQ1001 and Kadcyla were respectively 20.9% and 20.5% of those detected 1 h after administration; 13 days after administration, GQ1001 and Kadcyla were respectively 9.9% and 12.2% of those detected 1 h after administration. 21 days after administration, GQ1001 and Kadcyla were respectively 5.5% and 7.7% of those detected 1 h after administration. 28 days after the administration, GQ1001 and Kadcyla were respectively 3.5% and 5.2% of those detected 1 h after administration. These results indicate that GQ1001 and Kadcyla showed no significant difference in the attenuation rate in female rats (FIG. 51).

Example 11—In Vivo Pharmacodynamics Evaluation of ADC GQ1001

1) HCC1954 breast cancer cells in the logarithmic growth phase were collected and adjusted with matrigel buffer (PBS: BD Matrigel=1:1) to a cell density of $2.5 \times 10^7$/ml. 0.2 ml of this prepared HCC1954 cell suspension was injected subcutaneously to the right scapula of each BALB/c nude mouse (6 to 8 week-old, SPF grade, female).

2) 7 days after cell inoculation, the diameter of the tumor was measured by caliper and the tumor volume was calculated according to the Formula: $V=0.5a \times b^2$ (a is the longest diameter of the tumor, b is the shortest diameter of the tumor). Animals with tumor volumes of 130~140 mm³ were randomized into 5 groups: the vehicle control group, the GQ1001 0.5 mg/kg, the GQ1001 5 mg/kg group, the Kacyla 5 mg/kg group and the Herceptin 5 mg/kg group, with 10 animals in each group. Administration was via the tail vein injection, and the control group received an equal volume of the vehicle. The tumor size was measured twice a week within 31 days, then once a week afterwards. The tumor volumes at each time point were calculated and compared between groups. At the same time, the T-C or T/C value was used as the index to evaluate the anti-tumor activity of each drug. T-C value is calculated as the follows: T is the average time (Days) when the average tumor volume of each treatment group reaches a preset size (500 mm³), C is the average time (Day) when the average tumor volume of the controlled group reaches the preset size (500 mm³). While T/C (percentage) is the index for tumor inhibition effect, T is the average tumor volume of all the drug treatment groups at a fixed time point, and C is the average tumor volume of the control group at the fixed time point.

Figure 52:
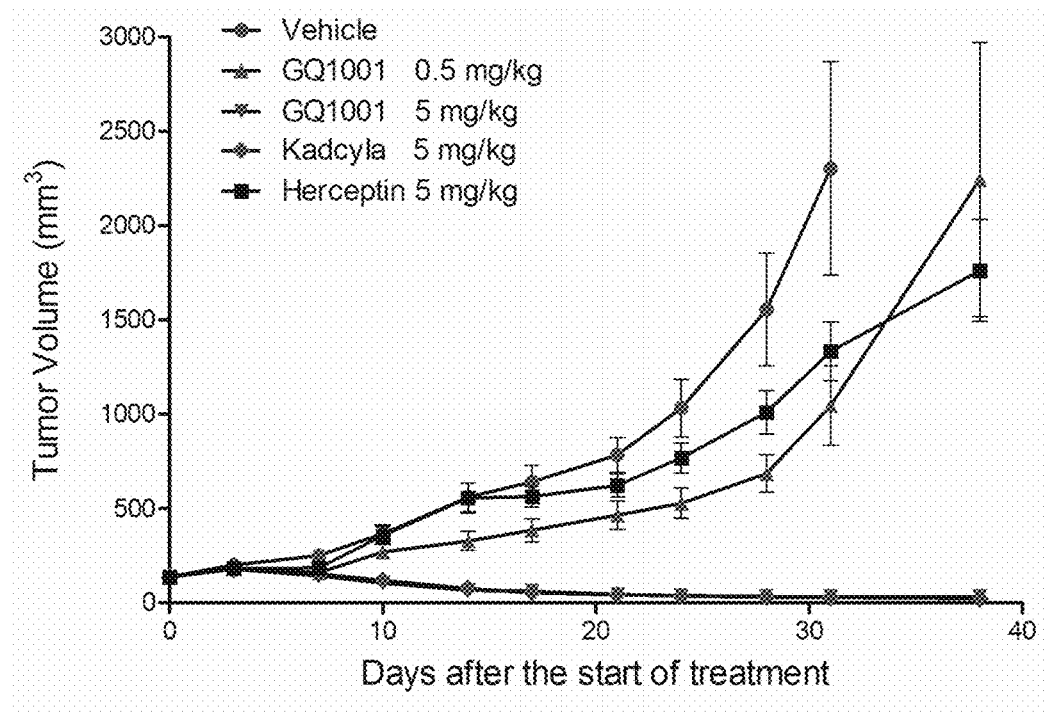
FIG. 52. ADCs GQ1001 inhibit the xenograft tumor in HCC1954 nude mice (n=10, Mean±SEM).

3) The tumor volumes in the GQ1001 5 mg/kg group and Kadcyla 5 mg/kg group were significantly smaller than control group 10 days after administration, and some tumors even became undetectable. No sign of tumor regrowth appeared until the end of the treatment, 38 days after the administration (Table 2, FIG. 52). These results indicate that both GQ1001 and Kadcyla have significant inhibition on ErbB2/Her2 positive breast cancer at the dosage of 5 mg/kg.

TABLE 2

The growth inhibition of ADC GQ1001 on HCC1954 xenograft in mice

| Treatment | Tumor Size (mm³)[a] at day 31 | T/C[b] (%) | T-C (days) at 500 mm³ | p value |
|---|---|---|---|---|
| Vehicle | 2301 ± 566 | — | — | — |
| GQ1001 (0.5 mg/kg) | 1045 ± 211 | 45.4 | 7 | 0.359 |
| GQ1001 (5 mg/kg) | 34 ± 6 | 1.5 | >17 | 0.026 |
| Kadcyla (5 mg/kg) | 29 ± 4 | 1.3 | >17 | 0.026 |
| Herceptin (5 mg/kg) | 1333 ± 155 | 57.9 | 3 | 0.587 |

[a]Mean ± SEM.
[b]Tumor Growth Inhibition is calculated by dividing the group average tumor volume for the treated group by the group average tumor volume for the control group (T/C).

Example 12—Toxicity Studies of Single Injection of ADC GQ1001

1) Healthy adult female SD rats were randomly divided into four groups (n=6/group): the vehicle control group (0 mg/kg), the GQ1001 6 mg/kg group, the GQ1001 60 mg/kg group, and the Kadcyla 60 mg/kg group. The drug was administered by a single injection via tail vein. The administration dose is 10 ml/kg, and the administration rate is about 1 ml/min. During the experiment, the animals were subjected to clinical inspection, and were examined for body weight, food intake, blood count, blood biochemical indices. At the end of the experiment, all animals were euthanized, anatomized and checked systematically. All major organs were weighed, organ coefficient was calculated and any visible lesions were recorded.

Figure 53:
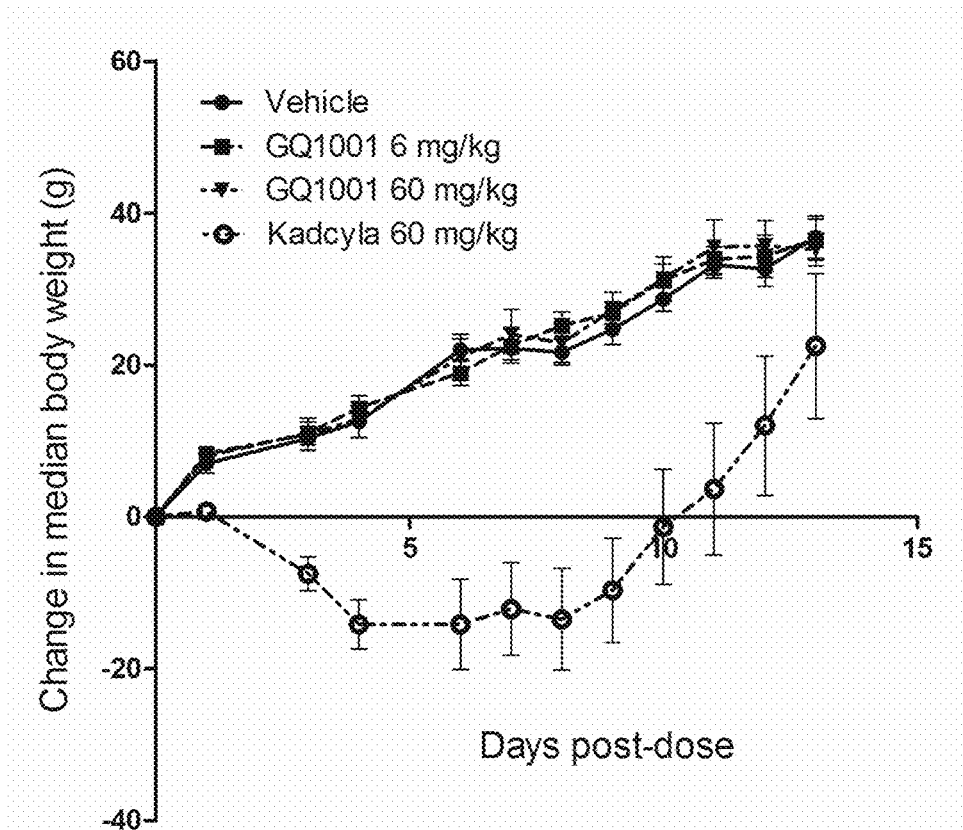
FIG. 53. The weight change of rats after a single intravenous injection of GQ1001 and Kadcyla. Healthy adult female rats are administered GQ1001 (6, 60 mg/kg) or Kadcyla (60 mg/kg) by a single injection via the tail vein. Rats in GQ administration group show no significant difference (P>0.05) in weight gain compared to rats in the vehicle control group, rats in Kadcyla administration group are significantly lower (P<0.05 vs Vehicle) in weight, FIG. 54A and FIG. 54B. The change of ALT (FIG. 54A) and AST (FIG. 54B) level in rats after a single intravenous injection of GQ1001 and Kadcyla. Healthy adult female rats are administered GQ1001 (6, 60 mg/kg) or Kadcyla (60 mg/kg) by a single injection via the tail vein. Rats in GQ1001 administration group show no significant change (P>0.05) in alanine aminotransferase (ALT) and aspartate aminotransferase (AST) compared to rats in the vehicle control group. ALT and AST in rats in Kadcyla administration group are significantly increased (P<0.05 vs Vehicle).

2) The results showed that, during the experiment, no clinical abnormality was observed for any animal in both GQ1001 groups; For the Kadcyla 60 mg/kg group, visible nasal secretions (2/6), ears flushing (ear portions) and swelling (6/6), fluffy coat (6/6), weight loss (1/6), arched (1/6), ears and limbs pale (1/6) were observed 5 days after administration (D5); wherein ear swelling disappeared on D6, nasal secretions disappeared on D7; 4 out of the 6 animals went back to normal on D8, and the rest 2 out of the 6 animals went all back to normal before being euthanized on D15 except visible hair fluffy. Compared with the vehicle control group, no change in body weight associated with administration in both GQ1001 groups was observed; while in the Kadcyla 60 mg/kg group, a significant weight loss was observed after administration (D2~D12). The results are shown in FIG. 53.

Figure 54A:
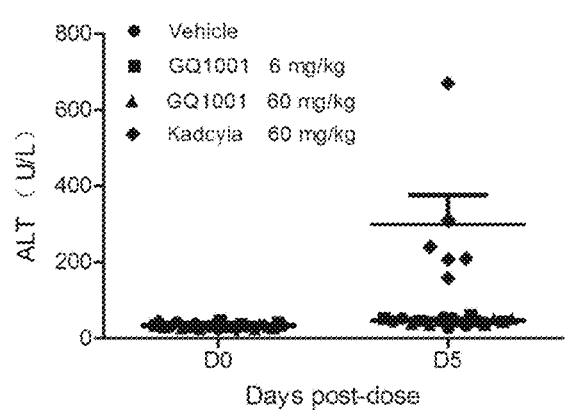
Figure 54B:
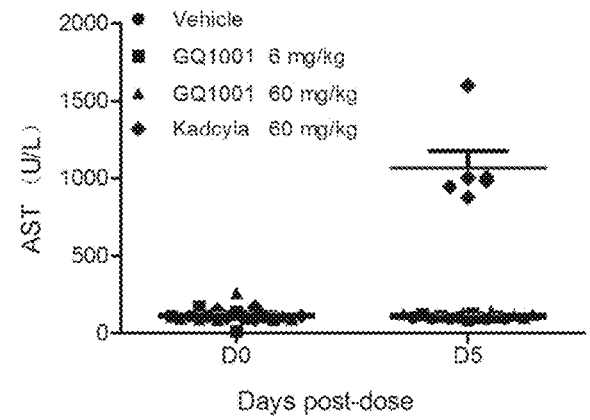

Hematology and clinical biochemical analysis results showed that no significant toxic reaction in both GQ1001 groups, while animals in the Kadcyla 60 mg/kg group had reduced erythroid index (RBC, HGB, HCT, Retic), and increased white blood cell and its subgroup count, ALT, AST, TBIL, GGT increased or had a tendency to increase, especially, the ALT and AST increased significantly, suggesting a drug-related liver toxicity of Kadcyla in a single injection at a dose of 60 mg/kg. The results are shown in FIG. 54.

Systematic anatomy and gross observation showed that, no abnormal changes were observed for animals in each GQ1001 dose group, while general changes associated with administration were observed for animals in Kadcyla 60 mg/kg dose group, including the spleen large (6/6), blunt liver edge round (4/6), thymus (1/6).

The above results suggested that, at the equivalent doses of 60 mg/kg, acute toxicity of GQ1001 is significantly lower than that of Kadcyla.

Example 13—The Preparation of Stable Linker 5-Mc-Val-Cit-Pab-MMAE Drug Intermediate (n=3, Ring-Open)

1) The Preparation and Quality Control of Linker 5-Mc-Val-Cit-Pab-MMAE Drug Intermediate (n=3, Ring-Closed)

Figure 19:
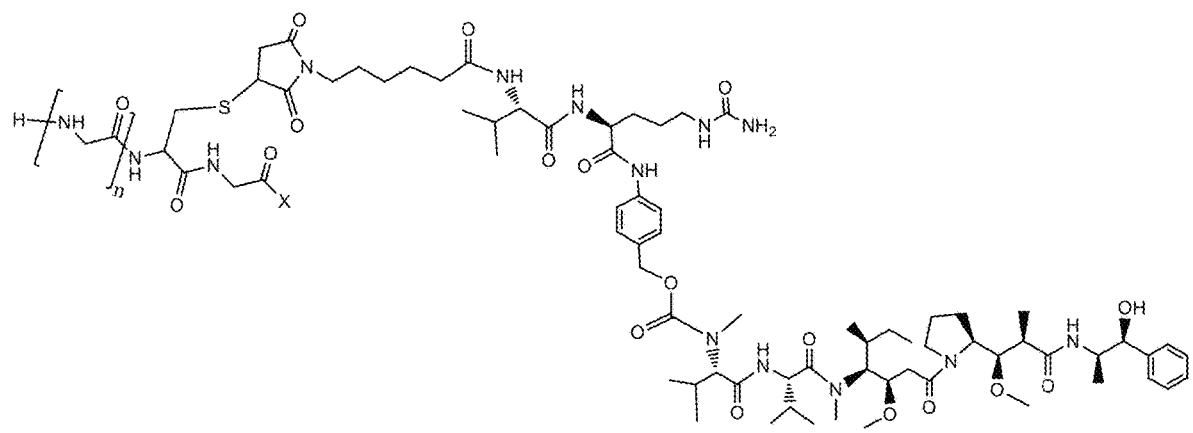
FIG. 19. The chemical structure of linker 5-MMAE intermediate (n is an integer from 1-100, x is —OH or —NH$_2$ groups)
Figure 20:
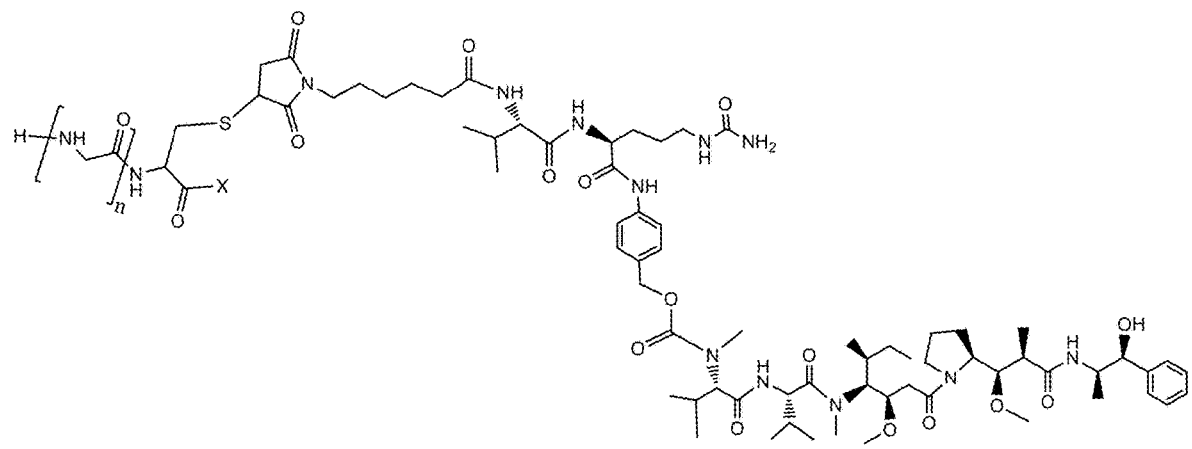
FIG. 20. The chemical structure of linker 6-MMAE intermediate (n is an integer from 1-100, x is —OH or —NH$_2$ groups)
Figure 21:
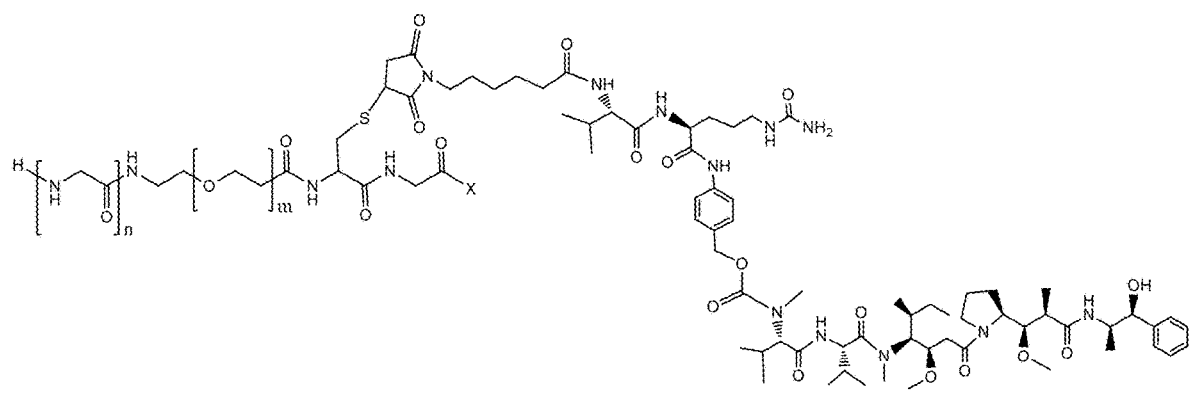
FIG. 21. The chemical structure of linker 7-MMAE intermediate (n is an integer from 1-100, m is 0 or any of the integers from 1-1000, x is —OH or —NH$_2$ group)
Figure 22:
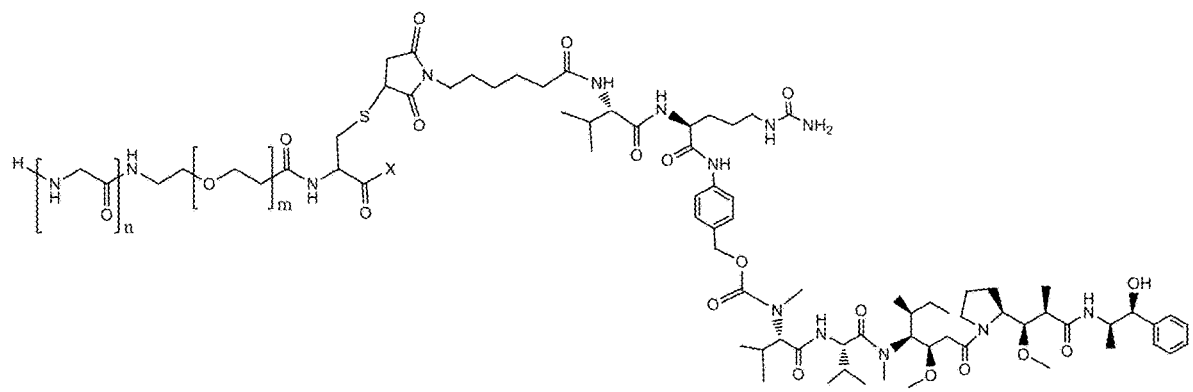
FIG. 22. The chemical structure of linker 8-MMAE intermediate (n is an integer from 1-100, m is 0 or any of the integers from 1-1000, x is —OH or —NH$_2$ group)

Linker 5 (n=3) and Mc-Val-Cit-PAB-MMAE were weighed at 1:1 molar ratio, dissolved and fully mixed, and kept at 0-40° C. for 0.5-20 h, to obtain the linker 5-Mc-Val-Cit-PAB-MMAE (n=3, ring-closed), as shown in FIG. 19.

2) The Ring-Open Reaction of Linker 5-Mc-Val-Cit-PAB-MMAE Drug Intermediate (n=3, Ring-Closed)

Figure 23A:
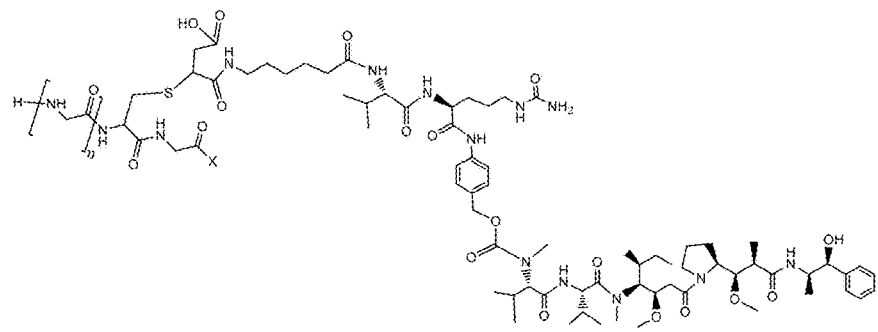
FIG. 23A and FIG. 23B. The ring-open molecular schematic diagram of linker 5-MMAE intermediate (n is an integer from 1-100, x is —OH or —NH$_2$ group.
Figure 23B:
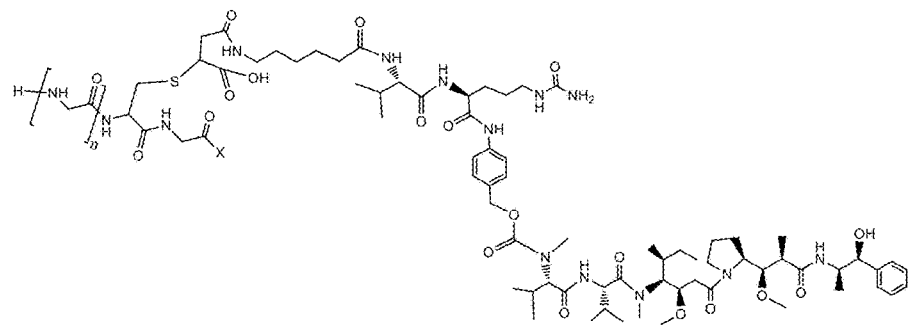
Figure 24A:
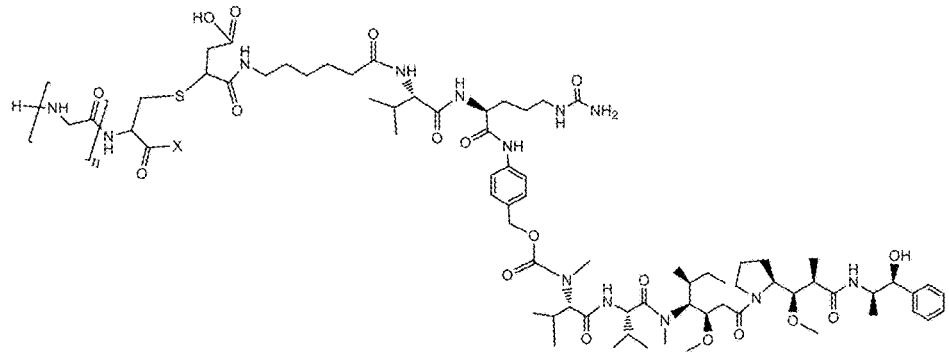
FIG. 24A and FIG. 24B. The ring-open molecular schematic diagram of linker 6-MMAE intermediate (n is an integer from 1-100, x is —OH or —NH$_2$ group.
Figure 24B:
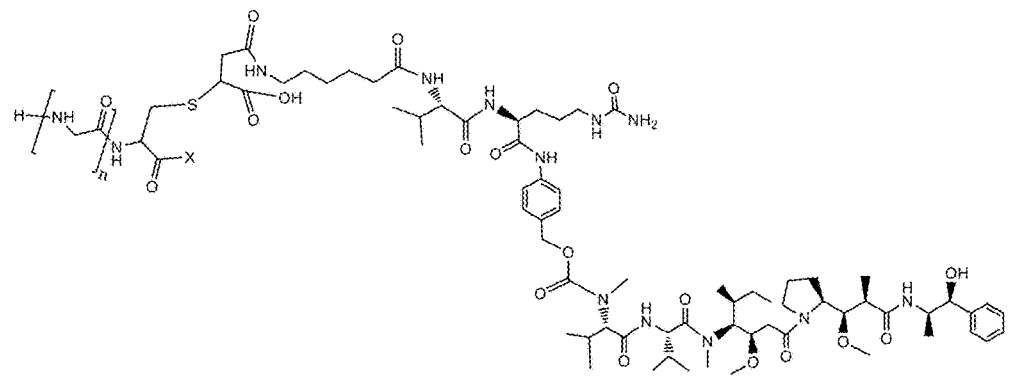
Figure 25A:
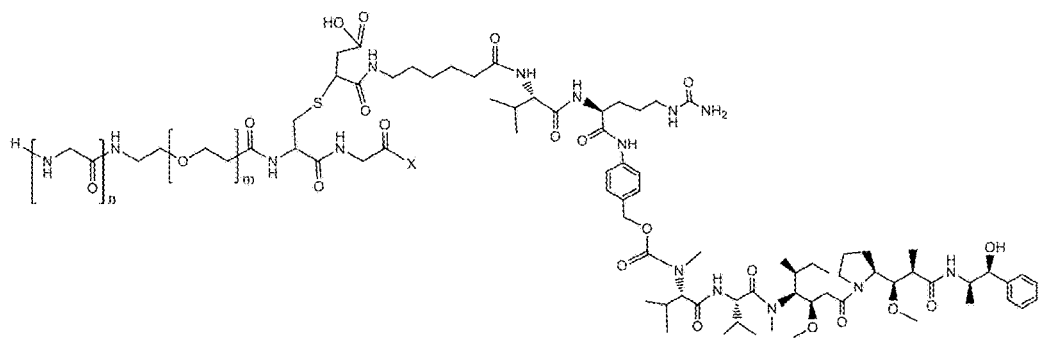
FIG. 25A and FIG. 25B. The ring-open molecular schematic diagram of linker 7-MMAE intermediate (n is an integer from 1-100, x is —OH or —NH$_2$ group, m is 0 or any of the integers from 1-1000.
Figure 25B:
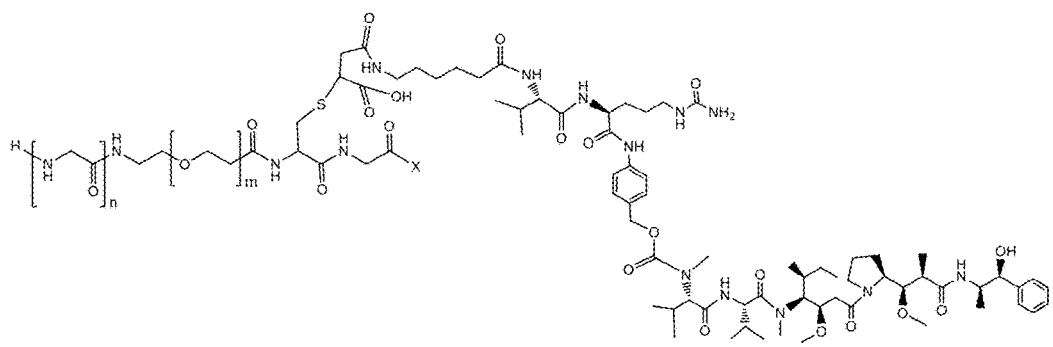
Figure 26A:
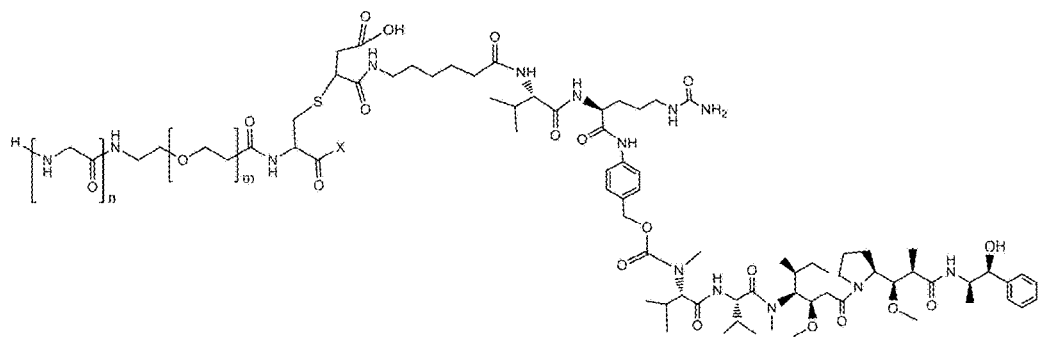
FIG. 26A and FIG. 26B. The ring-open molecular schematic diagram of linker 8-MMAE intermediate (n is an integer from 1-100, x is —OH or —NH$_2$ group, m is 0 or any of the integers from 1-1000.
Figure 26B:
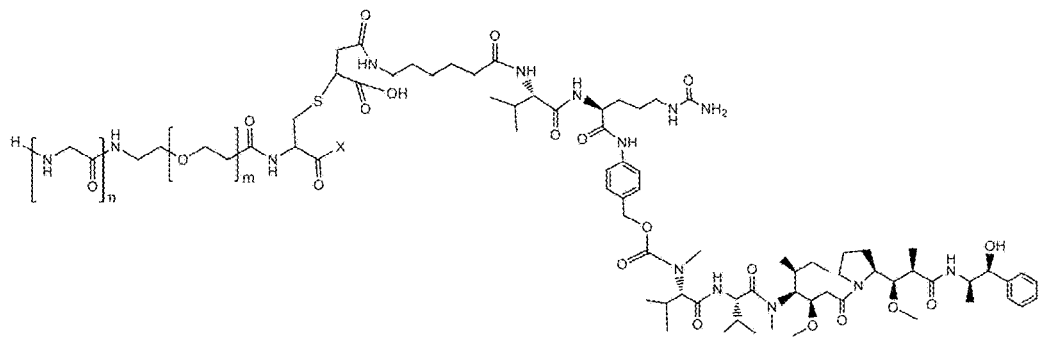
Figure 27A:
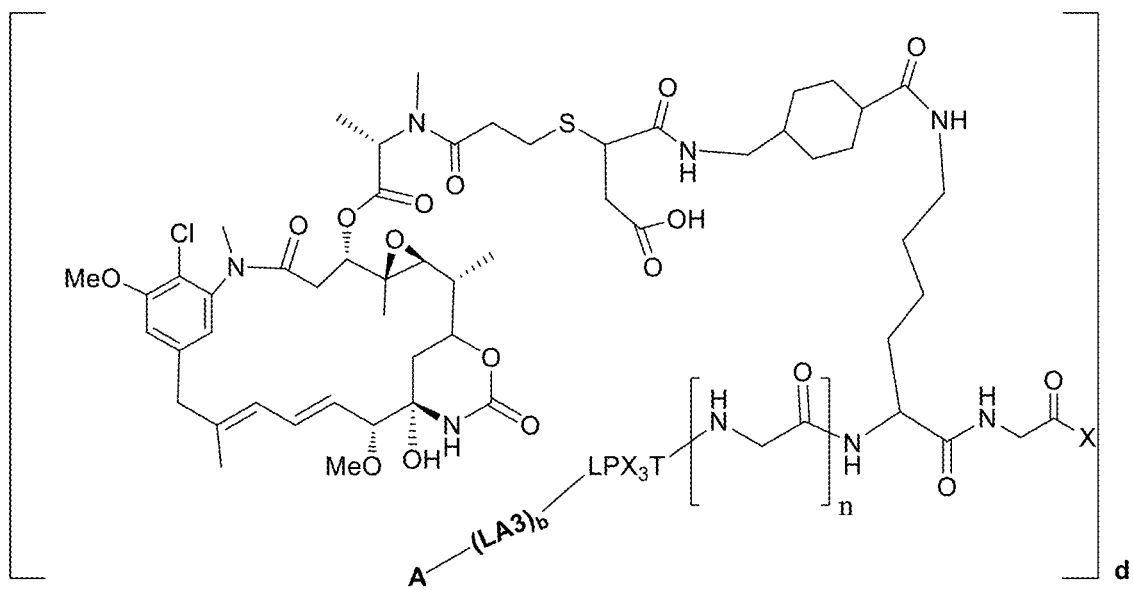
FIG. 27A and FIG. 27B. The molecular schematic diagram of preferred ADC1 molecules (n is an integer from 1-100, d is any of the integers from 1-20, X in ligase recognition sequence LPXT of is glutamic acid (E) or any other natural/unnatural amino acid; Ab is an antibody, LA3 is linker moiety, comprising 1 to 100 series-connected structure units which are selected from the group consisting of one or more glycine and alanine; each b is independently 0 or 1, indicating the presence or absence of LA3; x is —OH or —NH$_2$ group.
Figure 27B:
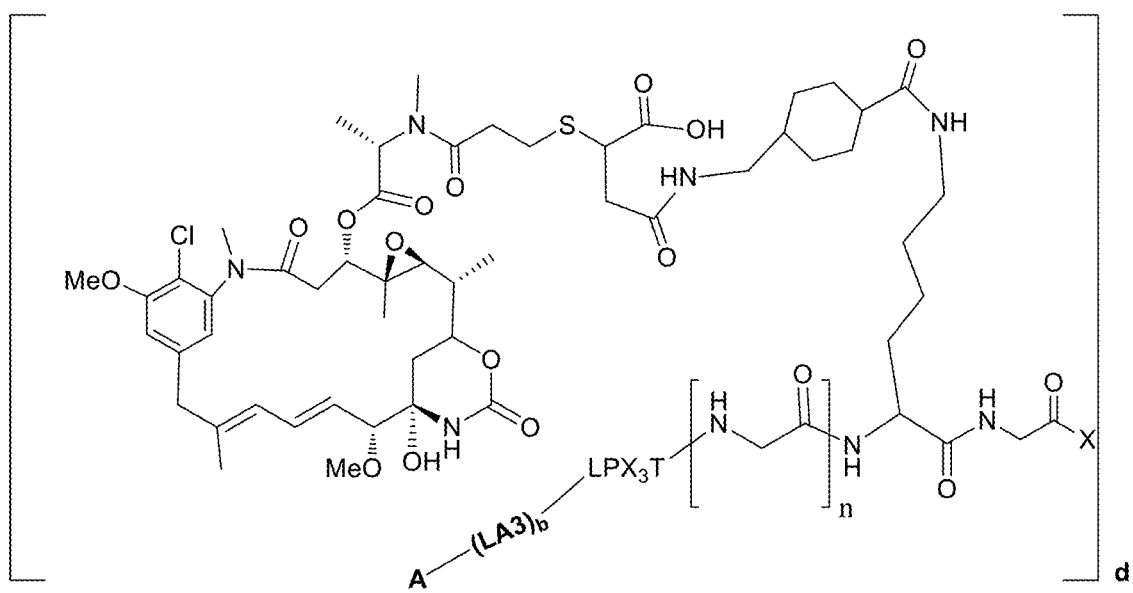
Figure 55:
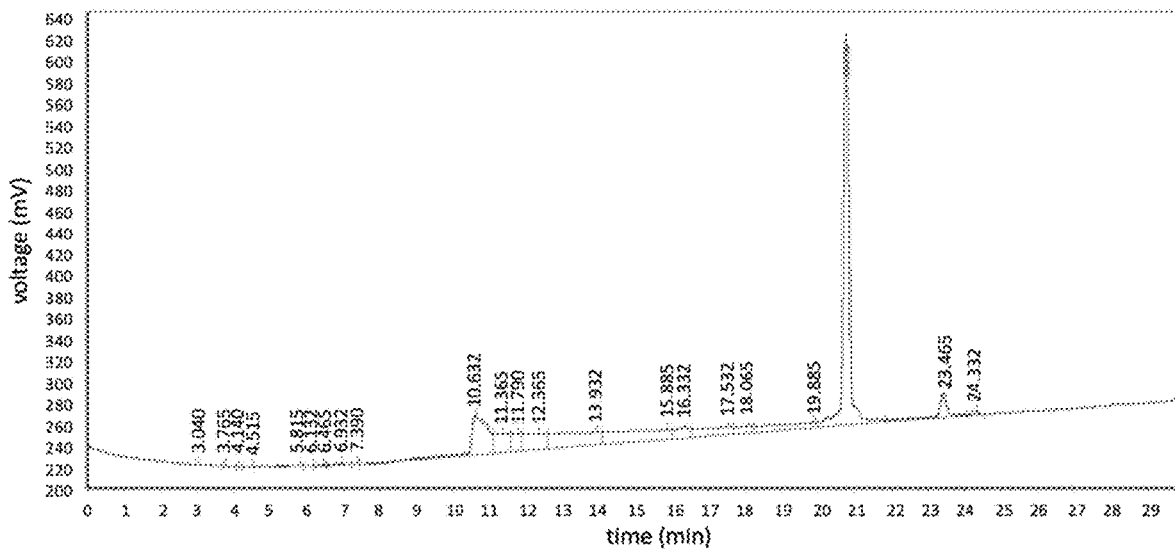
FIG. 55. The HPLC results of a ring-open reap Lion solution of linker c-Val-Cit-Pab-MMAE drug intermediates (n=
Figure 56:
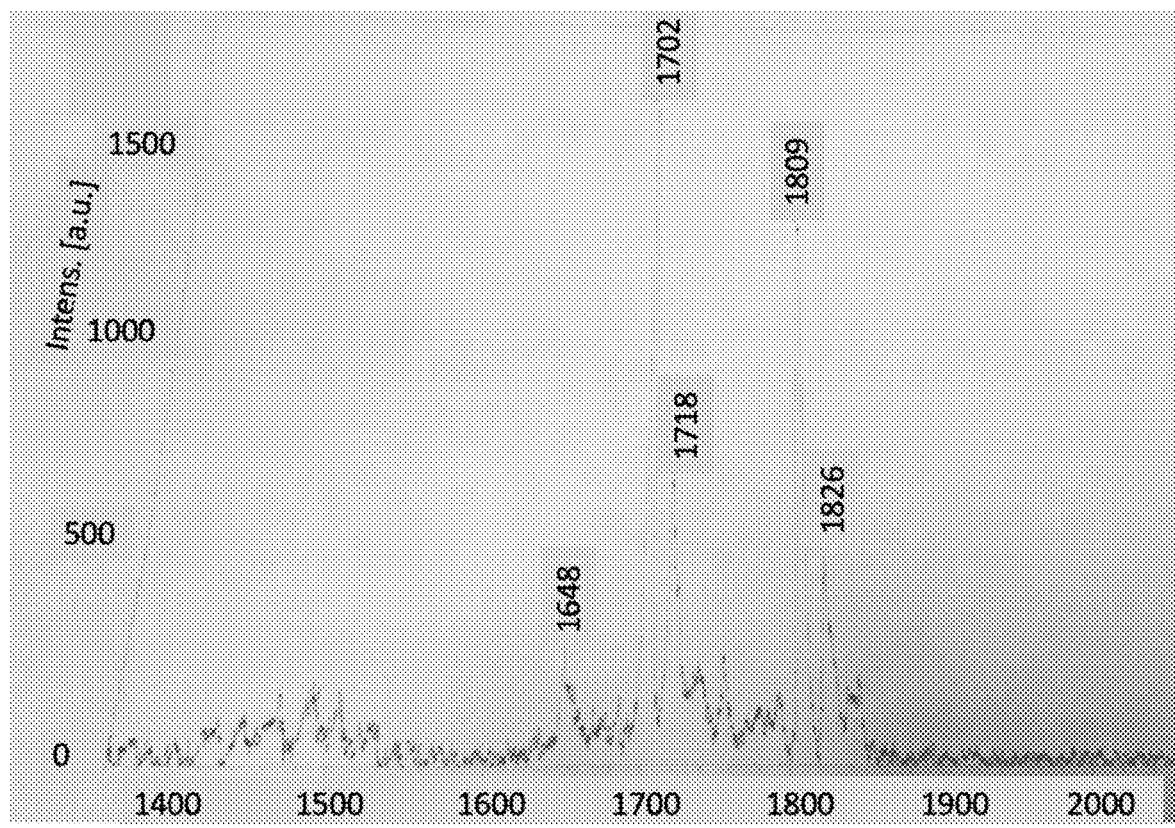
FIG. 56, The MALDI-TOF mass results of a ring-open reaction solution of linker c-Val-Cit-Pab-MMAE drug intermediates (n=3).

Linker 5-Mc-Val-Cit-PAB-MMAE drug intermediate (n=3, ring-closed) was treated with an appropriate amount of Tris Base solution or other solution to promote the ring-open reaction, the reaction was carried out at 0-40° C. for 0.2-20 h, to give the ring-open form of the intermediate as shown in FIG. 23. The purity and molecular weight of the intermediates (ring-open) was analyzed by HPLC, and the results are shown in FIG. 55, the isomers cannot be separated by common HPLC. The MALDI-TOF mass spectrum was used to detect the ring-open reaction mixture and a series of molecule weight was obtained, as shown in FIG. 56, the theoretical mass is 1681, and the found mass is 1702, 1718, corresponding to Na and K salts respectively, fully in consistent with expectation, confirming that an expected ring-opened product was obtained. The preparation of a highly pure ring-open intermediate can be achieved by semi-preparative/preparative HPLC regardless of the succinimide ring-open efficiency, thus ensuring the subsequent use in antibody coupling.

The invention claimed is:

1. A compound of Formula (V) or (VI):

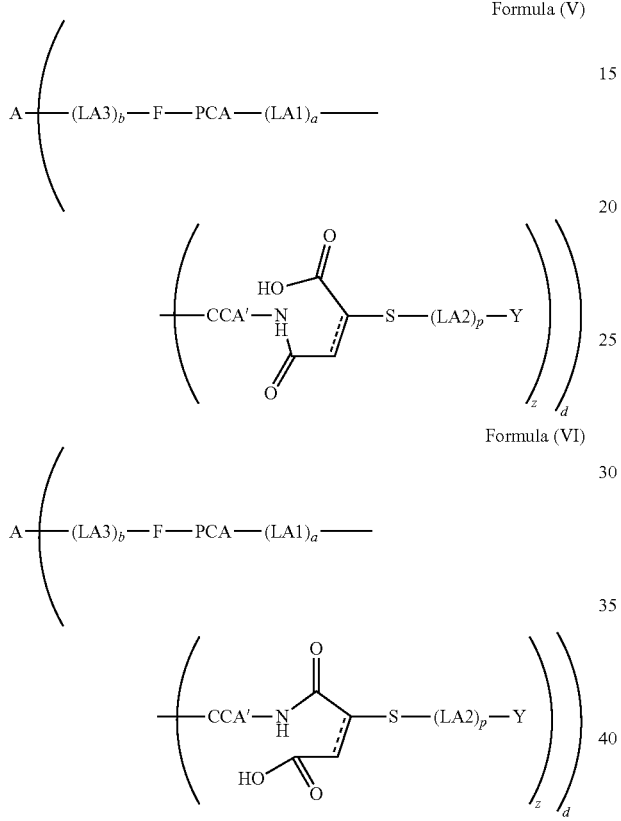

or a pharmaceutically acceptable salt thereof, wherein A is an antibody;

LA1, LA2 and LA3 are each independently linker moieties, with LA3 comprising 1 to 100 series-connected structure units which are selected from the group consisting of one or more glycine and alanine;

a, b and p are independently 0 or 1, that is, LA1, LA2 and LA3 are independently present or absent;

one of PCA and F is a specific recognition sequence of a ligase donor substrate and the other of PCA and F is a specific recognition sequence of the ligase acceptor substrate, wherein by the action of the ligase the PCA can bind specifically to F through an amide bond;

CCA' is a chemical conjugation moiety;

═══ represents a single or double bond;

Y is a radioactive label, a fluorescent label, an affinity purification tag, a tracer molecule, an anticancer drug or a cytotoxic molecule;

z is any of the integers between 1 and 20; and d is any of the integers between 1 and 20 wherein F is $X_1X_2X_3TX_4X_5$, with X being leucine or asparagine, $X_2$ being proline or alanine, $X_3$ being any of the natural or unnatural amino acids, T being threonine, $X_4$ representing glycine, serine or asparagine or being absent, and $X_5$ being any of the natural or unnatural amino acid or being absent; and wherein the PCA comprises 1 to 100 series-connected structure units which are selected from the group consisting of one or more glycine and alanine.

2. The compound according to claim 1, wherein A is anti ErbB2/Her2 antibody.

3. The compound according to claim 2, wherein F is linked to the C-terminus of A's heavy or light chain through LA3 or directly through a covalent bond.

4. The compound according to claim 1, wherein the ligase is a transpeptidase.

5. The compound according to claim 1, wherein F is $LPX_3T$ or $LPX_3TGG$ (SEQ ID NO: 17), with L being leucine, P being proline, $X_3$ being any of the natural or unnatural amino acids, T being threonine and G being glycine.

6. The compound according to claim 1, wherein Y is maytansine, DM1, DM4, paclitaxel, Auristatin, monomethyl auristatin E (MMAE), monomethyl auristatin F (MMAF), monomethyl auristatin D (MMAD), epothilone, or a vinca alkaloid compound.

7. A compound, wherein the compound is selected from the following:

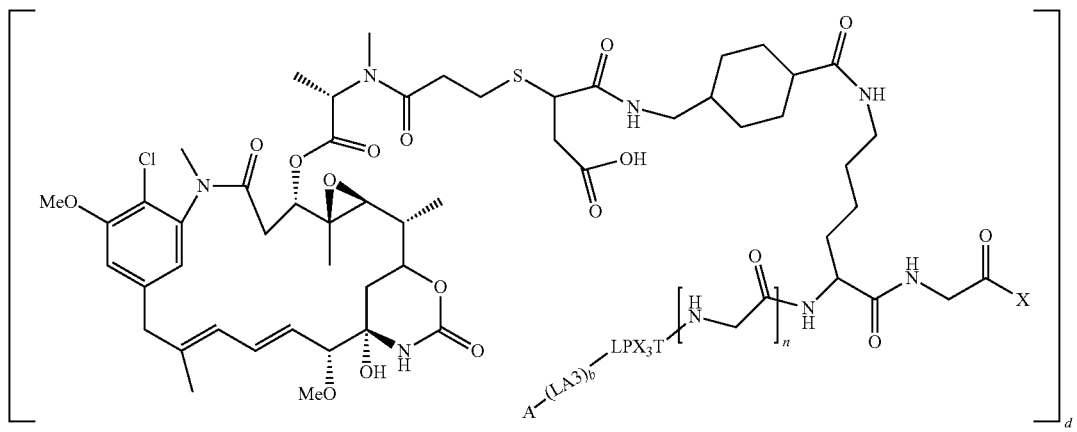

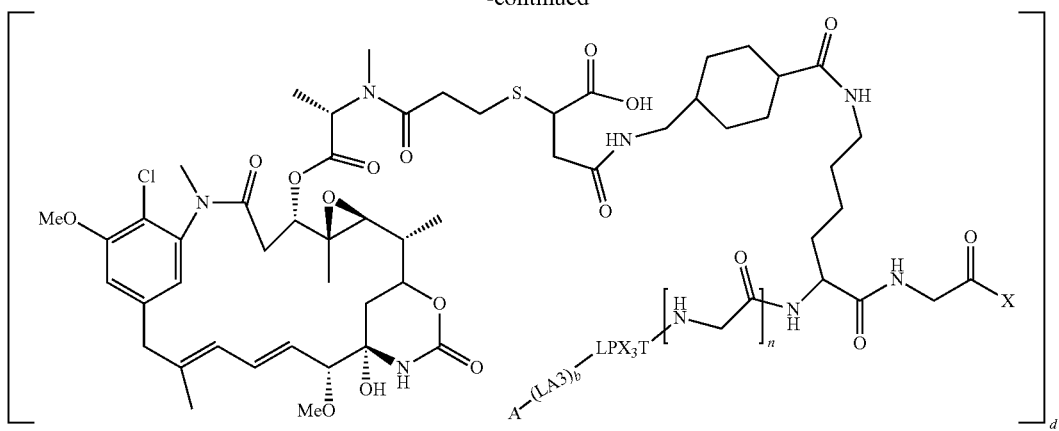
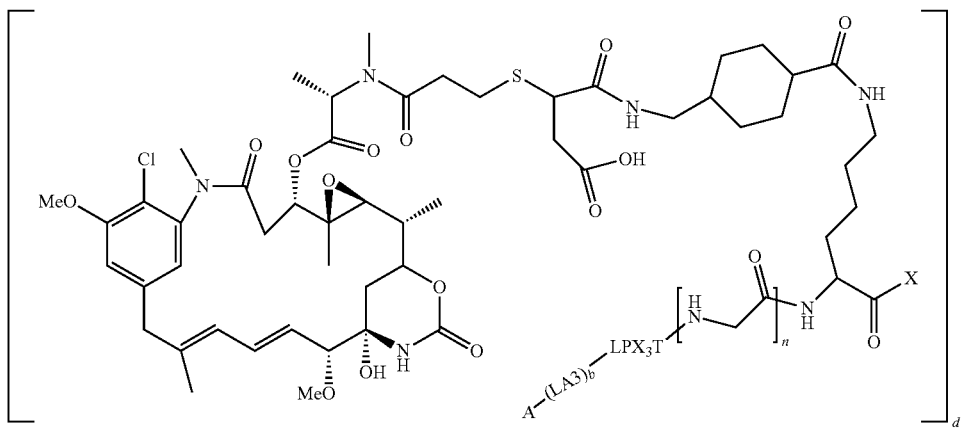
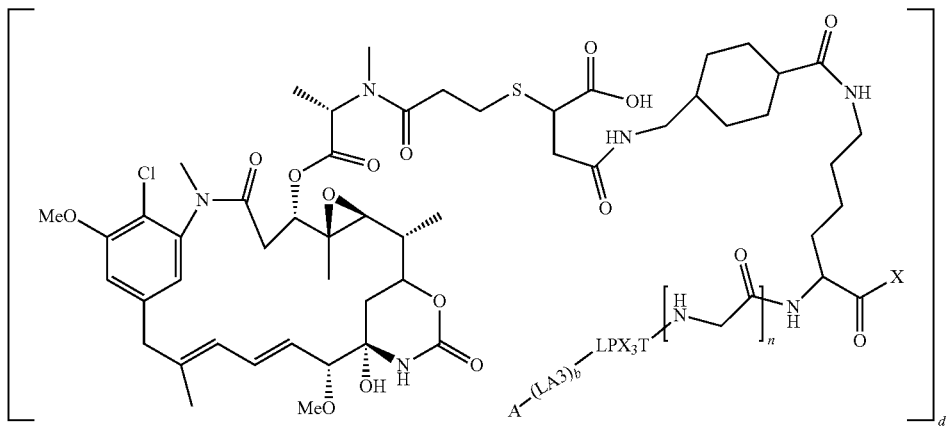

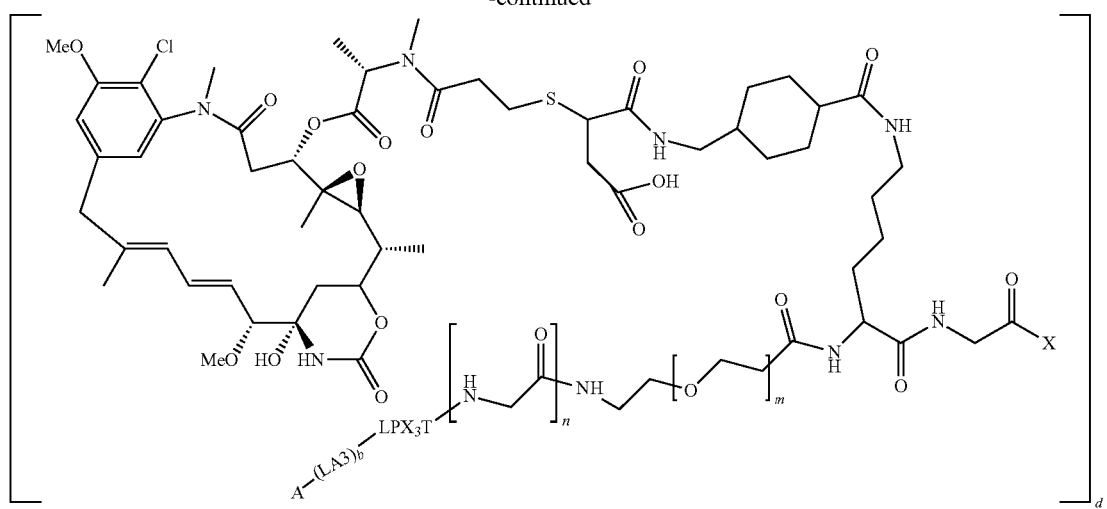
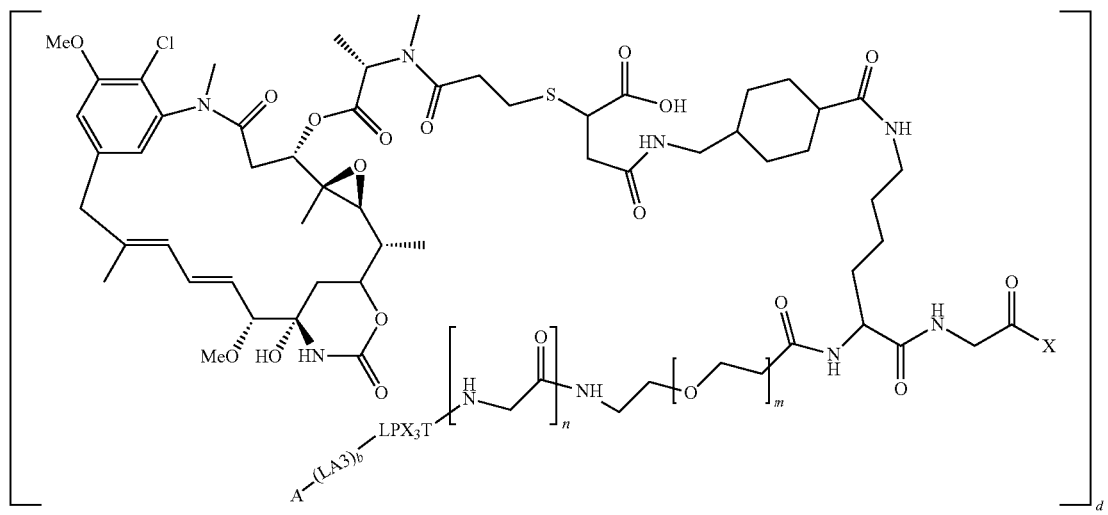
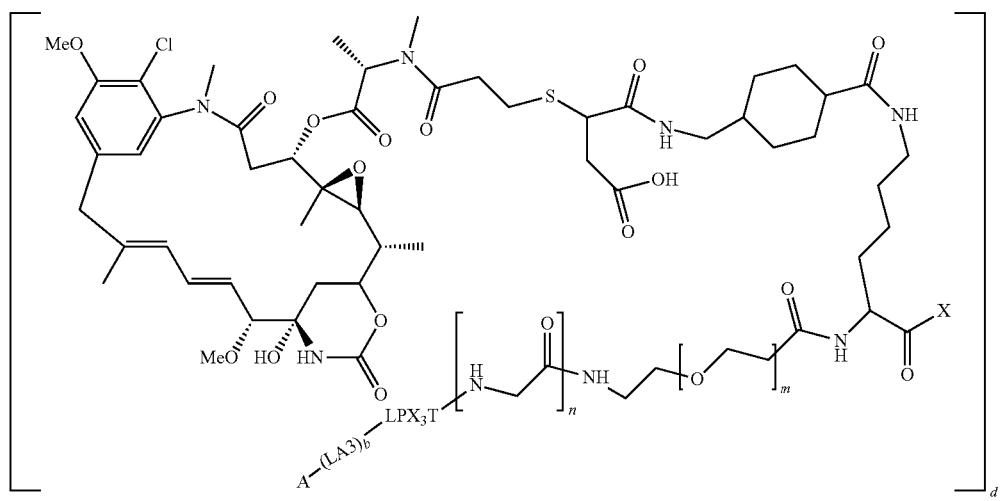

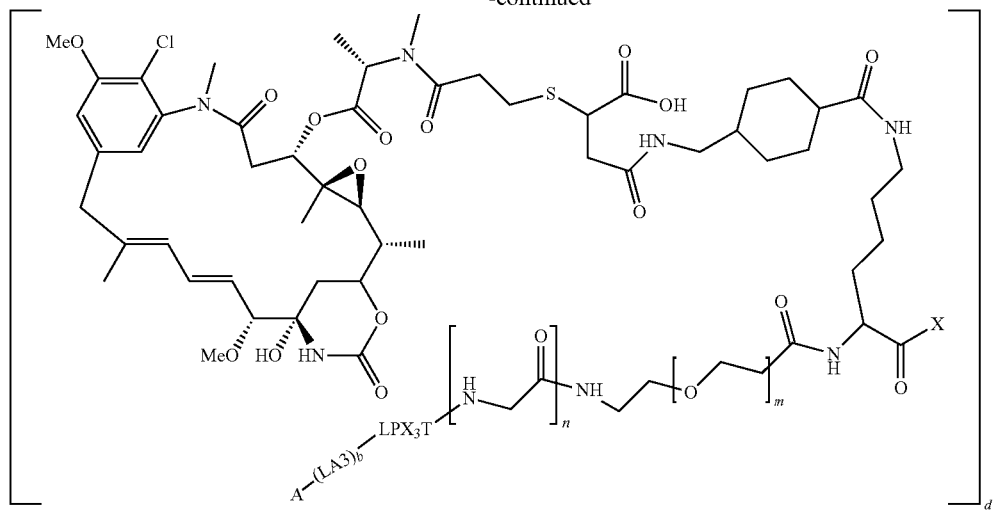

or a pharmaceutically acceptable salt thereof, wherein n represents any of the integers between 1 and 100; m is 0 or any of the integers between 1 and 1000; d represents any of the integers between 1 and 20; A is an antibody; LA3 comprises 1 to 100 series-connected structure units which are selected from the group consisting of one or more glycine and alanine; b is independently 0 or 1, that is, LA3 is independently present or absent; $X_3$ in ligase recognition sequence $LPX_3T$ is natural/unnatural amino acid; and x is —OH or —$NH_2$ group.

8. A composition comprising the compound according to claim 1, which is prepared by the following steps:
i) a compound of Formula (I) or (II) is prepared:

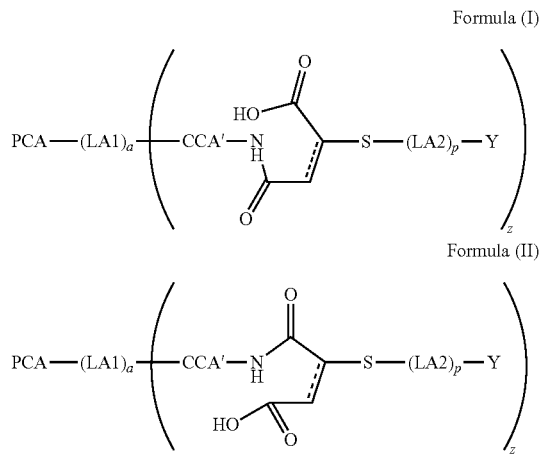

Formula (I)

Formula (II)

or a pharmaceutically acceptable salt thereof, wherein
PCA is the specific recognition sequence of the ligase donor substrate or the specific recognition sequence of the ligase acceptor substrate;
LA1 and LA2 are linker moieties;
a and p are independently 0 or 1, that is, LA1 and LA2 are independently present or absent;
CCA' is a chemical conjugation moiety;
═══ represents a single or double bond;
Y is a radioactive label, a fluorescent label, an affinity purification tag, a tracer molecule, an anticancer drug or a cytotoxic molecule;

z is any one of the integers between 1 and 1000,
ii) A-$(LA_3)_b$-F according to claim 1 is prepared;
iii) A-$(LA_3)_b$-F obtained in step ii) and a compound of Formula (I) or (II) obtained in step i) are conjugated at the presence of the ligase and under conditions suitable for action of the ligase.

9. The composition according to claim 8, wherein the total molar content of the compounds of Formula (V) or (VI) is more than 80%.

10. A method for inhibiting cell proliferation in an animal, wherein the method comprises treating the animal with the compound according to claim 1.

11. A method for treating a disease in human, wherein the method comprises treating the human with the compound according to claim 1 and wherein the disease is cancer or an autoimmune disease.

12. The method according to claim 11, wherein the disease is cancer and a tumor cell surface has a specific antigen or a receptor protein which recognizes and binds to the compound or composition, wherein the specific antigen or the receptor protein on the tumor cell surface is ErbB2/Her2.

13. The method according to claim 12, wherein the tumor is breast cancer, gastric cancer, ovarian cancer, lung cancer, colon cancer, rectal cancer, colorectal cancer or esophageal cancer.

14. A pharmaceutical composition comprising the compound of Formula (V) or (VI) according to claim 1 or any pharmaceutically acceptable salt thereof, and a pharmaceutically acceptable carrier.

15. The compound according to claim 2, wherein the anti ErbB2/Her2 antibody is Trastuzumab.

16. The compound according to claim 1, wherein the ligase is a Sortase.

17. The method according to claim 10, wherein the animal is a human.

18. The pharmaceutical composition according to claim 14, wherein the pharmaceutical composition is in the form of lyophilized powder for injection or injection liquid.

19. The compound according to claim 7, wherein $X_3$ in ligase recognition sequence $LPX_3T$ is glutamic acid (E).

20. The compound according to claim 7, wherein A is anti ErbB2/Her2 antibody.

21. The compound according to claim 20, wherein the anti ErbB2/Her2 antibody is Trastuzumab.

22. A pharmaceutical composition comprising the compound according to claim 7 or any pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 11,911,435 B2
APPLICATION NO. : 17/180645
DATED : February 27, 2024
INVENTOR(S) : Gang Qin et al.

It is certified that error appears in the above-identified patent and that said Letters Patent is hereby corrected as shown below:

In the Claims

In Column 82, Line 23, in Claim 1:
"X being leucine or asparagine" should be corrected to "$X_1$ being leucine or asparagine".

In Column 87, Lines 30-31, in Claim 7:
"$X_3$ in ligase recognition sequence $LPX_3T$ is natural/unnatural amino acid" should be corrected to "$X_3$ in ligase recognition sequence $LPX_3T$ is any natural or unnatural amino acid".

Signed and Sealed this
Twenty-first Day of May, 2024

Katherine Kelly Vidal
*Director of the United States Patent and Trademark Office*